(12) United States Patent
Jaffrey et al.

(10) Patent No.: US 11,453,646 B2
(45) Date of Patent: *Sep. 27, 2022

(54) METHODS FOR RNA DETECTION AND QUANTIFICATION

(75) Inventors: Samie R. Jaffrey, New York, NY (US); Jeremy Paige, La Jolla, CA (US)

(73) Assignee: CORNELL UNIVERSITY, Ithaca, NY (US)

(*) Notice: Subject to any disclaimer, the term of this patent is extended or adjusted under 35 U.S.C. 154(b) by 188 days.

This patent is subject to a terminal disclaimer.

(21) Appl. No.: 14/235,227

(22) PCT Filed: Jul. 27, 2012

(86) PCT No.: PCT/US2012/048701
§ 371 (c)(1),
(2), (4) Date: Apr. 3, 2014

(87) PCT Pub. No.: WO2013/016694
PCT Pub. Date: Jan. 31, 2013

(65) Prior Publication Data
US 2014/0220560 A1     Aug. 7, 2014

Related U.S. Application Data

(60) Provisional application No. 61/512,310, filed on Jul. 27, 2011, provisional application No. 61/606,254, filed on Mar. 2, 2012.

(51) Int. Cl.
| | | |
|---|---|---|
| *C07D 233/04* | (2006.01) | |
| *C12Q 1/6876* | (2018.01) | |
| *G01N 33/50* | (2006.01) | |
| *G01N 33/58* | (2006.01) | |

(52) U.S. Cl.
CPC ......... *C07D 233/04* (2013.01); *C12Q 1/6876* (2013.01); *G01N 33/5008* (2013.01); *G01N 33/582* (2013.01)

(58) Field of Classification Search
CPC .. C07D 233/04; C07D 233/96; C07D 403/06; C12Q 1/6876
USPC ...................................................... 536/23.1
See application file for complete search history.

(56) References Cited

U.S. PATENT DOCUMENTS

| | | | |
|---|---|---|---|
| 1,031,600 A | 7/1912 | Ward | |
| 6,458,559 B1 | 10/2002 | Shi et al. | |
| 6,766,183 B2 | 7/2004 | Walsh et al. | |
| 7,125,660 B2 | 10/2006 | Stanton et al. | |
| 9,664,676 B2 | 5/2017 | Jaffrey et al. | |
| 10,444,224 B2 * | 10/2019 | Jaffrey ................. | G01N 33/582 |
| 2002/0111358 A1 | 8/2002 | Nishiyama et al. | |
| 2003/0211516 A1 | 11/2003 | Davis | |
| 2004/0138227 A1 | 7/2004 | Nishiyama et al. | |
| 2006/0172320 A1 | 8/2006 | Stojanovic | |
| 2010/0216855 A1 | 8/2010 | Carreaux et al. | |
| 2011/0189663 A1 | 8/2011 | Cotterchio et al. | |
| 2012/0252699 A1 | 10/2012 | Jaffrey et al. | |
| 2015/0141282 A1 | 5/2015 | Jaffrey et al. | |
| 2019/0185434 A1 | 6/2019 | Jaffrey et al. | |

FOREIGN PATENT DOCUMENTS

| | | |
|---|---|---|
| EP | 0422900 A2 | 10/1990 |
| FR | 2919608 A1 | 1/2007 |
| JP | 2006-178325 | 7/2006 |
| WO | 2007147159 A2 | 12/2007 |
| WO | 2010096584 A1 | 8/2010 |

OTHER PUBLICATIONS

Yarmoluk et al., "Interaction of Cyanine Dyes with Nucleic Acids—XXVII: Synthesis and Spectral Properties of Novel Homodi- and Homotrimeric Monomethine Cyanine Dyes," Dyes and Pigments 50:21-28 (2001).
Dong et al., "Isomerization in Fluorescent Protein Chromophores Involves Addition/Elimination," J. Am. Chem. Soc. 130:14096-14098 (2008).
Lotfy Aly et al., "Intercalating Nucleic Acids with Insertion of 5-[(Pyren-1-yl)methylidene]hydantoin-Substituted Butane-1,2-diol," Helvetica Chimica Acta 88:3137-3144 (2005).
Narang et al., "CXXXV.—Studies in Chemotherapy (Antimalarials). Part I. A Derivative of Glyoxalinoquinoline," J. Chem. Soc. p. 976 (Jan. 1, 1931).
Petersen et al., "Synthesis and Characterization of Model Compounds for the Neutral Green Fluorescent Protein Chromophore," Synthesis 23:3635-3638 (2007).
Socher et al., "FIT Probes: Peptide Nucleic Acid Probes with a Fluorescent Base Surrogate Enable Real-Time DNA Quantification and Single Nucleotide Polymorphism Discovery," Analyt. Biochem. 375:318-330 (2008).
Stafforst et al., "Synthesis of Alaninyl and N-(2-Aminoethyl)glycinyl Amino Acid Derivatives Containing the Green Fluorescent Protein Chromophore in their Side Chains for Incorporation into Peptides and Peptide Nucleic Acids," Eur. J. Org. Chem. 899-911 (2007).
Ajmera et al. "CNS-Depressant and Anticonvulsant Activities of 1-Substituted Phenyl (Aryl)-2-Methyl-4 (3,4,5, Trimethoxybenzylidene)-5-Imidazolones," Drugs Expt Clin Res 6(3):171-176 (1980).
Nichols et al. "Serotoin Receptors," Chem Rev 108:1614-1641 (2008).
Bourotte et al. "Fluorophores Related to the Green Fluorescent Protein," Tetrahedron Letters 45:343-6348 (2004).
He et al. "Synthesis and Spectroscopic Studies of Model Red Fluorescent Protein Chromophores," Organic Letters 4(9):1523-1526 (2002).

(Continued)

*Primary Examiner* — Jezia Riley
(74) *Attorney, Agent, or Firm* — Troutman Pepper Hamilton Sanders LLP (Rochester)

(57) ABSTRACT

The present invention relates to novel nucleic acid molecules, called aptamers, that bind specifically to a small molecule fluorophore and thereby enhance the fluorescence signal of the fluorophore upon exposure to radiation of suitable wavelength. Molecular complexes formed between the novel fluorophores, novel nucleic acid molecules, and their target molecules are described, and the use of multivalent aptamer constructs as fluorescent sensors for target molecules of interest are also described.

14 Claims, 23 Drawing Sheets

Specification includes a Sequence Listing.

(56) References Cited

OTHER PUBLICATIONS

You et al. "Fluorophores Related to the Green Fluorescent Protein and Their Use in Optoelectronic Devices," Advanced Materials 12(22):1678-1681 (2000).
Badr et al. "Synthesis of 1,2-Disubstituted 4-Benzylidene-2-Imidazolin-5-ones and their Thione Derivatives," Indian Jour of Chem 18B(3):240-242 (1979) (Abstract only).
Grate et al. "Laser-mediated, Site-specific Inactivation of RNA Transcripts," Proc Natl Acad Sci USA 96:6131-6136 (1999).
Lerestif et al. "Cycloaddition with Stabilized Imidates as Potential Azomethines Ylides : A New Route to 2-Imidazoline and 4-Yliden-5-Imidazolinone," Tetrahedron Letters 34(29):4639-4642 (1993).
Stanlis et al., "Single-strand DNA Aptamers as Probes for Protein Localization in Cells," J. Histochem Cytochem. 51(6):797-808 (2003).
Stojanovic et al., "Modular Aptameric Sensors," JACS 126:9266-9270 (2004).
International Search Report and Written Opinion for corresponding application No. PCT/US12/48701 dated Jan. 23, 2013 (13 pages).
Fischer et al., "Massively Parallel Interrogation of Aptamer Sequence, Structure and Function," PLoS One 3(7) e2720 (2008).
Shaner et al., "Advances in Fluorescent Protein Technology," J. Cell Sci. 120(Pt 24):4247-4260 (2007).
Zhang et al., "Creating New Fluorescent Probes for Cell Biology," Nature 3(12):906-918 (2002).
Szent-Gyorgyi et al., "Fluorogen-Activating Single-Chain Antibodies for Imaging Cell Surface Proteins," Nature Biotechnol. 26(2):235-240 (2008).
Babendure et al., "Aptamers Switch on Fluorescence of Tri phenylmethane Dyes," J. Am. Chem. Soc 125 (48)114716-14717 (2003).
Pakhomov & Martynov, "GFP Family: Structural Insights into Spectral Tuning," Chem. Biol. 15(8):755-764 (2008).
Bellobono et al., "Kinetics of Base-Catalysed Condensation of 5-Methylfuran-2(3H)-one with 2-Hydroxybenzaldehyde," J. Chem. Soc. 1773-1776 (1976).
Bharathi et al., "Synthesis, Pharmacological Evaluation and QSAR Studies of 4,5-Dihydro-4-[(Substituted Phenyl) Methylene]-5-oxo-2-Phenyl/methyl-1 H-Imidazole-1-Acetic Acids," Indian Journal of Pharmaceutical Sciences, Indian J. Pharm. Sci. 186-189 (1999).
Rajbongshi et al., "Dominant Pi---Pi Interaction in the Self Assemblies of 4-Benzylidene Imidazolin-5-one Analogs," J. Chem. Sci. 121(6):973-982 (2009).
Chidvilas et al., "Bilayer Organic Solar Cells Based on Imidazolin-5-one Molecules," Presented at the Instituted of Electrical and Electronics Engineers (IEEE) Conference, Jun. 7-12, 2009; and published in the 2009 34th IEEE Photovoltaic Specialists Conference (PVSC) 19(1):813-815 (2009).
Chidvilas et al., Reference Date, "Bilayer Organic Solar Cells Based on Imidazolin-5-one Molecules," Presented at the IEEE Conference, Jun. 7-12, 2009; and published in the 2009 34th IEEE Photovoltaic Specialists Conference (PVSC), 19(1):813-815 (2009).
Tripathy, P., "Microwave Activated Synthesis of 2-Imidazolin-5-ones Using Phenyl Isothiocyanate as Cyclocondensing Agent," Asian Journal of Chemistry 19(1):813-815 (2007).
Baptista et al., "Effect of BSA Binding on Photophysical and Photochemical Properties of Triarylmethane Dyes," J. Phys. Chem. B. 102:4678-4688 (1988).
Warner et al., "Structural Basis for Activity of Highly Efficient RNA Mimics of Green Fluorescent Protein," Nat. Struct. Mol. Biol. 21(8):658-663 (2014) [Advanced Online Publication].
Debler et al., "Deeply Inverted Electron-Hole Recombination in a Luminescent Antibody-Stilbene Complex," Science 319:1232-1235 (2008).
Huang et al., "A G-Quadruplex-Containing RNA Activities Fluorescence in a GFP-Like Fluorophore," Nat. Chem. Biol. 10:686-691 (2014).
Heijnen et al., "Synthesis of Substituted Benzaldehydes via a Two-Step, One-Pot Reduction/Cross-Coupling Procedure," Org. Lett. 21:4087-4091 (2019).
Lincke et al., "On The Absorption of the Phenolate Chromophore in the Green Fluorescent Protein—Role of Individual Interactions," Chem. Comm. 46(5):734-736 (2010).
Second Declaration of Sarnie R. Jaffrey Under 37 C.F.R § 1.132 in U.S. Appl. No. 13/202,250, pp. 1-52 (dated Aug. 19, 2015).
Shaner et al., "A Guide to Choosing Fluorescent Proteins," Nature Methods 2(12):905-909 (2005).
PCT International Search Report and Written Opinion for PCT/US10/24622, dated Jul. 30, 2010.
Supplementary International Search Report and Written Opinion dated Dec. 5, 2012, for EP Patent Application No. 10744308.7 (12 pages).
Strack et al., "A Superfolding Spinach2 Reveals the Dynamic Nature of Trinucleotide Repeat-Containing RNA," Nat. Methods 10(12):1219-1224 (2013) [Author Manuscript].
Song et al., "Plug-and-Play Fluorophores Extend the Spectral Properties of Spinach," J. Am. Chem. Soc. 136(4):1198-11201 (2014).
Filonov et al., "Broccoli: Rapid Selection of an RNA Mimic of Green Fluorescent Protein by Fluorescence-Based Selection and Directed Evolution," J. Am. Chem. Soc. 136(46):16299-16308 (2014).
Paige et al., "Fluorescence Imaging of Cellular Metabolites with RNA," Science 335(6073):1194 (2012) [Author Manuscript].
Paige et al., "RNA Mimics of Green Fluorescent Protein," Science 333(6042):642-646 (2011).
Goodsell, "Green Fluorescent Protein (GFP)," Jun. 2003 Molecule of the Month (RCSB Protein Data Bank).
Baptista et al., "Effect of BSA Binding on Photophysical and Photochemical Properties of Triarylmethane Dyes," J. Phys. Chem. B. 102:4678-4688 (1998).
Second Declaration of Sarnie R. Jaffrey Under 37 C.F.R § 1.132 in U.S. Appl. No. 13/202,250 (dated Aug. 19, 2015).
Declaration of Sarnie R. Jaffrey Under 37 C.F.R § 1.132 in U.S. Appl. No. 13/202,250 (dated Feb. 3, 2014).
Carl Zeiss Microscopy Online Campus (http://zeiss-campus.magnet.fsu.edu/print/probes/anthozoafps-print.html).
Stepanenko et al., "Beta-Barrel Scaffold of Fluorescent Proteins: Folding, Stability and Role in Chromophore Formation," Int. Rev. Cell Mol. Biol. 302:221-278 (2013) [Author Manuscript].
Official Communication in EP 10744308.7 (dated Sep. 23, 2014).
Official Communication in EP 10744308.7 (dated May 2, 2016).
Official Communication in EP 10744308.7 (dated Jul. 21, 2017).
Notification for Division of Application in CN 201080017269.0 (dated Feb. 7, 2014) (English translation).
Autour et al., "iSpinach: A Fluorogenic RNA Aptamer Optimized for In Vitro Applications," Nucleic. Acids. Res. 44(6):2491-2500 (2016).
Follenius-Wund et al., "Flurorescent Derivatives of the GFP Chromophore Give a New Insight into the GFP Fluorescence Process," Biophysical Journal 85:1839-1850 (2003).
Kennephohl et al., 21.2 Nucleophilic Acyl Substitution Reactions, Chemistry LibreTexts, pp. 1-5. (2020) [Accessed at https://chem.libretexts.org/Courses/Athabasca_University/Chemistry_360%3A_Organic_ . . . on Nov. 12, 2021 ].
National University of Singapore, Chapter 6, "Nucleophilic Addition to the Carbonyl Group," National University of Singapore, pp. 125-140(2021).
Song et al., "Imaging RNA Polymerase III Transcription Using a Photostable RNA-Fluorophore Complex," Nat. Chem. Biol. 13(11):1187-1194 (2017) [Author Manuscript].

* cited by examiner

```
CLUSTAL W --- LocARNA 1.5.2 - Local Alignment of RNA

5' stem                              Stem Loop 1                              Stem Loop 2
                   ---(((((((((...........              -(((((....)))-.(.(-----(((((....))))-----)
SEQ ID NO: 4       GGGAGAGCGCAACUGAAUGAAAUGGUGAA-GGACGGGUCC--AGGUGUGGCUGCUUCGGCAGU-GCAGC
SEQ ID NO: 5       GGGAGAGCGCAACUGAAUGAAAUGGUGAA-GGACGGGUCC--AGGUGUGGCUGCUUCGGCAGU-GCAGC
SEQ ID NO: 6       -----GACGCGACUGAAUGAAAUGGUGAA-GGACGGGUCC--AGGUGUGGCUGCUUCGGCAGU-GCAGC
SEQ ID NO: 7       -----GACGCGACC-----GAAAUGGUGAA-GGACGGGUCC--AG------UGCUUCGGCA-----C
SEQ ID NO: 8       -----GACGCGACUGAAUGAAAUGGUGAA-GGACGGGUCC--AG------CUGCUUCGCAG-----C
SEQ ID NO: 9       -----GACGCGACUGAAUGAAAUGGUGAA-GGACGGGUCC--AG------GCACGAAAGUGC-----C
SEQ ID NO: 10      -----GACGCAACUGAAUGAAAUGGUGAA-GGACGGGUCC--AGGUGUGGCUGCUUCGGCAGU-GCAGC
SEQ ID NO: 11      -----GACGCGACCU-AUGAAAUGGUGAA-GGACGGGUCCCAGC-G--GCUGCUUCGGCAGC--CG-C
SEQ ID NO: 12      -----GACGCGACCGAAUGAAAUGGUGAA-GGACGGGUCC--AGGUGUGGCUGCUUCGGCAGU-GCAGC
SEQ ID NO: 13      -----GACGCGACCGAAUGAAAUGGUGAA-GGACGGGUCC--AGGUGCGGCUGCAGCCGCAGC
SEQ ID NO: 14      -----GACGCGACCGAAUGAAAUGGUGAA-GGACGGGUCC--AGGUGUGGCUGCUUCGGCAGU-GCAGC
SEQ ID NO: 15      -----GACGCGACCGAAUGAAAUGGUGAA-GGACGGGUCC--AGCCG--GCUGCUUCGGCAGC--GGC
                   ....(((((((((.....            .)))..(    ((((....))))....)
SEQ ID NO: 1       GACGCNACNNNNNGAAAUGGUGAANGGACGGGUCCNAGNNNNNNNNNNNNNNNNNNNNNNNC Stem Loop 3                                3' stem
                   .((((((....))))))---..))).))))))))---
SEQ ID NO: 4       UUGUUGAGUAGAGUGUGAGCUCCGCGUAACUAGUCCGUCAC
SEQ ID NO: 5       UUGUUGAGUAGAGUGUGAGCUC--CGUAACUAGUCCGUCAC
SEQ ID NO: 6       UUGUUGAGUAGAGUGUGAGCUC--CGUAACUAGUCGGUC--
SEQ ID NO: 7       UUGUUGAGUAGAGUGUGAGCUC--CGUAACUAGUCGGUC--
SEQ ID NO: 8       UUGUUGAGUAGAGUGUGAGCUC--CGUAACUAGUCGGUC--
SEQ ID NO: 9       UUGUUGAGUAGAGUGUGAGCUC--CGUAACUAGUCGGUC--
SEQ ID NO: 10      UUGUUGAGUAGAGUGUGAGCUC--CGUAACUAGUCGGUC--
SEQ ID NO: 11      -UGUUGAGUAGAGUGUGAGCUC--CGUAACUAGUCGGUC--
SEQ ID NO: 12      UUGUUGAGUAGAGUGUGAGCUC--CGUAACUAGUCGGUC--
SEQ ID NO: 13      UUGUUGAGUAGAGUGUGAGCUC--CGUAACUAGUCGGUC--
SEQ ID NO: 14      UUGUUGCGUCGAGUAGAGUGAGCUCGACGUAACUAGUCGGUC--
SEQ ID NO: 15      UUGUUGAGUAGAGUGUGAGCUC--CGUAACUAGUCGGUC--
                   ..(((((....))))...))).))))).)))))))..
SEQ ID NO: 1       NUGUUGNGUNGAGUGUGAGCUCNNNCGUAACUNGUCGCGUC
```

FIG. 1

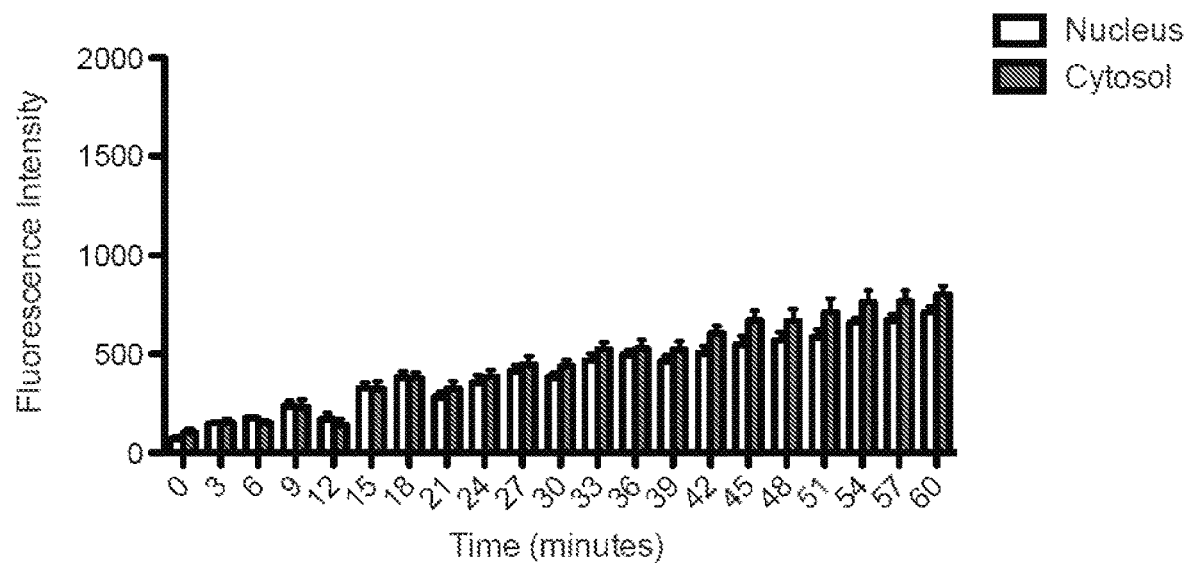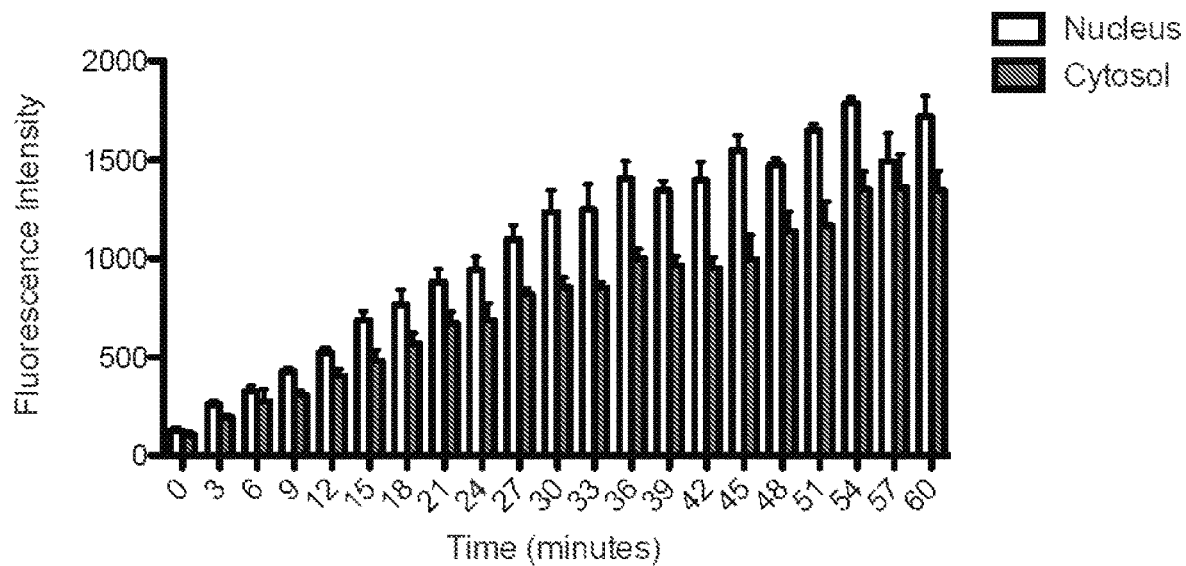
FIG. 6

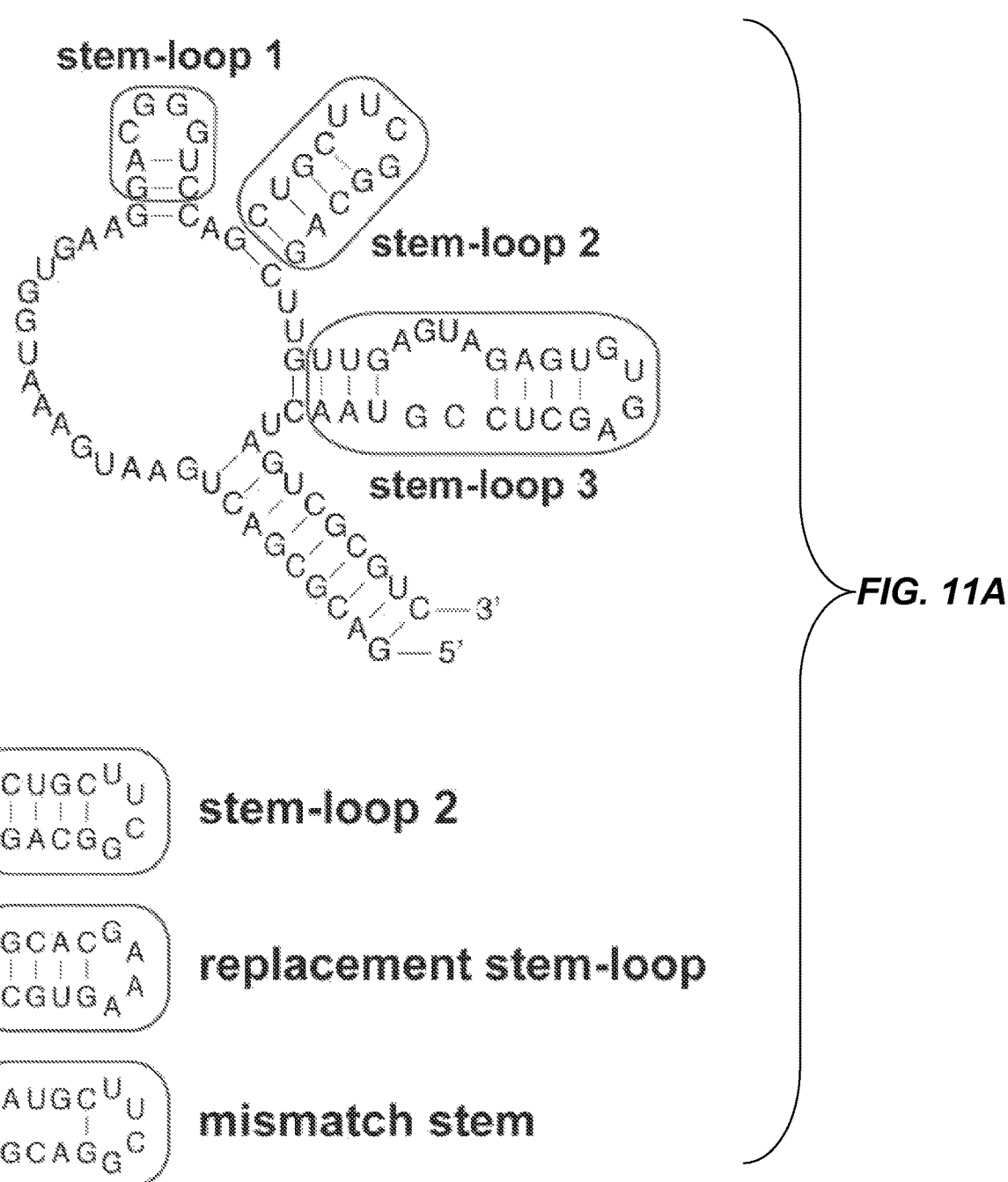

SEQUENCE LISTING

```
<160> NUMBER OF SEQ ID NOS: 59

<210> SEQ ID NO 1
<211> LENGTH: 103
<212> TYPE: RNA
<213> ORGANISM: Artificial
<220> FEATURE:
<223> OTHER INFORMATION: consensus sequence for RNA aptamers binding to
      4-(3,5-difluoro-4-hydroxybenzylidene)-1,2-dimethyl-imidazol-5-one
<220> FEATURE:
<221> NAME/KEY: misc_feature
<222> LOCATION: (6)..(6)
<223> OTHER INFORMATION: N can be A, U, G, or C
<220> FEATURE:
<221> NAME/KEY: misc_feature
<222> LOCATION: (9)..(9)
<223> OTHER INFORMATION: N can be A, U, G, or C
<220> FEATURE:
<221> NAME/KEY: misc_feature
<222> LOCATION: (10)..(13)
<223> OTHER INFORMATION: N is optional and can be A, U, G, or C
<220> FEATURE:
<221> NAME/KEY: misc_feature
<222> LOCATION: (25)..(25)
<223> OTHER INFORMATION: N is optional and independently can be A, U, G,
      or C, and may together form a stable or partially stable base pair
      with N at position 36
<220> FEATURE:
<221> NAME/KEY: misc_feature
<222> LOCATION: (36)..(36)
<223> OTHER INFORMATION: N is optional and independently can be A, U, G,
      or C, and may together form a stable or partially stable base pair
      with N at position 25
<220> FEATURE:
<221> NAME/KEY: misc_feature
<222> LOCATION: (39)..(44)
<223> OTHER INFORMATION: N is optional and independently can be A, U, G,
      or C, forming a partially stabilized antiparallel stem structure
      together with N at positions 57-62
<220> FEATURE:
<221> NAME/KEY: misc_feature
<222> LOCATION: (45)..(56)
<223> OTHER INFORMATION: N is independently A, U, G, or C, and may
      together form a stable stemloop structure
<220> FEATURE:
<221> NAME/KEY: misc_feature
<222> LOCATION: (57)..(62)
<223> OTHER INFORMATION: N is optional and independently can be A, U, G,
      or C, forming a partially stabilized antiparallel stem structure
      together with N at positions 39-44
<220> FEATURE:
<221> NAME/KEY: misc_feature
<222> LOCATION: (64)..(64)
<223> OTHER INFORMATION: N is optional and can be A, U, G, or C
<220> FEATURE:
<221> NAME/KEY: misc_feature
<222> LOCATION: (70)..(70)
<223> OTHER INFORMATION: N is optional and can independently be A, U, G,
      or C
<220> FEATURE:
<221> NAME/KEY: misc_feature
<222> LOCATION: (73)..(73)
<223> OTHER INFORMATION: N is optional and can independently be A, U, G,
      or C
<220> FEATURE:
<221> NAME/KEY: misc_feature
<222> LOCATION: (86)..(87)
```

<223> OTHER INFORMATION: N is optional and can independently be A, U, G,
      or C, except that together they are not CG
<220> FEATURE:
<221> NAME/KEY: misc_feature
<222> LOCATION: (95)..(95)
<223> OTHER INFORMATION: N can be A, U, G, or C

<400> SEQUENCE: 1
gacgcnacnn nnngaaaugg ugaaggacg gguccnagnn nnnnnnnnnn nnnnnnnnnn    60
nncnuguugn gungagugug agcucnncgu aacungucgc guc                    103

<210> SEQ ID NO 2
<211> LENGTH: 103
<212> TYPE: RNA
<213> ORGANISM: Artificial
<220> FEATURE:
<223> OTHER INFORMATION: consensus sequence for RNA a -continued

```
<220> FEATURE:
<221> NAME/KEY: misc_feature
<222> LOCATION: (61)..(61)
<223> OTHER INFORMATION: N is optional and can be A, U, G, or C, and may
      together form a stable or partially stable base pair with the
      ribonucleotide at position 40
<220> FEATURE:
<221> NAME/KEY: misc_feature
<222> LOCATION: (64)..(64)
<223> OTHER INFORMATION: N is optional and can be A, U, G, or C
<220> FEATURE:
<221> NAME/KEY: misc_feature
<222> LOCATION: (70)..(70)
<223> OTHER INFORMATION: N is optional and can independently be A, U, G,
      or C
<220> FEATURE:
<221> NAME/KEY: misc_feature
<222> LOCATION: (73)..(73)
<223> OTHER INFORMATION: N is optional and can independently be A, U, G,
      or C
<220> FEATURE:
<221> NAME/KEY: misc_feature
<222> LOCATION: (86)..(87)
<223> OTHER INFORMATION: N is optional and can independently be A, U, G,
      or C, except that they are not CG
<220> FEATURE:
<221> NAME/KEY: misc_feature
<222> LOCATION: (95)..(95)
<223> OTHER INFORMATION: N can be A, U, G, or C, and may together form a
      stable base pair with the ribonucleotide at position 9

<400> SEQUENCE: 2
gacgcnacnn nnngaaaugg ugaanggacg gguccnagnn gnngcugcuu cggcagnnnc      60
ngcnuguugn gungagugug agcucnncgu aacungucgc guc                      103

<210> SEQ ID NO 3
<211> LENGTH: 99
<212> TYPE: RNA
<213> ORGANISM: Artificial
<220> FEATURE:
<223> OTHER INFORMATION: consensus sequence for RNA aptamers binding to
      4-(3,5-difluoro-4-hydroxybenzylidene)-1,2-dimethyl-imidazol-5-one
<220> FEATURE:
<221> NAME/KEY: misc_feature
<222> LOCATION: (6)..(6)
<223> OTHER INFORMATION: N can be A, U, G, or C
<220> FEATURE:
<221> NAME/KEY: misc_feature
<222> LOCATION: (9)..(9)
<223> OTHER INFORMATION: N can be A, U, G, or C
<220> FEATURE:
<221> NAME/KEY: misc_feature
<222> LOCATION: (10)..(13)
<223> OTHER INFORMATION: N is optional and can independently be A, U, G,
      or C
<220> FEATURE:
<221> NAME/KEY: misc_feature
<222> LOCATION: (37)..(38)
<223> OTHER INFORMATION: N can be A, U, G, or C
<220> FEATURE:
<221> NAME/KEY: misc_feature
<222> LOCATION: (40)..(41)
<223> OTHER INFORMATION: N is optional and can be A, U, G, or C
<220> FEATURE:
<221> NAME/KEY: misc_feature
<222> LOCATION: (55)..(55)
<223> OTHER INFORMATION: N can be A, U, G, or C
<220> FEATURE:
<221> NAME/KEY: misc_feature
<222> LOCATION: (56)..(56)
<223> OTHER INFORMATION: N is optional and can be A, U, G, or C, and may
      together form a stable or partially stable base pair with the
      ribonucleotide at position 41
<220> FEATURE:
<221> NAME/KEY: misc_feature
<222> LOCATION: (57)..(57)
```

```
<223> OTHER INFORMATION: N is optional and can be A, U, G, or C, and may
      together form a stable or partially stable base pair with the
      ribonucleotide at position 40
<220> FEATURE:
<221> NAME/KEY: misc_feature
<222> LOCATION: (59)..(59)
<223> OTHER INFORMATION: N is optional and can be A, U, G, or C, and may
      together form a stable or partially stable base pair with the
      ribonucleotide at position 38
<220> FEATURE:
<221> NAME/KEY: misc_feature
<222> LOCATION: (62)..(62)
<223> OTHER INFORMATION: N is optional and can be A, U, G, or C
<220> FEATURE:
<221> NAME/KEY: misc_feature
<222> LOCATION: (91)..(91)
<223> OTHER INFORMATION: N can be A, U, G, or C, and may together form a
      stable base pair with the ribonucleotide at position 9

<400> SEQUENCE: 3
gacgcnacnn nnngaaaugg ugaaggacgg guccagnngn ngcugcuucg gcagnnncng      60
cnuguugagu agagugugag cuccguaacu ngucgcguc                             99

<210> SEQ ID NO 4
<211> LENGTH: 106
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one

<400> SEQUENCE: 4
gggagacgca acugaaugaa auggugaagg acggguccag guguggcugc uucggcagug      60
cagcuuguug aguagagugu gagcuccgcg uaacuagucg cgucac                    106

<210> SEQ ID NO 5
<211> LENGTH: 104
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one

<400> SEQUENCE: 5
gggagacgca acugaaugaa auggugaagg acggguccag guguggcugc uucggcagug      60
cagcuuguug aguagagugu gagcuccgua acuagucgcg ucac                      104

<210> SEQ ID NO 6
<211> LENGTH: 98
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one

<400> SEQUENCE: 6
gacgcgacug aaugaaaugg ugaaggacgg guccaggugu ggcugcuucg gcagugcagc      60
uuguugagua gagugugagc uccguaacua gucgcguc                              98

<210> SEQ ID NO 7
<211> LENGTH: 80
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one
```

```
<400> SEQUENCE: 7
gacgcgaccg aaauggugaa ggacgggucc agugcuucgg cacuguugag uagaguguga    60
gcuccguaac uggucgcguc                                               80

<210> SEQ ID NO 8
<211> LENGTH: 87
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one

<400> SEQUENCE: 8
gacgcgacug aaugaaaugg ugaaggacgg guccagcugc uucggcagcu uguugaguag    60
agugugagcu ccguaacuag ucgcguc                                       87

<210> SEQ ID NO 9
<211> LENGTH: 87
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one

<400> SEQUENCE: 9
gacgcgacug aaugaaaugg ugaaggacgg guccaggcac gaaagugccu uguugaguag    60
agugugagcu ccguaacuag ucgcguc                                       87

<210> SEQ ID NO 10
<211> LENGTH: 98
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one

<400> SEQUENCE: 10
gacgcaacug aaugaaaugg ugaaggacgg guccaggugu ggcugcuucg gcagugcagc    60
uuguugagua gagugugagc uccguaacua gucgcguc                           98

<210> SEQ ID NO 11
<211> LENGTH: 93
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one

<400> SEQUENCE: 11
gacgcgaccu augaaauggu gaagggacgg gucccagcgg cugcuucggc agccgcuguu    60
gaguagagug ugagcuccgu aacuggucgc guc                                93

<210> SEQ ID NO 12
<211> LENGTH: 98
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one

<400> SEQUENCE: 12
gacgcgaccg aaugaaaugg ugaaggacgg guccaggugu ggcugcuucg gcagugcagc    60
```

```
uuguugagua gagugugagc uccguaacug gucgcguc                   98
```

```
<210> SEQ ID NO 13
<211> LENGTH: 99
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one

<400> SEQUENCE: 13
gacgcgaccg aaugaaaugg ugaaggacgg guccagcugc ggcugcuucg gcagccgcag    60
cuuguugagu agagugugag cuccguaacu ggucgcguc                          99

<210> SEQ ID NO 14
<211> LENGTH: 100
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one

<400> SEQUENCE: 14
gacgcgaccg aaugaaaugg ugaaggacgg guccaggugu ggcugcuucg gcagugcagc    60
uuguugcguc gagugugagc ucgacguaac uggucgcguc                        100

<210> SEQ ID NO 15
<211> LENGTH: 95
<212> TYPE: RNA
<213> ORGANISM: Artificial
<220> FEATURE:
<223> OTHER INFORMATION: RNA aptamer that binds to
      4-(3,5-difluoro-4-hydroxybenzylidene)-1,2-dimethyl-imidazol-5-one

<400> SEQUENCE: 15
gacgcgaccg aaugaaaugg ugaaggacgg guccagccgg cugcuucggc agccggcuug    60
uugaguagag ugugagcucc guaacugguc gcguc                              95

<210> SEQ ID NO 16
<211> LENGTH: 12
<212> TYPE: RNA
<213> ORGANISM: Artificial
<220> FEATURE:
<223> OTHER INFORMATION: mismatched stem

<400> SEQUENCE: 16
augcuucgga cg                                                       12

<210> SEQ ID NO 17
<211> LENGTH: 108
<212> TYPE: RNA
<213> ORGANISM: Artificial
<220> FEATURE:
<223> OTHER INFORMATION: adenosine sensor

<400> SEQUENCE: 17
gacgcgacug aaugaaaugg ugaaggacgg guccagcugc agaaacugug gcacuucggu    60
gccaggcagc uuguugagua gagugugagc uccguaacua gucgcguc               108

<210> SEQ ID NO 18
<211> LENGTH: 113
<212> TYPE: RNA
<213> ORGANISM: Artificial
<220> FEATURE:
```

```
<223> OTHER INFORMATION: adenosine sensor

<400> SEQUENCE: 18
gacgcgacug aaugaaaugg ugaaggacgg guccaguaau gggaagaaac uguggcacuu      60
cggugccagc guugcuuguu gaguagagug ugagcuccgu aacuagucgc guc            113

<210> SEQ ID NO 19
<211> LENGTH: 111
<212> TYPE: RNA
<213> ORGANISM: Artificial
<220> FEATURE:
<223> OTHER INFORMATION: weak adenosine sensor

<400> SEQUENCE: 19
gacgcgacug aaugaaaugg ugaaggacgg guccaguugu ggaagaaacu guggcacuuc      60
ggugccaggc agcuuguuga guagagugug agcuccguaa cuagucgcgu c              111

<210> SEQ ID NO 20
<211> LENGTH: 115
<212> TYPE: RNA
<213> ORGANISM: Artificial
<220> FEATURE:
<223> OTHER INFORMATION: adenosine sensor

<400> SEQUENCE: 20
gacgcgacug aaugaaaugg ugaaggacgg guccagugug ugggaagaaa cuguggcacu      60
ucggugccag cguaugcuug uugaguagag ugugagcucc guaacuaguc gcguc           115

<210> SEQ ID NO 21
<211> LENGTH: 115
<212> TYPE: RNA
<213> ORGANISM: Artificial
<220> FEATURE:
<223> OTHER INFORMATION: weak adenosine sensor

<400> SEQUENCE: 21
gacgcgacug aaugaaaugg ugaaggacgg guccaguaug ugggaagaaa cuguggcacu      60
ucggugccag cggaugcuug uugaguagag ugugagcucc guaacuaguc gcguc           115

<210> SEQ ID NO 22
<211> LENGTH: 115
<212> TYPE: RNA
<213> ORGANISM: Artificial
<220> FEATURE:
<223> OTHER INFORMATION: adenosine sensor

<400> SEQUENCE: 22
gacgcgacug aaugaaaugg ugaaggacgg guccagugcg ugggaagaaa cuguggcacu      60
ucggugccag cgugugcuug uugaguagag ugugagcucc guaacuaguc gcguc           115

<210> SEQ ID NO 23
<211> LENGTH: 115
<212> TYPE: RNA
<213> ORGANISM: Artificial
<220> FEATURE:
<223> OTHER INFORMATION: adenosine sensor

<400> SEQUENCE: 23
gacgcgacug aaugaaaugg ugaaggacgg guccagugag ugggaagaaa cuguggcacu      60
ucggugccag cguucgcuug uugaguagag ugugagcucc guaacuaguc gcguc           115
```

```
<210> SEQ ID NO 24
<211> LENGTH: 114
<212> TYPE: RNA
<213> ORGANISM: Artificial
<220> FEATURE:
<223> OTHER INFORMATION: weak ADP sensor

<400> SEQUENCE: 24
gacgcgacug aaugaaaugg ugaaggacgg guccagcaca cgagggggaa accccggaca      60
aucagacacg guguucuugu ugaguagagu gugagcuccg uaacuagucg cguc           114

<210> SEQ ID NO 25
<211> LENGTH: 112
<212> TYPE: RNA
<213> ORGANISM: Artificial
<220> FEATURE:
<223> OTHER INFORMATION: ADP sensor

<400> SEQUENCE: 25
gacgcgacug aaugaaaugg ugaaggacgg guccagacac gagggggaaa ccccggacaa      60
ucagacacgg ugucuuguug aguagagugu gagcuccgua acuagucgcg uc             112

<210> SEQ ID NO 26
<211> LENGTH: 110
<212> TYPE: RNA
<213> ORGANISM: Artificial
<220> FEATURE:
<223> OTHER INFORMATION: ADP sensor

<400> SEQUENCE: 26
gacgcgacug aaugaaaugg ugaaggacgg guccagcacg aggggaaac cccggacaau       60 cagacacggu gcuuguugag uagagguga gcuccguaac uagucgcguc                  110

<210> SEQ ID NO 27
<211> LENGTH: 108
<212> TYPE: RNA
<213> ORGANISM: Artificial
<220> FEATURE:
<223> OTHER INFORMATION: weak ADP sensor

<400> SEQUENCE: 27
gacgcgacug aaugaaaugg ugaaggacgg guccagacga ggggaaacc ccggacaauc       60 agacacgguc uuguugagua gagugugagc uccguaacua gucgcguc                   108

<210> SEQ ID NO 28
<211> LENGTH: 106
<212> TYPE: RNA
<213> ORGANISM: Artificial
<220> FEATURE:
<223> OTHER INFORMATION: weak ADP sensor

<400> SEQUENCE: 28
gacgcgacug aaugaaaugg ugaaggacgg guccagcgag ggggaaaccc cggacaauca      60
gacacggcuu guugaguaga gugugagcuc cguaacuagu cgcguc                     106

<210> SEQ ID NO 29
<211> LENGTH: 112
<212> TYPE: RNA
<213> ORGANISM: Artificial
<220> FEATURE:
<223> OTHER INFORMATION: weak ADP sensor

<400> SEQUENCE: 29
```

```
gacgcgacug aaugaaaugg ugaaggacgg guccagcacc gagggggaaa ccccggacaa    60
ucagacacgg guucuuguug aguagagugu gagcuccgua acuagucgcg uc           112
```

<210> SEQ ID NO 30
<211> LENGTH: 110
<212> TYPE: RNA
<213> ORGANISM: Artificial
<220> FEATURE:
<223> OTHER INFORMATION: weak ADP sensor

<400> SEQUENCE: 30

```
gacgcgacug aaugaaaugg ugaaggacgg guccagcacg aggggaaac cccggacaau    60 cagacacggu ucuuguugag uagaguguga gcuccguaac uagucgcguc              110
```

<210> SEQ ID NO 31
<211> LENGTH: 108
<212> TYPE: RNA
<213> ORGANISM: Artificial
<220> FEATURE:
<223> OTHER INFORMATION: weak ADP sensor

<400> SEQUENCE: 31

```
gacgcgacug aaugaaaugg ugaaggacgg guccagccga gggggaaacc ccggacaauc   60
agacacgguc uuguuagagua gagugugagc uccguaacua gucgcguc               108
```

<210> SEQ ID NO 32
<211> LENGTH: 116
<212> TYPE: RNA
<213> ORGANISM: Artificial
<220> FEATURE:
<223> OTHER INFORMATION: SAM sensor

<400> SEQUENCE: 32

```
gacgcgacug aaugaaaugg ugaaggacgg guccacgaaa ggauggcgga aacgccagau   60
gccuuguaac cgaaagggguu guugaguaga gugugagcuc cguaacuagu cgcguc      116
```

<210> SEQ ID NO 33
<211> LENGTH: 118
<212> TYPE: RNA
<213> ORGANISM: Artificial
<220> FEATURE:
<223> OTHER INFORMATION: SAM sensor

<400> SEQUENCE: 33

```
gacgcgacug aaugaaaugg ugaaggacgg guccagcgaa aggauggcgg aaacgccaga   60
ugccuuguaa ccgaaagggc uuguugagua gagugugagc uccguaacua gucgcguc     118
```

<210> SEQ ID NO 34
<211> LENGTH: 118
<212> TYPE: RNA
<213> ORGANISM: Artificial
<220> FEATURE:
<223> OTHER INFORMATION: SAM sensor

<400> SEQUENCE: 34

```
gacgcgacug aaugaaaugg ugaaggacgg guccaccgaa aggauggcgg aaacgccaga   60
ugccuuguaa ccgaaagggg uuguugagua gagugugagc uccguaacua gucgcguc     118
```

<210> SEQ ID NO 35
<211> LENGTH: 120
<212> TYPE: RNA
<213> ORGANISM: Artificial

```
<220> FEATURE:
<223> OTHER INFORMATION: weak SAM sensor

<400> SEQUENCE: 35
gacgcgacug aaugaaaugg ugaaggacgg guccagccga aaggauggcg gaaacgccag    60
augccuugua accgaaaggg gcuuguugag uagaguguga gcuccguaac uagucgcguc   120

<210> SEQ ID NO 36
<211> LENGTH: 120
<212> TYPE: RNA
<213> ORGANISM: Artificial
<220> FEATURE:
<223> OTHER INFORMATION: weak SAM sensor

<400> SEQUENCE: 36
gacgcgacug aaugaaaugg ugaaggacgg guccacccga aaggauggcg gaaacgccag    60
augccuugua accgaaaggg gguuguugag uagaguguga gcuccguaac uagucgcguc   120

<210> SEQ ID NO 37
<211> LENGTH: 122
<212> TYPE: RNA
<213> ORGANISM: Artificial
<220> FEATURE:
<223> OTHER INFORMATION: weak SAM sensor

<400> SEQUENCE: 37
gacgcgacug aaugaaaugg ugaaggacgg guccagcccg aaaggauggc ggaaacgcca    60
gaugccuugu aaccgaaagg gggcuuguug aguagagugu gagcuccgua acuagucgcg   120
uc                                                                 122

<210> SEQ ID NO 38
<211> LENGTH: 124
<212> TYPE: RNA
<213> ORGANISM: Artificial
<220> FEATURE:
<223> OTHER INFORMATION: weak SAM sensor

<400> SEQUENCE: 38
gacgcgacug aaugaaaugg ugaaggacgg guccaguguc gaaaggaugg cggaaacgcc    60
agaugccuug uaaccgaaag ggguugcuugu ugaguagagu gugagcuccg uaacuagucg   120
cguc                                                               124

<210> SEQ ID NO 39
<211> LENGTH: 128
<212> TYPE: RNA
<213> ORGANISM: Artificial
<220> FEATURE:
<223> OTHER INFORMATION: weak SAM sensor

<400> SEQUENCE: 39
gacgcgacug aaugaaaugg ugaaggacgg guccagugug ucgaaaggau ggcggaaacg    60
ccagaugccu uguaaccgaa aggggugugc uuguugagua gagugugagc uccguaacua   120
gucgcguc                                                           128

<210> SEQ ID NO 40
<211> LENGTH: 124
<212> TYPE: RNA
<213> ORGANISM: Artificial
<220> FEATURE:
<223> OTHER INFORMATION: weak SAM sensor
```

```
<400> SEQUENCE: 40
gacgcgacug aaugaaaugg ugaaggacgg guccaguauc gaaaggaugg cggaaacgcc    60
agaugccuug uaaccgaaag ggauacuugu ugaguagagu gugagcuccg uaacuagucg   120
cguc                                                                124

<210> SEQ ID NO 41
<211> LENGTH: 128
<212> TYPE: RNA
<213> ORGANISM: Artificial
<220> FEATURE:
<223> OTHER INFORMATION: weak SAM sensor

<400> SEQUENCE: 41
gacgcgacug aaugaaaugg ugaaggacgg guccaguaua ucgaaaggau ggcggaaacg    60
ccagaugccu uguaaccgaa agggauauac uuguugagua gagugugagc uccguaacua   120
gucgcguc                                                            128

<210> SEQ ID NO 42
<211> LENGTH: 130
<212> TYPE: RNA
<213> ORGANISM: Artificial
<220> FEATURE:
<223> OTHER INFORMATION: guanine "turn-on" sensor

<400> SEQUENCE: 42
gacgcgacug aaugaaaugg ugaaggacgg guccagauaa ucgcguggau auggcacgca    60
aguuucuacc gggcaccgua aauguccgac ucuuguugag uagaguguga gcuccguaac   120
uagucgcguc                                                          130

<210> SEQ ID NO 43
<211> LENGTH: 97
<212> TYPE: RNA
<213> ORGANISM: Artificial
<220> FEATURE:
<223> OTHER INFORMATION: GTP "turn-on" sensor

<400> SEQUENCE: 43
gacgcgacug aaugaaaugg ugaaggacgg guccagcaga agagcacgua uacgcaagcu    60
uguugaguag agugugagcu ccguaacuag ucgcguc                             97

<210> SEQ ID NO 44
<211> LENGTH: 120
<212> TYPE: RNA
<213> ORGANISM: Artificial
<220> FEATURE:
<223> OTHER INFORMATION: streptavidin "turn-on" sensor

<400> SEQUENCE: 44
gacgcgacug aaugaaaugg ugaaggacgg guccacgacc gaccagaauc augcaagugc    60
guaagauagu cgcgggccgg gguuguugag uagaguguga gcuccguaac uagucgcguc   120

<210> SEQ ID NO 45
<211> LENGTH: 21
<212> TYPE: DNA
<213> ORGANISM: Artificial
<220> FEATURE:
<223> OTHER INFORMATION: tether sequence

<400> SEQUENCE: 45
ggttgtaagt tttaggttgc c                                              21
```

```
<210> SEQ ID NO 46
<211> LENGTH: 12
<212> TYPE: DNA
<213> ORGANISM: Artificial
<220> FEATURE:
<223> OTHER INFORMATION: fixed sequence for DFHBI library

<400> SEQUENCE: 46
ctgccgaagc ag                                                             12

<210> SEQ ID NO 47
<211> LENGTH: 40
<212> TYPE: DNA
<213> ORGANISM: Artificial
<220> FEATURE:
<223> OTHER INFORMATION: 5' primer sequence with T7 promoter

<400> SEQUENCE: 47
gtataatacg actcactata gggagacgca actgaatgaa                               40

<210> SEQ ID NO 48
<211> LENGTH: 20
<212> TYPE: DNA
<213> ORGANISM: Artificial
<220> FEATURE:
<223> OTHER INFORMATION: 3' primer sequence

<400> SEQUENCE: 48
gtgacgcgac tagttacgga                                                     20

<210> SEQ ID NO 49
<211> LENGTH: 46
<212> TYPE: DNA
<213> ORGANISM: Artificial
<220> FEATURE:
<223> OTHER INFORMATION: 5' primer sequence with T7 promoter

<400> SEQUENCE: 49
cagtcaagat ctcgatcccg cgaaattaat acgactcact ataggg                        46

<210> SEQ ID NO 50
<211> LENGTH: 59
<212> TYPE: DNA
<213> ORGANISM: Artificial
<220> FEATURE:
<223> OTHER INFORMATION: 3' primer sequence

<400> SEQUENCE: 50
catcagctcg agcaaaaaac ccctcaagac ccgtttagag gccccaaggg gttatgcta          59

<210> SEQ ID NO 51
<211> LENGTH: 104
<212> TYPE: RNA
<213> ORGANISM: Artificial
<220> FEATURE:
<223> OTHER INFORMATION: aptamer that binds
      4-(3,5-difluoro-4-hydroxybenzylidene)-1-methyl-5-oxo-4,5-dihydro-
      1H-imidazole-2-carbaldehyde oxime

<400> SEQUENCE: 51
gggagacgca acugaaugaa guuggcccau gauagaaagc agggugcugc uucggcaguu         60
gucggagggu gggggauug acuauccgua acuagucgcg ucac                          104

<210> SEQ ID NO 52
```

```
<211> LENGTH: 119
<212> TYPE: RNA
<213> ORGANISM: Artificial
<220> FEATURE:
<223> OTHER INFORMATION: aptamer that binds
      4-(3,5-difluoro-4-hydroxybenzylidene)-1-methyl-5-oxo-4,5-dihydro-
      1H-imidazole-2-carbaldehyde oxime

<400> SEQUENCE: 52
gggcgacuca cuauagggag acgcaacuga augaagcgaa gaaggagguc ugaggagguc      60
acugcuucgg cagugggcg uuuucccugg ggguguugau ccguaacuag ucgcgucac       119

<210> SEQ ID NO 53
<211> LENGTH: 104
<212> TYPE: RNA
<213> ORGANISM: Artificial
<220> FEATURE:
<223> OTHER INFORMATION: aptamer that binds
      4-(3,5-difluoro-4-hydroxybenzylidene)-1-methyl-5-oxo-4,5-dihydro-
      1H-imidazole-2-carbaldehyde oxime

<400> SEQUENCE: 53
gggagacgca acugaaugaa agaccugacg agggugaagc gguugucugc uucggcagca      60
uugaaagggu gggguguagg augguccgua acuagucgcg ucac                     104

<210> SEQ ID NO 54
<211> LENGTH: 104
<212> TYPE: RNA
<213> ORGANISM: Artificial
<220> FEATURE:
<223> OTHER INFORMATION: aptamer that binds
      4-(3,5-difluoro-4-hydroxybenzylidene)-1-methyl-5-oxo-4,5-dihydro-
      1H-imidazole-2-carbaldehyde oxime

<400> SEQUENCE: 54
gggagacgca acugaaugaa gcgaggaagg aggucugagg aggucacugc uucgacagug      60
gggcguuuuc ccuggggug uugauccgua acuagucgcg ucac                      104

<210> SEQ ID NO 55
<211> LENGTH: 104
<212> TYPE: RNA
<213> ORGANISM: Artificial
<220> FEATURE:
<223> OTHER INFORMATION: aptamer that binds
      4-(3-fluoro-4-hydroxy-5-methoxybenzylidene)-1-methyl-5-oxo-4,5-di
      hydro-1H-imidazole-2-carbaldehyde oxime

<400> SEQUENCE: 55
gggagacgca acugaaugaa gcgaggaagg aggucugagg aggucacugc uucgacagug      60
gggcguuuuc ccuggggug uugauccgua acuagucgcg ucac                      104

<210> SEQ ID NO 56
<211> LENGTH: 104
<212> TYPE: RNA
<213> ORGANISM: Artificial
<220> FEATURE:
<223> OTHER INFORMATION: aptamer that binds
      4-(3-fluoro-4-hydroxy-5-methoxybenzylidene)-1-methyl-5-oxo-4,5-di
      hydro-1H-imidazole-2-carbaldehyde oxime

<400> SEQUENCE: 56
gggagacgca acugaaugaa ugaguaugau gcacgguuaa aauccacugc uucggcagga      60
guugcguuag gagggucggg agucuccgua acuagucgcg ucac                     104
```

```
<210> SEQ ID NO 57
<211> LENGTH: 104
<212> TYPE: RNA
<213> ORGANISM: Artificial
<220> FEATURE:
<223> OTHER INFORMATION: aptamer that binds methyl
     3-((Z)-4-(3,5-difluoro-4-hydroxybenzylidene)-1-methyl-5-oxo-4,5-d
     ihydro-1H-imidazol-2-yl)acrylate

<400> SEQUENCE: 57
gggagacgca acugaaugaa agaccugacg agggugaagc gguugucugc uucggcagca      60
uugaaagggu gggguguagg augguccgua acuagucgcg ucac                      104

<210> SEQ ID NO 58
<211> LENGTH: 104
<212> TYPE: RNA
<213> ORGANISM: Artificial
<220> FEATURE:
<223> OTHER INFORMATION: aptamer that binds methyl
     3-((Z)-4-(3,5-difluoro-4-hydroxybenzylidene)-1-methyl-5-oxo-4,5-d
     ihydro-1H-imidazol-2-yl)acrylate

<400> SEQUENCE: 58
gggagacgca acugaaugaa gccuccgugc gacaucaugc gcgcgacugc uucggcagag      60 gugggugguguggaggagua ucuguccgua acuagucgcg ucac                       104

<210> SEQ ID NO 59
<211> LENGTH: 104
<212> TYPE: RNA
<213> ORGANISM: Artificial
<220> FEATURE:
<223> OTHER INFORMATION: aptamer that binds
     4-(3,5-difluoro-4-hydroxybenzylidene)-1-methyl-2-((E)-2-nitroviny
     l)-1H-imidazol-5(4H)-one

<400> SEQUENCE: 59
gggagacgca acugaaugaa auacuuggga ugguaauggc cuggagcugc uucggcagac      60
ccgugcaagg acgugggaga ggguccgua acuagucgcg ucac                       104
```

METHODS FOR RNA DETECTION AND QUANTIFICATION

This application is a national stage application under 35 U.S.C. 371 from PCT/US2012/048701, filed Jul. 27, 2012, which claims the benefit of U.S. Provisional Patent Application Ser. No. 61/512,310, filed Jul. 27, 2011, and U.S. Provisional Patent Application Ser. No. 61/606,254, filed Mar. 2, 2012, each which is hereby incorporated by reference in its entirety.

This invention was made with government support under grant numbers R01 NS064516-03 and R01 EB0102049 awarded by the National Institutes of Health. The government has certain rights in the invention.

FIELD OF THE INVENTION

The present invention relates nucleic acid molecules (aptamers) that bind specifically to small molecule fluorophores, molecular complexes containing the aptamers and fluorophores, and their use for in vitro or in vivo monitoring of the activity, trafficking or localization, degradation, or quantification of various molecules. The present invention also relates to methods and uses for such complexes, as well as kits for practicing those methods.

BACKGROUND OF THE INVENTION

RNA used to be considered a simple and straightforward molecule in cells. The three major classes of RNA, i.e., transfer RNA, ribosomal RNA, and messenger RNA (mRNA), have generally not been thought to be subjected to regulation by signaling pathways, or to have major roles in disease processes. However, a rapidly emerging concept over the past few years is that transcription and other cell signaling pathways are regulated by a diverse array of noncoding RNAs, such as microRNAs, termini-associated RNAs (Han et al., "Promoter-associated RNA Is Required for RNA-directed Transcriptional Gene Silencing in Human Cells," *Proc Natl Acad Sci USA* 104:12422-12427 (2007)), and other noncoding RNAs. Additionally, mRNA is no longer viewed as a simple intermediate between DNA and protein, but instead is now known to be subjected to wide range of post-transcriptional processing events, including diverse types of splicing reactions, nonsense-mediated decay, RNA editing, exo- and endonucleolytic degradation, polyadenylation, and deadenylation. Another intriguing aspect of RNA biology is the finding that trinucleotide repeat-containing mRNAs exert specific gain-of-function toxicities associated with their accumulation at certain intracellular sites (Ranum et al., "Myotonic Dystrophy: RNA Pathogenesis Comes Into Focus," *Am. J. Hum. Genet.* 74:793 (2004)). In addition to these different regulatory pathways, recent studies indicate that RNAs traffic through different parts of the cell during RNA maturation. For example, nascent RNA transcripts are likely trafficked to specific intracellular sites in the nucleus for processing events, such as splicing, nonsense-mediated decay, or for packaging into transport granules. After nuclear export, some RNAs have been localized to RNA-enriched intracellular structures including RNA granules, stress granules, and processing bodies (P-bodies) (Kiebler et al., "Neuronal RNA Granules: Movers and Makers," *Neuron* 51:685-690 (2006)). The diversity of these RNA regulatory mechanisms makes it clear that RNA is regulated by a complex and intricate network of regulatory mechanisms and intracellular structures that have a critical role in gene expression.

RNA is increasingly being utilized for various biotechnology applications, including as sensors (Breaker, "Engineered Allosteric Ribozymes as Biosensor Components," *Curr Opin Biotech.* 13:31 (2002); Cho et al., "Applications of Aptamers as Sensors," *Annu Rev Anal Chem.* 2:241 (2009)), nanodevices (Sherman and Seeman, "Design of Minimally Strained Nucleic Acid Nanotubes," *Biophys. J.* 90:4546 (2006); Win et al., "Frameworks for Programming Biological Function through RNA Parts and Devices," *Chem. Biol.* 16:298 (2009)), catalysts (Joyce, "Directed Evolution of Nucleic Acid Enzymes," *Annu. Rev. Biochem.* 73: 791 (2004); Lincoln and Joyce, "Self-sustained Replication of an RNA Enzyme," *Science* 323:1229 (2009)), protein inhibitors (Lee et al., "Aptamer Therapeutics Advance," *Curr. Opin. Chem. Biol.* 10:282 (2006)), and in the development of supramolecular structures (Chworos et al., "Building Programmable Jigsaw Puzzles with RNA," *Science* 306:2068 (2004); Dirks et al., "Paradigms for Computational Nucleic Acid Design," *Nucleic Acids Res.* 32:1392 (2004); Levy-Nissenbaum et al., "Nanotechnology and Aptamers: Applications in Drug Delivery," *Trends Biotechnol.* 26:442 (2008)). The ability to confer GFP-like functionality to RNA will facilitate molecular studies of RNA and advance various RNA-based applications.

Although PCT Application Publ. No. WO/2010/096584 to Jaffrey and Paige describes a number of RNA aptamers that bind to conditionally fluorescent molecules derived from the chromophore of green fluorescent protein, and their use, for example, in cellular imaging and RNA trafficking, there continues to be a need for improved aptamers and aptamer-fluorophore complexes to enhance the generation of aptamer-based small molecule sensors as well as in vitro and in vivo monitoring of RNA molecules.

The present invention is directed to overcoming these and other deficiencies in the art.

SUMMARY OF THE INVENTION

A first aspect of the invention relates to a nucleic acid molecule that includes a first domain that binds specifically to a fluorophore according to the first aspect of the invention, wherein binding of the nucleic acid molecule to the fluorophore substantially enhances fluorescence of the fluorophore upon exposure to radiation of suitable wavelength. This nucleic acid molecule includes RNA, DNA, and/or modified nucleic acids.

In a preferred embodiment, the nucleic acid molecule comprises the nucleotide sequence of SEQ ID NO: 1, 2, or 3, or a portion thereof sufficient to allow for binding to the fluorophore molecule to induce fluorescence thereof. The fluorophore is preferably 4-(3,5-difluoro-4-hydroxybenzylidene)-1,2-dimethyl-imidazol-5-one ("DFHBI").

A second aspect of the invention relates to a fusion RNA molecule that includes an RNA molecule according to the first aspect of the invention. By way of example, the fused RNA molecule can be a hybridization probe, another RNA aptamer, or a non-aptamer RNA molecule that binds to a protein of interest.

A third aspect of the invention relates to a nucleic acid molecule according to the first aspect of the invention, which also includes an analyte-binding domain that comprises a nucleotide sequence that adopts a conformation to allow the second domain to bind specifically to an analyte. According to one embodiment, the first domain binds to the fluorophore only after the second domain binds to the analyte.

A fourth aspect of the present invention relates to a detection array that includes a plurality of nucleic acid molecules according to the first or second aspect of the invention each tethered to a discrete location on a surface of the array.

An fifth aspect of the invention relates to a molecular complex that includes a nucleic acid molecule according to the first or second aspect of the invention and a fluorophore molecule specifically bound to the nucleic acid molecule, wherein the fluorophore has substantially enhanced fluorescence (in comparison to the fluorophore prior to specific binding) upon exposure to radiation of suitable wavelength.

A sixth aspect of the invention relates to a molecular complex that includes a nucleic acid molecule according to the third aspect of the invention, a fluorophore molecule specifically bound to the nucleic acid molecule, and an analyte specifically bound to the nucleic acid molecule, wherein the fluorophore has substantially enhanced fluorescence (in comparison to the fluorophore prior to specific binding) upon exposure to radiation of suitable wavelength.

A seventh aspect of the invention relates to a host cell or organism that includes a molecular complex according to the fifth or sixth aspects of the invention.

An eighth aspect of the invention relates to a kit that includes a fluorophore that contains a methyne bridge between a substituted aromatic ring system and a substituted imidazol(thi)one, oxazol(thi)one, pyrrolin(thi)one, or furan(thi)one ring, and a nucleic acid molecule according to the first, second, or third aspects of the invention.

A ninth aspect of the invention relates to a DNA construct that includes a first region that encodes an RNA molecule according to the first, second, or third aspects of the invention. The constructed DNA molecule can be in the form of an isolated transgene or an expression vector that includes appropriate regulatory sequences to allow for expression of the encoded RNA molecules.

A tenth aspect of the invention relates to a DNA construct of the ninth aspect of the invention, which includes an intron positioned within the first region, whereby the excision of the intron from a transcript of the constructed DNA molecule affords the RNA molecule. The constructed DNA molecule can be in the form of an isolated transgene or an expression vector (i.e., that include appropriate regulatory sequences to allow for expression of the encoded RNA molecules).

An eleventh aspect of the invention relates to a DNA construct that includes a first region that encodes an RNA molecule according to the first or second aspects of the invention and a second region that is linked to the first region, the second region encoding an RNA transcript of interest, whereby transcription of the constructed DNA molecule forms an RNA molecule that includes the RNA transcript of interest joined to the RNA molecule that binds specifically to a fluorophore. The constructed DNA molecule can be in the form of an isolated transgene or an expression vector (i.e., that include appropriate regulatory sequences to allow for expression of the encoded RNA molecules).

A twelfth aspect of the invention relates to a transgenic host cell that includes a DNA construct according to the ninth, tenth, or eleventh aspects of the invention.

A thirteenth aspect of the invention relates to an empty genetic construct that can be used to prepare a DNA construct according to the eleventh aspect of the invention. The genetic construct includes a promoter sequence operably linked to a first DNA sequence that encodes an RNA molecule according to the first or second aspect of the invention and a second DNA sequence that contains one or more enzymatic cleavage sites. This aspect of the invention also includes kits that contain the empty genetic construction, and which can be used to prepare the DNA construct according to the thirteenth aspect of the invention.

A fourteenth aspect of the invention relates to a method of detecting a target molecule that includes: first exposing a nucleic acid molecule according to the third aspect of the invention (where the first domain binds to the fluorophore only after the second domain binds to the target molecule) to a medium suspected to contain the target molecule under conditions effective to allow the second domain to bind specifically to the target molecule, if present; and second exposing the nucleic acid molecule and medium to a fluorophore comprising a methyne bridge between a substituted aromatic ring system and a substituted imidazol(thi)one, oxazol(thi)one, pyrrolin(thi)one, or furan(thi)one ring under conditions effective to allow the first domain to bind specifically to the fluorophore after binding of the target molecule by the second domain, thereby inducing the fluorophore to adopt a conformation that exhibits enhanced fluorescent emissions; and exciting the fluorophore with radiation of appropriate wavelength and detecting fluorescence by the fluorophore, whereby the detection of fluorescence emissions by the fluorophore indicates binding of the nucleic acid molecule to the target molecule.

A fifteenth aspect of the invention relates to a method of determining location of a target molecule that includes: forming a molecular complex according to the fifth or sixth aspects of the invention; exciting the fluorophore with radiation of appropriate wavelength; and detecting fluorescence by the fluorophore, whereby fluorescence by the fluorophore identifies presence of the target molecule.

A sixteenth aspect of the invention relates to a method of measuring transcription by a promoter of interest in a cell, where the method includes: introducing into a cell a DNA construct according to the ninth aspect of the invention; introducing into the cell a fluorophore in a substantially non-fluorescent form; introducing an agent that modulates transcription of the DNA construct into the cell; and detecting fluorescence by the fluorophore within the cell, whereby the level of fluorescence correlates with the level of transcription for the DNA construct and the effect of the agent in modulating the level of transcription.

A seventeenth aspect of the invention relates to a method of measuring transcription by a promoter of interest, where the method includes: introducing into a cell a DNA construct according to the ninth aspect of the invention and an agent that modulates transcription of the DNA construct; recovering RNA transcripts from the cell; introducing a fluorophore in a substantially non-fluorescent form to the recovered RNA transcripts; and detecting fluorescence by the fluorophore, whereby the level of fluorescence correlates with the level of transcription by the DNA construct and the effect of the agent in modulating the level of transcription.

An eighteenth aspect of the invention relates to a method of monitoring RNA that includes: introducing into a cell a first DNA construct according to the eleventh aspect of the invention; and introducing into the cell a first fluorophore having a methyne bridge between a substituted aromatic ring system and a substituted imidazol(thi)one, oxazol(thi)one, pyrrolin(thi)one, or furan(thi)one ring, wherein the first fluorophore is bound specifically by the first domain of the RNA molecule encoded by the DNA construct to enhance fluorescence emissions by the first fluorophore; exposing the cell to radiation of a wavelength suitable to induce fluorescence emissions by the first fluorophore that is bound by the first domain or a FRET partner; and measuring the fluorescent emissions of the first fluorophore or the FRET partner to monitor the RNA transcript. This aspect is particularly useful for monitoring the location, degradation (over time), and for quantitating the RNA transcript (i.e., based on the level of fluorescence). Moreover, simultaneous monitoring of two or more RNA transcripts is possible.

A nineteenth aspect of the invention relates to a method of monitoring a target molecule in a cell that includes: introducing into a cell a nucleic acid molecule according to the third aspect of the invention (where the first domain binds to the fluorophore only after the second domain binds to the target molecule), wherein the second domain binds the target molecule; introducing into the cell a first fluorophore having a methyne bridge between a substituted aromatic ring system and a substituted imidazol(thi)one, oxazol(thi)one, pyrrolin(thi)one, or furan(thi)one ring, wherein the first fluorophore is bound specifically by the first domain of the nucleic acid molecule to enhance fluorescence emissions by the first fluorophore; exposing the cell to radiation of a wavelength suitable to induce fluorescence emissions by the first fluorophore that is bound by the nucleic acid molecule or a FRET partner; and measuring the fluorescent emissions of the first fluorophore or the FRET partner to monitor the target molecule. This aspect is particularly useful for monitoring the location, degradation (over time), and for quantitating the target molecule (i.e., based on the level of fluorescence). Moreover, simultaneous monitoring of two or more target molecules is possible.

A twentieth aspect of the invention relates to a method of monitoring a target molecule in a cell that includes: introducing into a cell a gene encoding the nucleic acid molecule according to the third aspect of the invention (where the first domain binds to the fluorophore only after the second domain binds to the target molecule), wherein the second domain binds the target molecule; introducing into the cell a first fluorophore having a methyne bridge between a substituted aromatic ring system and a substituted imidazol (thi)one, oxazol(thi)one, pyrrolin(thi)one, or furan(thi)one ring, wherein the first fluorophore is bound specifically by the first domain of the nucleic acid molecule to enhance fluorescence emissions by the first fluorophore; exposing the cell to radiation of a wavelength suitable to induce fluorescence emissions by the first fluorophore that is bound by the nucleic acid molecule or a FRET partner; and measuring the fluorescent emissions of the first fluorophore or the FRET partner to monitor the target molecule. This aspect is particularly useful for monitoring the location, degradation (over time), and for quantitating the target molecule (i.e., based on the level of fluorescence). Moreover, simultaneous monitoring of two or more target molecules is possible.

A twenty-first aspect of the invention relates to a method of screening an agent that modifies gene expression, which includes: introducing a transgene into a cell under conditions suitable to cause transcription of the gene, the transcript comprising an RNA molecule according to the second aspect of the invention; exposing the cell to an agent; introducing into the cell a fluorophore having a methyne bridge between a substituted aromatic ring system and a substituted imidazol (thi)one, oxazol(thi)one, pyrrolin(thi)one, or furan(thi)one ring, wherein the fluorophore is bound specifically by the first domain of the RNA molecule to enhance fluorescence emissions by the fluorophore; exposing the cell to radiation of a wavelength suitable to induce fluorescence emissions by the fluorophore that is bound by the RNA molecule or a FRET partner; and measuring the fluorescent emissions of the fluorophore or the FRET partner, whereby a reduction or absence of fluorescent emissions, relative to an otherwise identical control cell that is not exposed to the agent, indicates that the agent inhibits expression of the transgene, and an increase of fluorescent emissions, relative to an otherwise identical control cell that is not exposed to the agent, indicates that the agent increases expression of the transgene.

A twenty-second aspect of the invention relates to a method of screening an agent that modifies RNA splicing, which includes: introducing into a cell a transgene comprising a DNA construct according to the tenth aspect of the invention, wherein transcription of the transgene affords a transcript comprising an intron positioned between first and second portions of the RNA molecule; exposing the cell to an agent; introducing into the cell a fluorophore having a methyne bridge between a substituted aromatic ring system and a substituted imidazol(thi)one, oxazol(thi)one, pyrrolin (thi)one, or furan(thi)one ring, wherein the fluorophore is bound specifically by the first domain of the RNA molecule to enhance fluorescence emissions by the fluorophore; exposing the cell to radiation of a wavelength suitable to induce fluorescence emissions by the fluorophore that is bound by the RNA molecule or a FRET partner; and measuring the fluorescent emissions of the fluorophore or the FRET partner, whereby a reduction or absence of fluorescent emissions, relative to an otherwise identical control cell that is not exposed to the agent, indicates that the agent inhibits proper splicing of the transcript; and an increase of fluorescent emissions, relative to the otherwise identical control cell that is not exposed to the agent, indicates that the agent promotes proper splicing of the transcript.

A twenty-third aspect of the invention relates to method of screening an agent that modifies RNA splicing, which includes: providing a medium comprising an RNA transcript, a spliceosome comprising a splicing enzyme, an agent, and a fluorophore, wherein the RNA transcript comprises first and second exons having an intervening intron region, the first and second exons, upon excision of the intron, forming an RNA molecule according to the second aspect of the invention, wherein the fluorophore has a methyne bridge between a substituted aromatic ring system and a substituted imidazol(thi)one, oxazol(thi)one, pyrrolin (thi)one, or furan(thi)one ring, and wherein the fluorophore is bound specifically by the first domain of the RNA molecule to enhance fluorescence emissions by the fluorophore; exposing the medium to radiation of a wavelength suitable to induce fluorescence emissions by the fluorophore that is bound by the RNA molecule or a FRET partner; and measuring the fluorescent emissions of the fluorophore or the FRET partner, whereby a reduction or absence of fluorescent emissions, relative to an otherwise identical medium that lacks the agent, indicates that the agent inhibits proper splicing of the transcript; and an increase of fluorescent emissions, relative to the otherwise identical medium that lacks the agent indicates that the agent promotes proper splicing of the transcript.

A twenty-fourth aspect of the invention relates to a method of screening an agent for activity against a target molecule. The method includes the steps of introducing into a cell a nucleic acid molecule according to the third aspect of the invention (where the first domain binds to the fluorophore only after the second domain binds to the target molecule), wherein the second domain binds a target molecule; introducing into the cell a first fluorophore comprising a methyne bridge between a substituted aromatic ring system and a substituted imidazol(thi)one, oxazol(thi)one, pyrrolin(thi)one, or furan(thi)one ring, wherein the first fluorophore is bound specifically by the first domain of the nucleic acid molecule to enhance fluorescence emissions by the first fluorophore; exposing the cell to radiation of a wavelength suitable to induce fluorescence emissions by the first fluorophore that is bound by the nucleic acid molecule or a FRET partner; and measuring the fluorescent emissions of the first fluorophore or the FRET partner, wherein the a difference in the fluorescent emissions by the fluorophore or FRET partner, relative to an otherwise identical cell that lacks the agent, indicates that the agent modifies the activity of the target molecule.

A twenty-fifth aspect of the invention relates to a method of identifying nucleic acid molecules capable of binding to a target molecule, which method includes: providing a pool of nucleic acid molecules that each comprise a first domain comprising a nucleic acid molecule according to the first aspect of the invention, which binds specifically to a fluorophore having a methyne bridge between a substituted aromatic ring system and a substituted imidazol(thi)one, oxazol(thi)one, pyrrolin(thi)one, or furan(thi)one ring, and a second domain that comprises a random sequence, and only after binding of the second domain to the target molecule is first domain capable of binding specifically to the fluorophore; exposing the pool of nucleic acid molecule to a target molecule and the fluorophore, whereby fluorescence emissions by the fluorophore are enhanced by the binding of the first domain to the fluorophore; illuminating the fluorophore with light of a wavelength suitable to induce fluorescence emissions by the fluorophore that is bound by the first domain molecule; and measuring the fluorescent emissions of the fluorophore, whereby detection of fluorescence by the fluorophore indicates that the second domain of the nucleic acid molecule binds to the target molecule.

Additional aspects of the invention include new fluorophores according to formula I and new nucleic acid aptamers that bind to these fluorophores to induce their fluorescence, and the use thereof these to form molecular complexes. The use of these materials and genetic constructs encoding the aptamers is also contemplated here, including all of the methods described herein.

The examples of the present invention demonstrate the development of improved nucleic acid molecules that bind to the fluorophore 4-(3,5-difluoro-4-hydroxybenzylidene)-1,2-dimethyl-imidazol-5-one ("DFHBI"), allowing DFHBI to be "switched on" only when bound specifically by the aptamer. This solves the problem of many prior art fluorophores, which contribute indiscriminately to background fluorescence. The aptamer/fluorophore complexes of the invention are useful for a wide variety of purposes, both in vitro and in vivo, including monitoring the location or degradation of RNA molecules in vivo, monitoring and quantifying the amount of a target molecule in an in vitro or in vivo system. Importantly, the fluorophores are non-toxic, unlike many prior art dyes. The detection procedures can be implemented using existing optical detection devices and is amenable to high-throughput microarrays or drug screening. Moreover, the generation of RNA-based small molecule sensors demonstrates that it is possible to vastly increase the number molecules that can be detected in cells beyond what is possible using current protein-based FRET sensors. The present invention has devised simple strategies to develop sensors for important signaling molecules that can be used in live cell imaging. This was not previously possible using protein-based FRET-based sensors. Thus, the present invention provides a rapid, simple, and general approach to obtain sensors for any small molecule. These sensors should immediately find use as simple fluorometric reagents to measure small molecules, thereby simplifying assays, and permitting high-throughput fluorescence-based screens.

BRIEF DESCRIPTION OF THE DRAWINGS

FIG. 1 is an alignment of several RNA molecules selected for or tested for capability to bind to the fluorophore 4-(3,5-difluoro-4-hydroxybenzylidene)-1,2-dimethyl-imidazol-5-one ("DFHBI") to induce its fluorescence. SEQ ID NO: 1 represents a consensus sequence based on SEQ ID NO: 5-15; and SEQ ID NO: 4 represents a prior art sequence identified in PCT Application Publ. No. WO 2010/096584, which is hereby incorporated by reference in its entirety. SEQ ID NO: 4 is excluded from the scope of the consensus of SEQ ID NO: 1.

FIG. 2A shows the normalized excitation (left curve) and emission (right curve) spectra of the 24-2 (SEQ ID NO:5)-DFHBI complex. The excitation peak for 24-2-DFHBI is markedly red-shifted compared to RNAs that activate DMHBI, consistent with the phenolate form of DFHBI being the excited species in this complex. FIG. 2B illustrates the normalized absorbance spectra of DFHBI at pHs 5.0, 6.0, 7.0 and 8.0. A shift in the spectra from phenolate to phenolic DFHBI absorbance was observed for pH values below 7.0. The peak detected at ~370 nm at pH 5 and 6 is due to phenolic DFHBI absorbance, whereas the peak at ~425 nm is due to phenolate DFHBI absorbance. FIGS. 2C-D illustrate the fluorescence of 24-2 (SEQ ID NO:5)-DFHBI (2C) or 24-2 (SEQ ID NO:5)-HBI (2D) molecular complexes at pHs 6.0, 7.0, and 8.0. 24-2 is capable of eliciting fluorescence at pHs where fluorophores are primarily in the phenolate form, but elicits reduced fluorescence at pHs when fluorophores are in the phenolic form. Reduced 24-2-DFHBI fluorescence was observed with pH values below 7.0 (2C), conditions under which the phenolic DFHBI form begins to accumulate (2A). For HBI, which is predominantly phenolic at pH values below 8.0 as opposed to 7.0, fluorescence due to 24-2 was dramatically reduced from pH 8.0 to pH 7.0. This indicates that 24-2-DFHBI complexes are composed exclusively of phenolate DFHBI, analogous to the EGFP chromophore being exclusively in the phenolate form. FIG. 2E illustrates photobleaching curves for 24-2-DFHBI, EGFP and fluorescein. Fluorophores were immobilized on glass slides and illuminated continuously with a 130 W mercury lamp. Total fluorescence was then plotted against exposure time and normalized to the maximum intensity of each fluorophore. Both fluorescein and EGFP photobleached while 24-2-DFHBI complexes were resistant to photobleaching even after 45 min of continuous illumination.

In FIG. 3A, bases that could be removed without significant loss in fluorescence are indicated in purple, which includes several bases from the largest loop and largest stem. A-U, G-U and any mismatched base pairs were mutated to G-C base pairs and tested for their effect on 24-2 fluorescence. G-C mutations that reduced 24-2 fluorescence are indicated in red, those which had no effect are indicated by asterisk (*), and those which increased the fluorescence of 24-2 are indicated in green. Base substitutions indicated by an asterisk (*) helped to validate structural predictions because substituting one base pair for another (e.g. A-U for G-C) had negligible effect or increased fluorescence. The hairpin loop motifs CGGG and UUCG were swapped with the sequence UUCG or GAAA, respectively. Both swaps resulted in significantly reduced fluorescence signal suggesting that they are important for DFHBI binding. The final truncated 24-2 sequence, 24-2-min, is shown in FIG. 3B and exhibits ~95% of full-length 24-2 fluorescence.

FIG. 6 is a pair of graphs that quantify the effect of sucrose on the levels of 5S in the nucleus and cytoplasm, as measured over time by the fluorescence intensity of Spinach signal in the nucleus and cytoplasm of 5S-Spinach expressing cells. HEK293T cells were pretreated with the RNA Pol III inhibitor ML-60128 (30 nM) for 16 h to abolish baseline expression of 5S-Spinach. The media was then exchanged with fresh media containing either vehicle or 600 mM sucrose and newly synthesized 5S-Spinach was imaged over 60 min. Cells exposed to sucrose exhibit rapid and elevated induction of 5S transcription compared to untreated cells. Additionally, while nuclear and cytoplasmic levels of 5S-Spinach were comparable throughout the time-course in vehicle-treated cells (upper panel), nuclear levels of 5S-Spinach were substantially higher than cytoplasmic levels in sucrose-treated cells (lower panel). The 5S-Spinach may accumulate in the nucleus due to saturation of the nuclear export machinery in the sucrose-treated cells. Cells per condition per time point, n=3. Error bars represent s.e.m.

FIG. 7A is a schematic illustration of DFHBI binding to Spinach. The Spinach RNA aptamer is capable of binding to and activating the fluorescence of the small molecule fluorophore DFHBI (green circle). In the unbound form, DFHBI is completely non-fluorescent, but becomes robustly fluorescent upon binding to Spinach. DFHBI fluorescence activation by Spinach requires the formation of a duplexed stem in stem-loop 2 (boxed). FIG. 7B illustrates the modular design of Spinach-based sensors. The three modular components of the Spinach-based sensor are depicted. The recognition module constitutes an aptamer that binds to a specific target of interest (i.e., an analyte-binding aptamer). The transducer module is composed of two strands which form a weakly base-paired stem. Folding of the recognition domain provides additional stability that facilitates hybridization of the stem region in the transducer module. The Spinach module binds to and activates the fluorescence of DFHBI, but only when the transducer module forms a stem. FIG. 7C illustrates a model of metabolite-dependent activation of Spinach-based fluorescence. A representation of the Spinach-based sensor is shown on the left. The sensor comprises the Spinach domain (black), the stem-forming transducer module (orange), and the recognition module (blue). In the absence of the target molecule, the transducer module is in a primarily unstructured state, which prevents the stabilization of the Spinach structure needed for activation of DFHBI by the Spinach module. Upon binding of the target molecule to the recognition module, the transducer module forms a duplex, leading to structural rigidification of the Spinach module, and activation of DFHBI fluorescence.

FIG. 8A is graph of the emission spectra of the RNA sensor for adenosine (Ade) in the presence or absence of Ade. Spectra were collected at 0.1 µM RNA, 10 µM DFHBI and 1 mM Ade. Fluorescence signal is negligible in the absence of Ade and increases 16-fold in the presence of Ade. FIG. 8B is graph of the emission spectra of the RNA sensor for ADP in the presence or absence of ADP. Spectra were collected at 0.1 µM RNA, 10 µM DFHBI and 1 mM ADP. Fluorescence signal is negligible in the absence of ADP and increases 18-fold in the presence of ADP. FIG. 8C is graph of the emission spectra of the RNA sensor for SAM in the presence or absence of SAM. Spectra were collected at 0.1 µM RNA, 10 µM DFHBI and 1 mM SAM. Fluorescence signal is negligible in the absence of SAM and increases 24-fold in the presence of SAM. FIG. 8D is graph of the emission spectra of the RNA sensor for guanine (Gua) in the presence or absence of Gua. Spectra were collected at 0.1 µM RNA, 10 µM DFHBI and 100 µM Gua. Fluorescence signal is negligible in the absence of Gua and increases 32-fold in the presence of Gua. FIG. 8E is graph of the emission spectra of the RNA sensor for GTP in the presence or absence of GTP. Spectra were collected at 0.1 µM RNA, 10 µM DFHBI and 1 mM GTP. Fluorescence signal is negligible in the absence of GTP and increases 15-fold in the presence of GTP. FIG. 8F is graph of the dose-response curve for fluorescence detection of ADP by the ADP RNA sensor. Half-maximal fluorescence is reached at 270 µM ADP. FIG. 8G is graph of the dose-response curve for fluorescence detection of SAM by the SAM RNA sensor. Half-maximal fluorescence is reached at 120 µM SAM. FIG. 8H is bar graph illustrating the molecular discrimination of the ADP sensor. The ADP sensor is specific for ADP over other highly similar adenosine-containing nucleotides including ATP, AMP, cAMP and NAD$^+$. The ADP sensor remains selective even at very high concentrations (1 mM) of competing molecules. FIG. 8I is bar graph illustrating the molecular discrimination of the SAM sensor. The SAM sensor shows a high level of molecular discrimination against highly related molecules. SAM precursors methionine and adenosine gave negligible signal above background at 1 mM concentrations. The highly related breakdown product of SAM, SAH, also gave negligible signal even though SAM and SAH differ by only a single methyl group.

In FIG. 9A, is a panel of images showing that Spinach-based ADP sensors can detect changes in endogenous ADP levels in living E. coli cells transformed with plasmids expressing the ADP sensor. The E. coli were grown in media containing glucose and then switched to a media containing a different carbon source. Fluorescence was imaged continuously with an epifluorescence microscope for 180 min. Phase images and fluorescence images at 0 min and 180 min after the media switch are shown. Cells switched from glucose-containing media to glucose (control), glycerol or succinate-containing media showed only a slight increase in ADP levels after 180 min of incubation while cells switched to acetate-containing media show much higher levels of ADP after the 180 min incubation. Cells transformed with a plasmid expressing a control aptamer were not fluorescent under identical imaging conditions. Scale bar, 5 µm. FIG. 9B is a graph illustrating the quantification of fluorescence in cells expressing the ADP sensor after cells are switched from glucose-containing media to media containing different carbon sources. Individual cells were imaged over 3 hr and fluorescence was measured and normalized to the cellular area to quantify the cellular ADP level. Changing from a glucose-containing media to acetate resulted in the largest increases in fluorescence, while switching to other carbon sources produces more subtle increases in fluorescence levels. A total of 150 cells were quantified over three experimental replicates for each condition, and values shown are the average+/−standard error of the mean. FIG. 9C is a graph illustrating the quantification of ADP levels when cells are switched from acetate-containing media to glucose-containing media. ADP levels initially dropped when cells were switched from acetate to glucose. After 30 min ADP levels began to rise again slowly before eventually leveling out. Values reported are an average of a total of 150 cells quantified and error bars represent the standard error of the mean. FIG. 9D is a panel of images illustrating that the SAM sensor detects changes in endogenous SAM levels in living cells. E. coli expressing the SAM sensor were treated with either 25 µM methionine or vehicle and imaged continuously for 3 hr. Images of cells 0 min and 180 min after treatment are shown. SAM levels increased an average of six-fold upon treatment with methionine (a precursor in SAM synthesis) whereas vehicle-treated cells showed only minimal increases in SAM levels. Scale bar, 5 µm. FIG. 9E is a graph illustrating that the increases in SAM fluorescence correlate with biochemical measurements of SAM. SAM sensors can accurately measure increases in endogenous SAM levels. SAM sensor-expressing cells were treated with 50 µg/ml methionine (+met) or vehicle (−met) for 3 hr and fluorescence increases were measured in single living cells by epifluorescence microscopy. Cells treated identically were also lysed at different time points and total SAM levels were measured by an HPLC assay. Average fluorescence increase was plotted against HPLC data. SAM RNA sensors accurately measure increases in SAM levels and correlate with HPLC data. For fluorescence measurements, 300 cells were quantified for each condition over three experimental replicates. For HPLC measurements, the average value from three experimental replicates is plotted. Error bars represent the standard error of the mean.

FIG. 10A is a panel of images showing the distinct patterns of SAM accumulation in individual cells. E. coli expressing the SAM sensor were briefly starved of methionine in minimal media to deplete intracellular SAM. Cells were then incubated in minimal media with 200 µM DFHBI and 50 µg/ml methionine to induce SAM synthesis and imaged continuously for 180 min. Cells displayed high variability in the pattern of SAM accumulation over time. Cells are pseudo-colored to show the fold increase in SAM accumulation, relative to the 0 min timepoint, over the course of the experiment with blue being the lowest (no change in fluorescence) and red being the highest (11.2 fold increase in SAM). Some cells exhibited higher than average increases in intracellular SAM levels (indicated with arrow). Other cells showed slow increases in SAM levels (indicated with arrowhead). A cell that first increases and then decreases its SAM levels over the course of the experiment is indicated by a double arrow. Scale bar, 5 µm. FIG. 10B is a three-dimensional graph showing the variability in SAM accumulation revealed by single cell measurements of intracellular SAM levels. E. coli were prepared as described above and total SAM sensor fluorescence was quantified per cell. Single cell measurements of the fold increase in fluorescence relative to the t=0 timepoint reveal large variations in SAM levels in different cells across the entire population. This fold increase in variance of the population increases from 30 min to 180 min, indicating that the population becomes more diverse with time. Values are reported as fold increase in fluorescence from values immediately after methionine treatment, and the percentage of cells in the population displaying a given fold increase in SAM are plotted. A total of 800 cells per time point were quantified from three experimental replicates. FIGS. 10C-F are graphs showing that SAM recycling pathways influence SAM levels and variability in SAM accumulation in the population. Cells expressing the SAM sensor were briefly methionine starved and then incubated with 50 µg/ml methionine together with either vehicle, an SAH hydrolase inhibitor (Ado-2',3'-dial), or an SAH nucleosidase inhibitor (MT-DADMe-ImmA). Treatment with Ado-2',3'-dial reduced the variability in SAM levels seen across the entire population. However, by 120 min, the Ado-2',3'-dial-treated population exhibits considerable variability in intracellular SAM levels. Treatment with Mt-DADMe-ImmA, on the other hand, resulted in a substantial reduction in average SAM accumulation levels, and resulted in higher variability in SAM levels across the population at each time point. These data indicate that SAH hydrolase and SAH nucleosidase have different roles in influencing the variability in SAM metabolism in E. coli.

FIG. 11A illustrates a derivative Spinach sequence containing a shortened stem-loop 2 (SEQ ID NO: 8) and its use in testing the requirements for a stem-loop at the position of stem-loop 2. Because the original stem-loop 2 was present and fixed in all members of the RNA library used to identify Spinach, it is unlikely to make sequence-specific contacts with DFHBI. If Spinach-induced DFHBI fluorescence is dependent on the structure of this stem-loop, then sensors which allosterically regulate the formation of the stem would activate fluorescence. Also shown in this figure are the predicted secondary structures of the minimized stem-loop 2 from SEQ ID NO: 8, a replacement stem-loop present in the Spinach derivative of SEQ ID NO: 9, and a mismatch stem-loop structure (SEQ ID NO: 16) that was also introduced. The replacement stem-loop (present in SEQ ID NO: 9) differs completely in sequence to stem-loop 2, but retains a similar structure. The mismatched stem (SEQ ID NO: 16) retains the original UUCG tetraloop found in Spinach, but replaces the stem with three mismatched nucleotides to prevent duplex formation. The structures were generated using Mfold.

In FIG. 12A, Spinach RNA was produced in which stem-loop 2 was replaced with an aptamer to adenosine, where the adenosine aptamer was fused to Spinach by one of seven different transducer modules (present in SEQ ID NOS: 17-23). These transducer modules contained different combination of G-C, A-U and G-U base pairs, and were chosen because they were predicted to have a very low probability of duplex formation using the prediction software Mfold. Adenosine sensors containing different stems (stem 1-7) were incubated with 10 µM DFHBI in the presence or absence of 1 mM adenosine, and fluorescence emission was measured. The optimal transducer module (stem 2) was chosen because in the context of the sensor it displayed low background fluorescence, with a 20-fold increase in fluorescence signal upon incubation with adenosine. Stem 2 contained primarily A-U and G-U base pairs with G-C pairs only at the ends of the stem. In FIG. 12B, Spinach-based sensors to ADP were produced with different transducer modules (stems 1-8, SEQ ID NOS: 24-31) as described above for adenosine sensors. ADP sensor transducer modules contained different combination of G-C, A-U and G-U base pairs, and were chosen because they were predicted to have a very low probability of duplex formation using the prediction software Mfold. ADP sensor variants were tested as described for the adenosine sensors, and an optimal transducer module (stem 3) with a 20-fold increase in fluorescence was identified. In FIG. 12C, Spinach-based sensors to SAM were produced with different transducer modules (stems 1-10, SEQ ID NOS: 32-41) as described above for adenosine and ADP sensors. SAM sensor transducer modules contained different lengths and combinations of G-C, A-U and G-U base pairs. Longer stems in the transducer module lead to increased fluorescence in the absence of SAM. The optimal transducer module contained only a single G-C base pair (stem 1), which was positioned adjacent to the SAM binding site. This sensor has a 25-fold increase in fluorescence upon SAM binding and exhibited the lowest background signal.

FIG. 13A is a graph showing the dose-response curve for fluorescence detection of adenosine by the RNA-based sensor to adenosine. Half-maximal fluorescence is reached at 44 µM adenosine. FIG. 13B is a graph showing the dose-response curve for fluorescence detection of GTP by the RNA-based sensor to GTP. Curve fitting predicted that half-maximal fluorescence is reached at 7.7 mM GTP. FIG. 13C is a graph showing the dose-response curve for fluorescence detection of guanine by the RNA-based guanine sensor. Half-maximal fluorescence is reached at 1.5 µM guanine FIG. 13D is a graph showing the molecular discrimination of adenosine sensor. 0.1 µM RNA and 10 µM DFHBI were incubated with 1 mM adenosine or competing molecules and assayed for fluorescence emission at 500 nm. The adenosine sensor does not discriminate between adenosine and 5'-phosphorylated adenosine derivatives including ATP and ADP. However, the sensor is specific for adenosine over the 3'-phosphorylated adenosine derivative camp. The adenosine sensor also shows negligible fluorescence in the presence of guanine-containing nucleosides (guanosine) and nucleotides (GTP). FIG. 13E is a graph showing the molecular discrimination of the GTP sensor. 0.1 µM RNA and 10 µM DFHBI were incubated with 1 mM GTP or competing molecules and assayed for fluorescence emission at 500 nm. The GTP sensor exhibits moderate preference for GTP over GMP. It was expected that this sensor could be mutagenized and re-selected to be more specific for GTP over other 5'-phosphorylated derivatives, such as GDP and GMP. The GTP sensor exhibits tenfold less fluorescence in the presence of the 3'-phosphorylated derivative cGMP and the unphosphorylated nucleoside guanosine. Only baseline fluorescence is seen in the presence of ATP. FIG. 13F is a graph showing the molecular discrimination of the guanine sensor. The guanine sensor saturates at 100 µM guanine, and shows a high level of molecular discrimination against guanosine and adenine at the same concentrations. 0.1 µM RNA and 10 µM DFHBI were incubated with 100 µM guanine or competing molecules and assayed for fluorescence emission at 500 nm. guanosine. Only baseline fluorescence is seen in the presence of guanosine or adenine. FIG. 13G is a graph showing the measurement of rate of SAM sensor activation. A solution of RNA sensor (1 µM) and DFHBI (10 µM) was incubated with continuous stirring at 37° C. in a buffer containing 40 mM HEPES pH 7.4, 125 mM KCl and 1 mM $MgCl_2$. SAM (1 mM) was then rapidly added to the stirring solutions and fluorescence emission was recorded over a 15 min period under continuous illumination at 37° C. using the following instrument parameters: excitation wavelength, 460 nm; emission wavelength, 500 nm; increment of data point collection, 0.05 s; slit widths, 10 nm. The fluorescence increase was then plotted against exposure time and normalized to the maximum intensity. SAM sensors reach maximal fluorescence within 10 min. FIG. 13H is a graph showing the measurement of rate of ADP sensor activation. A solution of RNA sensor (1 µM) and DFHBI (10 µM) was incubated with continuous stirring at 37° C. in a buffer containing 40 mM HEPES pH 7.4, 125 mM KCl and 1 mM $MgCl_2$. ADP (1 mM) was added to the stirring solutions and fluorescence emission was recorded over a 15 min period under continuous illumination at 37° C. using the following instrument parameters: excitation wavelength, 460 nm; emission wavelength, 500 nm; increment of data point collection, 0.05 s; slit widths, 10 nm. The fluorescence increase was then plotted against exposure time and normalized to the maximum intensity. ADP sensors reach maximal fluorescence within 12 min.

FIG. 14A contains phase and fluorescence images of *E. coli* transformed with a plasmid expressing Spinach RNA. Spinach-expressing cells were imaged under microscope settings where fluorescence was non-saturated and the level of fluorescence signal was quantified per cell. Cells exhibited highly uniform levels of fluorescence throughout the population demonstrating that this expression system produces very little cell-to-cell variation in heterologous RNA expression levels.

FIG. 14B is a graph showing the quantification of fluorescence signal from Spinach-expressing cells in a population. Spinach fluorescence levels were quantified per cell and the number of cells with a given fluorescence intensity were plotted as percentage change for the mean fluorescence calculated from the entire population. 150 cells were counted across three experimental replicates. The large majority of cells exhibited Spinach fluorescence signal within +/−10% of mean fluorescence for the entire population of cells.

DETAILED DESCRIPTION OF THE INVENTION

Figure 2A:
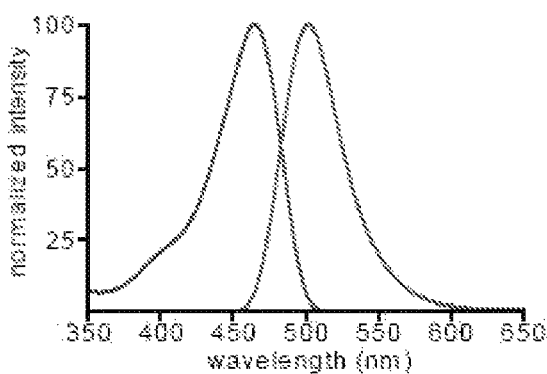
FIGS. 2A-E illustrate the properties of molecular complexes formed by aptamer 24-2 and DFHBI.

The present invention relates to novel nucleic acid aptamers that can bind selectively to conditionally fluorescent molecules ("fluorophores") to enhance the fluorescence signal of the fluorophore upon exposure to radiation of suitable wavelength. Molecular complexes formed between the novel aptamers and fluorophores, and their target molecules are also discussed below, as are the uses of these novel materials.

Fluorophores and Their Synthesis

The fluorophores recognized by the nucleic acid aptamers of the present invention include those that possess a methyne (also known as methine) bridge between a substituted aromatic ring system and a substituted imidazol(thi)one, oxazol(thi)one, pyrrolin(thi)one, or furan(thi)one ring. Importantly, the methyne bridge contains a single carbon that is double-bonded to a ring carbon of the substituted imidazol(thi)one, oxazol(thi)one, pyrrolin(thi)one, or furan(thi)one ring. Thus, these conditionally fluorescent compounds are unlike cyanine dyes characterized by a polymethyne bridge.

The fluorophores used in the present invention are characterized by a low quantum yield at a desired wavelength in the absence of aptamer binding. In certain embodiments, the quantum yield of the fluorophore, in the absence of specific aptamer binding, is less than about 0.01, more preferably less than about 0.001, most preferably less than about 0.0001.

The fluorophores are substantially unable to exhibit increases in quantum yield upon binding or interaction with molecules other than the aptamer(s) that bind specifically to them. This includes other molecules in a cell or sample besides those aptamer molecules having a polynucleotide sequence that was selected for binding to the fluorophore.

The fluorophores are preferably water soluble, non-toxic, and cell permeable. Preferably, the fluorophore is soluble in an aqueous solution at a concentration of 0.1 µM, 1 µM, more preferably 10 µM, and most preferably 50 µM or higher. Preferably, incubating a cell with these concentrations of the fluorophore does not affect the viability of the cell. The fluorophores are preferably capable of migrating through a cell membrane or cell wall into the cytoplasm or periplasm of a cell by either active or passive diffusion. Preferably, the fluorophore is able to migrate through both the outer and inner membranes of gram-negative bacteria, the cell wall and membrane of gram-positive bacteria, both the cell wall and plasma membrane of plant cells, cell wall and membrane of fungi and molds (e.g. yeast), the capsid of viruses, the plasma membrane of an animal cell, and through the GI tract or endothelial cell membranes in animals.

As used herein, the terms "enhance the fluorescence signal" or "enhanced signal" (i.e., upon specific aptamer binding) refer to an increase in the quantum yield of the fluorophore when exposed to radiation of appropriate excitation wavelength, a shift in the emission maxima of the fluorescent signal (relative to the fluorophore emissions in ethanol glass or aqueous solution), an increase in the excitation coefficient, or two or more of these changes. The increase in quantum yield is preferably at least about 1.5-fold, more preferably at least about 5 to 10-fold, at least about 20 to 50-fold, more preferably at least about 100 to about 200-fold. Fold increases in quantum yield exceeding 500-fold and even 1000-fold have been achieved with the present invention.

The radiation used to excite the fluorophore may be derived from any suitable source, preferably any source that emits radiation within the visible spectrum or infrared spectrum. The radiation may be directly from a source of radiation (e.g., a light source) or indirectly from another fluorophore (e.g., a FRET donor fluorophore). The use of FRET pairs is discussed more fully hereinafter.

Preferred fluorophores that can be used in accordance with the present invention include those according to formula I below:

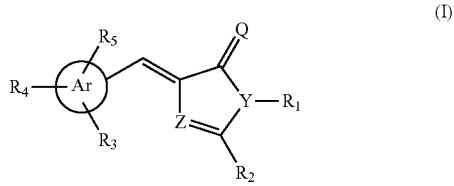

(I)

wherein,

Q is S or O,

Y is O or N,

Z is N or C($R_{10}$),

Ar is an aromatic or hetero-aromatic ring system comprising one or two rings;

$R_1$ is present when Y is N, and is a $C_{1-8}$ hydrocarbon or —$(CH_2)_n$—$R_6$ where n is an integer greater than or equal to 1;

$R_2$ is methyl, a mono-, di-, or tri-halo methyl, an aldoxime, an O-methyl-aldoxime, iminomethyl, carboxylic acid, thioic acid, (thio)amido, alkyl(thio)amido, unsubstituted or substituted phenyl with up to three substituents ($R_7$-$R_9$), (meth)acrylate, $C_{2-8}$ unsaturated hydrocarbon optionally terminated with an amine, amide, carboxylic acid, ester, enone, oxime, O-methyl-oxime, imine, nitromethane, nitrile, ketone, mono-, di-, tri-halo, nitro, cyano, acrylonitrile, acrylonitrile-enoate, acrylonitrile-carboxylate, acrylonitrile-amide, alkylester, or a second aromatic or hetero-aromatic ring;

$R_3$-$R_5$ are independently selected from H, hydroxy, alkyl, alkoxy, fluoro, chloro, bromo, a mono-, di-, or tri-halo alkoxy, amino, alkylamino, dialkylamino, (thio)amido, alkyl(thio)amido, alkylthio, cyano, mercapto, nitro, and mono-, di-, or tri-halo methyl, ketone, carboxylic acid, thioc acid, alkylester, a surface-reactive group, a solid surface, or a functional group that can be linked to a reactive group on the solid surface;

$R_6$ is H, hydroxy, alkyl, alkoxy, fluoro, chloro, bromo, a mono-, di-, or tri-halo alkoxy, amino, alkylamino, dialkylamino, (thio)amido, alkyl(thio)amido, alkylthio, cyano, mercapto, nitro, and mono-, di-, or tri-halo methyl, ketone, carboxylic acid, alkylester, a surface-reactive group, a solid surface, or a functional group that can be linked to a reactive group on the solid surface; and $R_7$-$R_{10}$ are independently selected from H, hydroxy, alkyl, alkoxy, fluoro, chloro, bromo, amino, alkylamino, dialkylamino, (thio)amido, alkyl(thio)amido, alkylthio, cyano, mercapto, nitro, and mono-, di-, or tri-halo methyl, ketone, carboxylic acid, thioic acid, and alkylester.

As used in the preceding definitions, alkyl substituents are C1 to C6 alkyls, preferably methyl or ethyl groups. In the various substituents, an optional thio-derivative identified using, e.g., (thio)amido, is intended to encompass both amido and thioamido groups.

As used in the definition of $R_3$-$R_6$, the solid surface can be any solid surface, including glass, plastics, metals, semiconductor materials, ceramics, and natural or synthetic polymers (e.g., agarose, nitrocellulose). The solid surface can be an optically transparent material.

By surface-reactive group, it is intended that the group is a carboxylic acid (which can be modified by a carbodiimide to react with amines or alcohols), NHS ester, imidoester, PFP ester, p-nitrophenyl ester, hydroxymethyl phosphine, maleimide, haloacetyl group, haloacetamide group, vinyl sulfone, hydrazide, isocyanate, oxirane, epoxide, thiol, amine, alkyne, azide, anhydride, sulfonyl chloride, acyl chloride, ethylenimine, mixed disulfides, activated disulfides, or thiosulfinate. By functional group that can be linked to a reactive group on a solid surface, it is intended that the group is any reactive group, including without limitation, carboxyl, amine, sulfhydryl, aldehyde, hydroxyl, thiol, or any of the groups listed as suitable for the surface-reactive group.

The compounds of the invention also encompass salts, particularly phenolate salts.

Other known compounds within the scope of formula I include those where Ar is phenyl, Z and Y are both N, and either (i) $R_3$-$R_5$ are all H; (ii) $R_1$ and $R_2$ are methyl, $R_4$ and $R_5$ are H, and $R_3$ is hydroxy, methoxy, or dimethylamino; and (iii) $R_1$ is methyl, $R_4$ and $R_5$ are H, $R_3$ is hydroxy, and $R_2$ is a conjugated hydrocarbon chain. Other such compounds of formula I include those disclosed in He et al., "Synthesis and Spectroscopic Studies of Model Red Fluorescent Protein Chromophores," Org. Lett. 4(9):1523-26 (2002); You et al., "Fluorophores Related to the Green Fluorescent Protein and Their Use in Optoelectornic Devices," Adv. Mater. 12(22):1678-81 (2000); and Bourotte et al., "Fluorophores Related to the Green Fluorescent Protein," Tetr. Lett. 45:6343-6348 (2004), each of which is hereby incorporated by reference in its entirety). In certain embodiments, these previously known compounds are excluded from the scope of the invention.

Subclasses of these fluorophores, including oxazolithiones, pyrrolinthiones, imidazolithiones, and furanthiones, as well as those possessing an oxazolone ring, imidazolone ring, furanone ring, or pyrrolinone ring, are shown and/or described in PCT Application Publ. No. WO/2010/096584 to Jaffrey and Paige, which is hereby incorporated by reference in its entirety. In certain embodiments, these previously known compounds are excluded from the scope of the invention.

Further diversification of the compounds can be achieved by conversion of an $R_2$ methyl group in compounds of formula I into an aldehyde using selenium dioxide (with dioxane under reflux). The resulting aldehyde can be converted into a $C_{2-8}$ unsaturated hydrocarbon, preferably a conjugated hydrocarbon, using the Wittig reaction. Basically, the resulting aldehyde is reacted with a triphenyl phosphine (e.g., $Ph_3P=R_{10}$ where $R_{10}$ is the unsaturated hydrocarbon) in the presence of strong base. The unsaturated hydrocarbon that is present in the Wittig reactant is optionally terminated with any desired functional group, preferably an amine, amide, carboxylic acid, (meth)acrylate, ester, enone, oxime, O-methyl-oxime, imine, nitromethane, nitrile, ketone, mono-, di-, tri-halo, nitro, cyano, acrylonitrile, acrylonitrile-enoate, acrylonitrile-carboxylate, acrylonitrile-amide, or a second aromatic or hetero-aromatic ring. These reactants are commercially available or readily synthesized by persons of skill in the art. Alternatively, the resulting aldehyde can be reacted with hydroxylamine or methoxyamine derivative according to the procedure of Maly et al., "Combinatorial Target-guided Ligand Assembly: Identification of Potent Subtype-selective c-Src Inhibitors," *Proc Natl Acad Sci USA* 97(6): 2419-24 (2002), which is hereby incorporated by reference in its entirety) (see compounds of formulae IIIa, IIIb below). The aldehyde can also be reacted with nitromethane to form acrylonitro groups according to established protocols (see Muratore et al., "Enantioselective Bronsted Acid-catalyzed N-acyliminium Cyclization Cascades," *J Am Chem Soc* 131(31):10796-7 (2009); Crowell and Peck, *J. Am. Chem. Soc.* 75:1075 (1953), each of which is hereby incorporated by reference in its entirety). Additionally, aldehydes can be reacted with nucleophilic cyano-containing molecules such as 2-cyanoacetamide, malononitrile methylcyanoacetate, cyano acetic acid, etc., in a Knoevenagel condensation reaction to produce acrylonitrile groups with different functional groups (Cope et al., *J. Am. Chem. Soc.* 63:3452 (1941), which is hereby incorporated by reference in its entirety).

Alternatively, the $R_2$ methyl can be replaced with a mono-, di-, or tri-halomethyl group. Halo-substituted acetamides are readily available, and are sufficiently reactive with the arylaldehydes.

In the compounds of formula I, Ar can be any single or multiple (including fused) ring structure, except as noted above when Ar is phenyl. Preferred Ar groups include substituted phenyl, naphthalenyl pyridinyl, pyrimidinyl, pyrrolyl, furanyl, benzofuranyl, thiophene-yl, benzothiophene-yl, thiazolyl, benzothiazolyl, imidizolyl, benzoimidizolyl, oxazolyl, benzoxazolyl, purinyl, indolyl, quinolinyl, chromonyl, or coumarinyl groups. The substituents of these Ar groups can be one or more of hydrogen, hydroxy, alkyl, alkoxy, fluoro, chloro, bromo, a mono-, di-, or tri-halo alkoxy, amino, alkylamino, dialkylamino, (thio)amido, alkyl(thio)amido, alkylthio, cyano, mercapto, nitro, and mono-, di-, or tri-halo alkyl, ketone, carboxylic acid, and thioc acid. The aromatic or hetero-aromatic group terminating the $R_2$ group can also be any one or the Ar groups identified above.

Other suitable subclasses of these compounds are the tri-substituted benzylidene imidazolones of formulae II, IIIa, and IIIb as described in PCT Application Publ. No. WO/2010/096584 to Jaffrey and Paige, which is hereby incorporated by reference in its entirety.

Exemplary fluorophores identified in the above-referenced PCT Application Publ. No. WO/2010/096584 to Jaffrey and Paige include, without limitation, 4-(3,4,5-trimethoxybenzylidene)-1,2-dimethyl-imidazol-5-one ("TMBI"); 4-(4-hydroxy-3,5-dimethoxybenzylidene)-1,2-dimethyl-imidazol-5-one ("DMHBI"); 4-(3,5-difluoro-4-hydroxybenzylidene)-1,2-dimethyl-imidazol-5-one ("DFHBI"); (E)-4-(3,5-difluoro-4-hydroxybenzylidene)-1-methyl-5-oxo-4,5-dihydro-1H-imidazole-2-carbaldehyde O-methyl oxime ("DFHBI-methyloxime"); 4-(3,5-dichloro-4-hydroxybenzylidene)-1,2-dimethyl-imidazol-5-one; 4-(3,5-dibromo-4-hydroxybenzylidene)-1,2-dimethyl-imidazol-5-one; 4-(2-hydroxybenzylidene)-1,2-dimethyl-imidazol-5-one ("o-HBI"); 4-(2-methoxybenzylidene)-1,2-dimethyl-imidazol-5-one; 4-(3-fluoro-4-hydroxy-5-methoxybenzylidene)-1,2-dimethyl-imidazol-5-one; 4-(4-(dimethylamino)benzylidene)-1,2-dimethyl-imidazol-5-one ("DMABI"); 4-(4-(t-butylthio)benzylidene)-1,2-dimethyl-imidazol-5-one; 4-(4-(methylthio)benzylidene)-1,2-dimethyl-imidazol-5-one; 4-(4-cyanobenzylidene)-1,2-dimethyl-imidazol-5-one; 4-(3,5-difluoro-4-acetate)benzylidene-1,2-dimethyl-imidazol-5-one; 4-(4-hydroxy-3-nitrobenzylidene)-1,2-dimethyl-imidazol-5-one; 4-(4-hydroxy-3-methoxy-5-nitrobenzylidene)-1,2-dimethyl-imidazol-5-one; 4-(4-methoxy-3-nitrobenzylidene)-1,2-dimethyl-imidazol-5-one; 4-(4-bromobenzylidene)-1,2-dimethyl-imidazol-5-one; 4-(4-chlorobenzylidene)-1,2-dimethyl-imidazol-5-one; 4-(4-hydroxybenzylidene)-1,2-dimethyl-imidazol-5-one ("p-HBI"); 4-((indol-7-yl)methylene)-1,2-dimethyl-imidazole-5-one; 4-((indol-3-yl)methylene)-1,2-dimethyl-imidazole-5-one; 4-((indol-3-yl)methylene)-1-methyl-2-phenyl-imidazole-5-one; 4-(4-hydroxy-3,5-dimethoxybenzylidene)-1-methyl-2-phenyl-imidazole-5-one; 4-(4-(dimethylamino)benzylidene)-1-methyl-2-phenyl-imidazole-5-one; 4-(4-hydroxybenzylidene)-2-acetyl-1-methyl-imidazole-5-one; 4-(4-hydroxybenzylidene)-1-methyl-2-prop-1-enyl-imidazole-5-one; 3-(4-(4-hydroxybenzylidene)-4,5-dihydro-1-methyl-5-oxo-imidazol-2-yl)acrylamide; 3-(4-(4-hydroxybenzylidene)-4,5-dihydro-1-methyl-5-oxo-imidazol-2-yl) acrylic acid; and methyl 3-(4-(4-hydroxybenzylidene)-4,5-dihydro-1-methyl-5-oxo-imidazol-2-yl)acrylate. Of these, DFHBI and DFHBI-methyloxime are particularly desirable because of their distinct emission maxima and high quantum yield.

Additional conditional fluorophores include, without limitation:

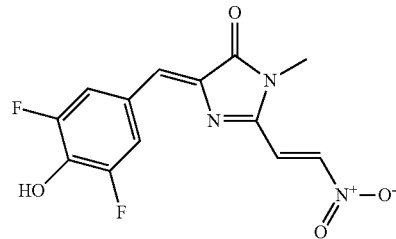 [SMILES: CN1C(=O)/C(=C/c2cc(F)c(O)c(F)c2)N=C1/C=C/[N+](=O)[O-]]

4-(3,5-difluoro-4-hydroxybenzylidene)-1-methyl-2-((E)-2-nitrovinyl)-1H-imidazol-5(4H)-one ("DFAN")

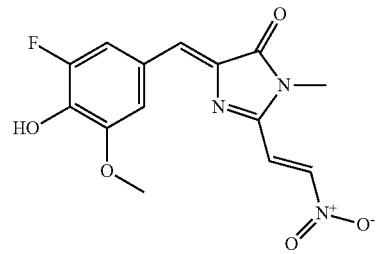 [SMILES: COc1cc(/C=C2N=C(/C=C/[N+](=O)[O-])N(C)C\2=O)cc(F)c1O]

4-(3-fluoro-4-hydroxy-5-methoxybenzylidene)-1-methyl-2-((E)-2-nitrovinyl)-1H-imidazol-5(4H)-one;

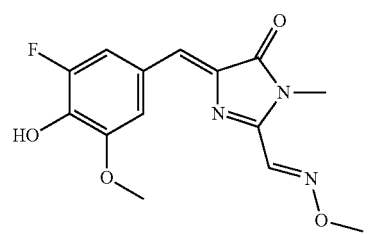 [SMILES: CO/N=C/C1=NC(=C\c2cc(F)c(O)c(OC)c2)/C(=O)N1C]

4-(3-fluoro-4-hydroxy-5-methoxybenzylidene)-1-methyl-5-oxo-4,5-dihydro-1H-imidazole-2-carbaldehyde O-methyl oxime;

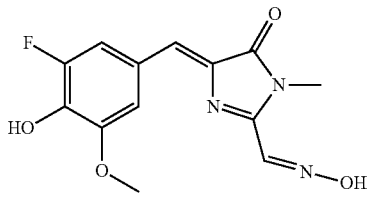 [SMILES: COc1cc(/C=C2\N=C(C=NO)N(C)C2=O)cc(F)c1O]

4-(3-fluoro-4-hydroxy-5-methoxybenzylidene)-1-methyl-5-oxo-4,5-dihydro-1H-imidazole-2-carbaldehyde oxime ("MFHO");

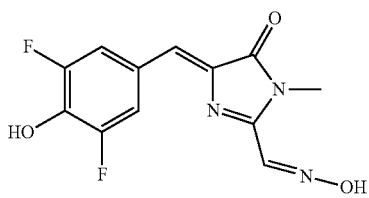 [SMILES: CN1C(=O)/C(=C/c2cc(F)c(O)c(F)c2)N=C1C=NO]

4-(3,5-difluoro-4-hydroxybenzylidene)-1-methyl-5-oxo-4,5-dihydro-1H-imidazole-2-carbaldehyde oxime ("DFHO");

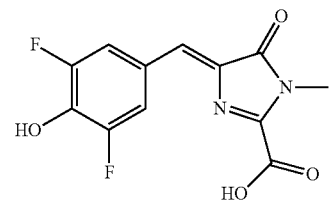 [SMILES: CN1C(=O)/C(=C/c2cc(F)c(O)c(F)c2)N=C1C(=O)O]

4-(3,5-difluoro-4-hydroxybenzylidene)-1-methyl-5-oxo-4,5-dihydro-1H-imidazole-2-carboxylic acid;

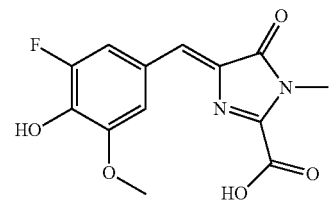 [SMILES: COc1cc(/C=C2\N=C(C(=O)O)N(C)C2=O)cc(F)c1O]

4-(3-fluoro-4-hydroxy-5-methoxybenzylidene)-1-methyl-5-oxo-4,5-dihydro-1H-imidazole-2-carboxylic acid;

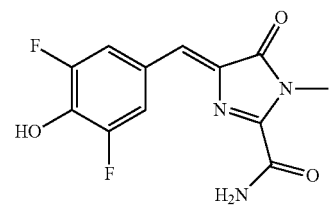 [SMILES: CN1C(=O)/C(=C/c2cc(F)c(O)c(F)c2)N=C1C(N)=O]

4-(3,5-difluoro-4-hydroxybenzylidene)-1-methyl-5-oxo-4,5-dihydro-1H-imidazole-2-carboxamide;

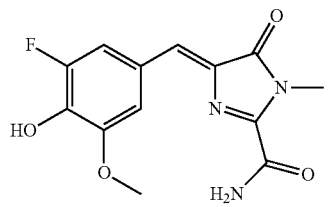 [SMILES: COc1cc(/C=C2\N=C(C(N)=O)N(C)C2=O)cc(F)c1O]

4-(3-fluoro-4-hydroxy-5-methoxybenzylidene)-1-methyl-5-oxo-4,5-dihydro-1H-imidazole-2-carboxamide;

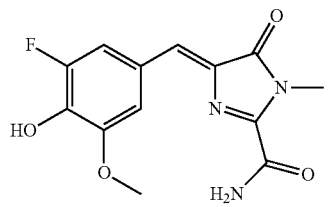 [SMILES: COc1cc(/C=C2\N=C(C(N)=O)N(C)C2=O)cc(F)c1O]

4-(3,5-difluoro-4-hydroxybenzylidene)-N,1-dimethyl-5-oxo-4,5-dihydro-1H-imidazole-2-carboxamide;

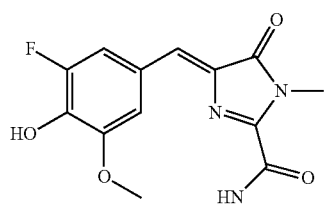

4-(3-fluoro-4-hydroxy-5-methoxybenzylidene)-N,1-dimethyl-5-oxo-4,5-dihydro-1H-imidazole-2-carboxamide;

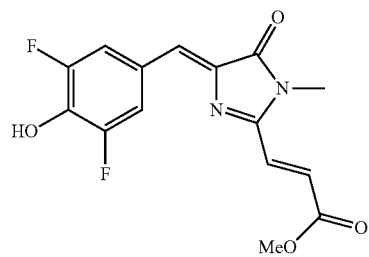 [SMILES: COC(=O)/C=C/C1=NC(=C\c2cc(F)c(O)c(F)c2)/C(=O)N1C]

methyl 3-((Z)-4-(3,5-difluoro-4-hydroxybenzylidene)-1-methyl-5-oxo-4,5-dihydro-1H-imidazol-2-yl)acrylate ("DFAME");

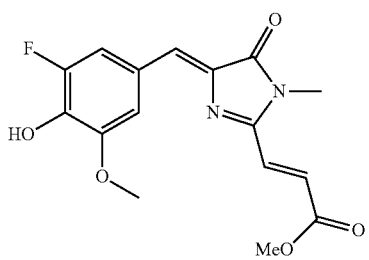 [SMILES: COC(=O)/C=C/C1=NC(=C\c2cc(F)c(O)c(OC)c2)/C(=O)N1C]

methyl 3-(4-(3-fluoro-4-hydroxy-5-methoxybenzylidene)-1-methyl-5-oxo-4,5-dihydro-1H-imidazol-2-yl)acrylate, and

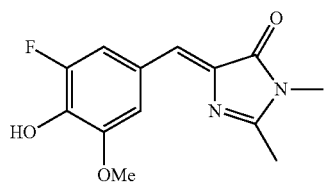 [SMILES: COc1cc(/C=C2\N=C(C)N(C)C2=O)cc(F)c1O]

4-(3-fluoro-4-hydroxy-5-methoxybenzylidene)-1,2-dimethyl-1H-imidazol-5(4H)-one ("MFHBI"). Of these, DFAN, DFAME, DFHO, MFHO, and MFHBI are particularly desirable because of their distinct emission maxima, relative to DFHBI and DFHBI-methyloxime, and their high quantum yield.

If cell permeability is a problem for some fluorophores, then acylation of phenolic moieties should improve the cell permeability without impacting fluorophore activity, as these acyl moieties are rapidly cleaved by intracellular esterases (Carrigan et al., "The Engineering of Membrane-permeable Peptides," *Anal Biochem.* 341:290-298 (2005), which is hereby incorporated by reference in its entirety). For fluorophores with low cell permeability, their O-acyl esters can be trivially made by reacting the fluorophores with the appropriate acid chloride, e.g., myristoyl, octanoyl, or butanoyl chloride. To the extent that these acyl moieties are not rapidly cleaved, these may in fact improve the fluorescence of the various RNA-fluorophore complexes.

Aptamers

The present invention also relates to nucleic acid molecules that are known in the art as aptamers. Aptamers are nucleic acid molecules characterized by a single-strand and having a secondary structure that may possess one or more stems (i.e., base-paired regions) as well as one or more non base-paired regions along the length of the stem. These non base-paired regions can be in the form of a bulge or loop (e.g., internal loop) along the length of the stem(s) and/or a loop at the end of the one or more stem(s) (e.g., hairpin loop). These nucleic acid aptamers possess specificity in binding to a particular target molecule, and they noncovalently bind their target molecule through an interaction such as an ion-ion force, dipole-dipole force, hydrogen bond, van der Waals force, electrostatic interaction, stacking interaction or any combination of these interactions.

Identifying suitable nucleic acid aptamers basically involves selecting aptamers that bind a particular target molecule with sufficiently high affinity (e.g., $K_d$<500 nM) and specificity from a pool or library of nucleic acids containing a random region of varying or predetermined length. For example, identifying suitable nucleic acid aptamers of the present invention can be carried out using an established in vitro selection and amplification scheme known as SELEX. The SELEX scheme is described in detail in U.S. Pat. No. 5,270,163 to Gold et al.; Ellington and Szostak, "In Vitro Selection of RNA Molecules that Bind Specific Ligands," *Nature* 346:818-822 (1990); and Tuerk and Gold, "Systematic Evolution of Ligands by Exponential Enrichment: RNA Ligands to Bacteriophage T4 DNA Polymerase," *Science* 249:505-510 (1990), each of which is hereby incorporated by reference in their entirety. An established template-primer system (Bartel et al., "HIV-1 Rev Regulation Involves Recognition of Non-Watson-Crick Base Pairs in Viral RNA," *Cell* 67:529-536 (1991), which is hereby incorporated by reference in its entirety) can be adapted to produce RNA molecules having a stretch of about 38-40 random bases sandwiched between 5' and 3' constant regions.

The synthetic oligonucleotide templates can be amplified by polymerase chain reaction ("PCR") and then transcribed to generate the original RNA pool. Assuming that ten percent of the RNA molecules are free of chemical lesions that prevent second-strand synthesis and transcription, this pool would contain more than $3\times10^{13}$ different sequences. Because filter binding is applicable for most protein targets, it can be used as the partitioning device, although other suitable schemes can be used. The selected primary RNA aptamers can be cloned into any conventional subcloning vector and sequenced using any variation of the dideoxy method. Next, the secondary structure of each primary RNA aptamer can be predicted by computer programs such as MulFold or mFOLD (Jaeger et al., "Improved Predictions of Secondary Structures for RNA," *Proc. Natl. Acad. Sci. USA* 86:7706-7710 (1989), and Zuker, "On Finding All Suboptimal Foldings of an RNA Molecule," *Science* 244:48-52 (1989), each of which is hereby incorporated by reference in its entirety). Mutational studies can be conducted by preparing substitutions or deletions to map both binding sites on the RNA aptamer and its target molecule, as well as to further enhance aptamer binding affinity, as described in the accompanying Examples.

Aptamers generated from SELEX experiments can be optimized to produce second generation aptamers with improved properties (Eaton et al., "Post-SELEX Combinatorial Optimization of Aptamers," *Bioorg. Med. Chem.* 5:1087-1096 (1997), which is hereby incorporated by reference in its entirety). Through successive rounds of affinity maturation of a primary SELEX clone, it is possible to obtain aptamers that possess improved fluorescence and higher quantum yield characteristics than the original clone. Therefore, prior to using aptamers in cell-based experiments, each aptamer can be optimized using the following considerations:

Find the minimal aptamer sequence within the SELEX clone to identify the domain to subject to affinity maturation. This will lead to more desirable, smaller aptamers, which should be better for tagging RNAs with aptamers;

It is important to know if the aptamers are selective for their intended fluorophore or if they bind other fluorophores that are intended to bind to other aptamers. In dual color imaging experiments involving two RNA-fluorophore complexes, cross-reactive fluorophores would be problematic.

The fluorescence of the aptamer-fluorophore complexes may be optimized by affinity maturation. This may avoid unwanted interference or FRET.

Additionally, tagging the target molecule with multiple tandem aptamers rather than a single aptamer will increase the fluorescence of a tagged target molecule. Tagging of the aptamers should be possible without impacting the aptamer ability to bind specifically to a particular fluorophore or target molecule of interest.

If any cross-reactivity is observed, then a doped library can be prepared and subjected to "negative selection," also called "counter-SELEX." There is considerable precedent that documents the ability of negative selection to generate aptamers with high degrees of selectivity, even among closely related molecules (Tuerk et al., "Using the SELEX Combinatorial Chemistry Process to Find High Affinity Nucleic Acid Ligands to Target Molecules," *Methods Mol Biol.* 67:219-230 (1997); Rink et al., "Creation of RNA Molecules that Recognize the Oxidative Lesion 7,8-dihydro-8-hydroxy-2'-deoxyguanosine (8-oxodG) in DNA," *Proc Natl Acad Sci USA* 95:11619-11624 (1998); Haller et al., "In vitro Selection of a 7-Methyl-guanosine Binding RNA that Inhibits Translation of Capped mRNA Molecules," *Proc Natl Acad Sci USA* 94:8521-8526 (1997); Edwards et al., "DNA-oligonucleotide Encapsulating Liposomes as a Secondary Signal Amplification Means," *Anal Chem.* 79:1806-1815 (1997), each of which is hereby incorporated by reference in its entirety). To perform negative selection, RNAs bound to dye-agarose are subjected to a washing step in which the buffer contains other fluorophores. This results in the elution of aptamers that have undesirable cross-reactivity. The RNAs that remain bound to the agarose beads are then eluted with the fluorophore of interest, and amplified as in the classic SELEX procedure. This process is repeated until clones are generated which do not bind and activate the fluorescence of inappropriate fluorophores.

Optimization of aptamers can also be achieved during re-selection by using rigorous washing conditions in all steps, including the use of high temperature (37° C. or 45° C.) washing buffers, mild denaturants, and low salt and high salt washes, etc. Since the quantum yield may reflect the efficiency of the RNA to conformationally restrict the photoexcited fluorophores, RNA aptamers that bind more tightly to the fluorophore may improve the quantum yield, and thereby the fluorescence of the RNA-fluorophore complexes. The proposed stringent washing conditions are intended to select for aptamers that bind more tightly to the fluorophore, and thereby improve the quantum yield. An additional benefit of generating RNA aptamers that bind with higher affinity to the fluorophore is that lower concentrations of fluorophore will be needed for live-cell experiments, which may reduce potential off-target or cytotoxic effects of the fluorophore. Since most aptamers that bind to small molecules bind with modest affinity, i.e., a $K_d$ of >100 nM (Famulok et al., "Nucleic Acid Aptamers-from Selection in vitro to Applications in vivo," *Accounts of Chemical Research* 33:591-599 (2000), which is hereby incorporated by reference in its entirety), it is expected that this high affinity will not affect the resistance to photobleaching.

Another method to use during optimization is the use of a smaller bias during doping. For example, the library can be doped with a 2:1:1:1 ratio instead of 5:1:1:1. This will result in more library members being substantially different from the parent aptamer.

The SELEX procedure can also be modified so that an entire pool of aptamers with binding affinity can be identified by selectively partitioning the pool of aptamers. This procedure is described in U.S. Patent Application Publication No. 2004/0053310 to Shi et al., which is hereby incorporated by reference in its entirety.

Single stranded DNA aptamers have advantages for in vitro settings due to their ease of synthesis and greater stability. Recent studies have argued that proper buffer conditions and certain RNA sugar modifications can lead to highly stable RNAs (Osborne et al., "Aptamers as Therapeutic and Diagnostic Reagents: Problems and Prospects," *Curr Opin Chem Biol.* 1:5-9 (1997); Faria et al., "Sugar Boost: When Ribose Modifications Improve Oligonucleotide Performance," *Current Opinion in Molecular Therapeutics* 10:168-175 (2008), each of which is hereby incorporated by reference in its entirety). Additionally, microarrays of RNAs have been shown to be stable in the presence of tissue lysates when suitable RNAase inhibitors are added (Collett et al., "Functional RNA Microarrays for High-throughput Screening of Antiprotein Aptamers," *Anal Biochem.* 338:113-123 (2005), which is hereby incorporated by reference in its entirety). Moreover, as part of the optimization and stabilization process, stabilizing hairpins can be added which markedly enhance aptamer levels in cells (Blind et al., "Cytoplasmic RNA Modulators of an Inside-out Signal-transduction Cascade," *Proc Natl Acad Sci USA* 96:3606-3610 (1999), which is hereby incorporated by reference in its entirety). Regardless, DNA aptamer sequences that switch on fluorophores of the invention would be inexpensive to synthesize and provide additional assurance of sensor stability in solution phase or microarray-based assays.

SELEX can be performed as readily with DNA as with RNA (Breaker, "DNA Aptamers and DNA Enzymes," *Curr Opin Chem Biol.* 1:26-31 (1997), which is hereby incorporated by reference in its entirety). The absence of a 2'-OH does not substantially impair the ability of DNA to fold or adopt structures. Indeed, SELEX has been used to identify DNAs that bind both small molecules and proteins, with structures that are reminiscent of RNA aptamers. Thus, DNA aptamers can be developed and subjected to analogous mutagenesis and truncation studies to identify entry points and analyte sensors as described herein.

As used herein, "nucleic acid" includes both DNA and RNA, in both D and L enantiomeric forms, as well as derivatives thereof (including, but not limited to, 2'-fluoro-, 2'-amino, 2'O-methyl, 5'iodo-, and 5'-bromo-modified polynucleotides). Nucleic acids containing modified nucleotides (Kubik et al., "Isolation and Characterization of 2'fluoro-, 2'amino-, and 2'fluoro-amino-modified RNA Ligands or Human IFN-gamma that Inhibit Receptor Binding," *J. Immunol.* 159:259-267 (1997); Pagratis et al., "Potent 2'-amino, and 2'-fluoro-2'-deoxy-ribonucleotide RNA Inhibitors of Keratinocyte Growth Factor," *Nat. Biotechnol.* 15:68-73 (1997), each which is hereby incorporated by reference in its entirety) and the L-nucleic acids (sometimes termed Spiegelmers®), enantiomeric to natural D-nucleic acids (Klussmann et al., "Mirror-image RNA that Binds D-adenosine," *Nat. Biotechnol.* 14:1112-1115 (1996) and Williams et al., "Bioactive and nuclease-resistant L-DNA Ligand of Vasopressin," *Proc. Natl. Acad. Sci. USA* 94:11285-11290 (1997), each which is hereby incorporated by reference in its entirety), and non-natural bases are used to enhance biostability. In addition, the sugar-phosphate backbone can be replaced with a peptide backbone, forming a peptide nucleic acid (PNA), other natural or non-natural sugars can be used (e.g., 2'-deoxyribose sugars), or phosphothioate or phosphodithioate can be used instead of phosphodiester bonds. The use of locked nucleic acids (LNA) is also contemplated.

According to one embodiment, the nucleic acid molecule includes a domain—an aptamer—that binds specifically to a fluorophore having a methyne bridge between a substituted aromatic ring system and a substituted imidazol(thi)one, oxazol(thi)one, pyrrolin(thi)one, or furan(thi)one ring. Preferably, the fluorophore is a compound according to any of formulae recited in PCT Application Publ. No. WO/2010/096584 to Jaffrey and Paige, which is hereby incorporated by reference in its entirety, which are briefly described above. These nucleic acid aptamers, upon binding to the fluorophore, induces the fluorophore to adopt a conformation whereby the fluorescent emission spectrum is substantially enhanced upon exposure to radiation of suitable wavelength.

According to one embodiment, the nucleic acid aptamer is an RNA molecule according to the consensus sequence of SEQ ID NO: 1 as follows:

```
GACGCNACNN NNNGAAAUGG UGAANGGACG GGUCCNAGNN
NNNNNNNNNN NNNNNNNNNNN NNCNUGUUGN GUNGAGUGUG
AGCUCNNCGU AACUNGUCGC GUC
``` where bold N's represent optional ribonucleotides, N at position 6 can be A, U, G, or C, but is preferably A or G; N at position 9 can be A, U, G, or C, but is preferably C or U; N at position 10 is optional and can be A, U, G, or C, but is preferably G or U; N at positions 11 and 12 are optional and can independently be A, U, G, or C, but are both preferably A; N at position 13 is optional and can be A, U, G, or C, but is preferably U; N at positions 25 and 36 are optional and independently can be A, U, G, or C, but they are preferably both absent or together form a stable or partially stable base pair such as G-C(C-G) or A-U (U-A); N at positions 39-44 and 57-62 are optional and independently can be A, U, G, or C, but they are preferably absent or together form a partially stabilized anti-parallel stem structure that may optionally include a bulge or unmatched base; N at positions 45-56 are independently A, U, G, or C, but they preferably together form a stable stem-loop structure such as that formed by UGCUUCGGCA (from SEQ ID NO: 7), CUGCUUCGGCAG (from SEQ ID NO: 8), or GCACGAAAGUGC (from SEQ ID NO: 9); N at position 64 is optional and can be A, U, G, or C, but is preferably U; N at positions 70 and 73 are optional and can independently be A, U, G, or C, but are both preferably C or A; N at positions 86 and 87 are optional and can independently be A, U, G, or C except that when both are present they are not CG, but preferably are both absent; and N at position 95 can be A, U, G, or C, but is preferably G or A so as to form a stable base pair with the ribonucleotide at position 9. The aptamer preferably has a melting temperature ($T_m$) that exceeds 37° C., such that the aptamer remains in a folded state under cellular conditions.

According to another embodiment, the nucleic acid aptamer is an RNA molecule according to the consensus sequence of SEQ ID NO: 2 as follows:

```
GACGCNACNN NNNGAAAUGG UGAANGGACG GGUCCNAGNN
GNNGCUGCUU CGGCAGNNNC NGCNUGUUGN GUNGAGUGUG
AGCUCNNCGU AACUNGUCGC GUC
``` where bold N's represent optional ribonucleotides, N at position 6 can be A, U, G, or C, but is preferably A or G; N at position 9 can be A, U, G, or C, but is preferably C or U; N at position 10 is optional and can be A, U, G, or C, but is preferably G or U; N at positions 11 and 12 are optional and can independently be A, U, G, or C, but are both preferably A; N at position 13 is optional and can be A, U, G, or C, but is preferably U; N at positions 25 and 36 are optional and independently can be A, U, G, or C, but they are preferably both absent or together form a stable or partially stable base pair such as G-C(C-G) or A-U (U-A); N at position 39 can be A, U, G, or C, but is preferably C or U; N at position 40 is optional and can be A, U, G, or C, but is preferably C or U; N at position 42 is optional and can be A, U, G, or C, but is preferably C or U; N at position 43 is optional and can be A, U, G, or C, but is preferably G; N at position 57 can be A, U, G, or C, but is preferably C or U; N at position 58 is optional and can be A, U, G, or C, but preferably forms a stable or partially stable base pair with the ribonucleotide at position 43; N at position 59 is optional and can be A, U, G, or C, but preferably forms a stable or partially stable base pair with the ribonucleotide at position 42; N at position 61 is optional and can be A, U, G, or C, but preferably forms a stable or partially stable base pair with the ribonucleotide at position 40; N at position 64 is optional and can be A, U, G, or C, but is preferably U; N at positions 70 and 73 are optional and can independently be A, U, G, or C, but are both preferably C or A; N at positions 86 and 87 are optional and can independently be A, U, G, or C except that when both are present they are not CG, but preferably are both absent; and N at position 95 can be A, U, G, or C, preferably forms a stable base pair with the ribonucleotide at position 9. The aptamer preferably has a melting temperature ($T_m$) that exceeds 37° C., such that the aptamer remains in a folded state under cellular conditions.

According to another embodiment, the nucleic acid aptamer is an RNA molecule according to the consensus sequence of SEQ ID NO: 3 as follows:

```
GACGCNACNN NNNGAAAUGG UGAAGGACGG GUCCAGNNGN
NGCUGCUUCG GCAGNNNCNG CNUGUUGAGU AGAGUGUGAG
CUCCGUAACU NGUCGCGUC
``` where bold N's represent optional ribonucleotides, N at position 6 can be A, U, G, or C, but is preferably A or G; N at position 9 can be A, U, G, or C, but is preferably C or U; N at position 10 is optional and can be A, U, G, or C, but is preferably G; N at positions 11 and 12 are optional and can independently be A, U, G, or C, but are both preferably A; N at position 13 is optional and can be A, U, G, or C, but is preferably U; N at position 37 can be A, U, G, or C, but is preferably C or U; N at position 38 can be A, U, G, or C, but is preferably C or U; N at position 40 is optional and can be A, U, G, or C, but is preferably C or U; N at position 41 is optional and can be A, U, G, or C, but is preferably G; N at position 55 can be A, U, G, or C, but is preferably C or U; N at position 56 is optional and can be A, U, G, or C, but preferably forms a stable or partially stable base pair with the ribonucleotide at position 41; N at position 57 is optional and can be A, U, G, or C, but preferably forms a stable or partially stable base pair with the ribonucleotide at position 40; N at position 59 is optional and can be A, U, G, or C, but preferably forms a stable or partially stable base pair with the ribonucleotide at position 38; N at position 62 is optional and can be A, U, G, or C, but is preferably U; and N at position 91 can be A, U, G, or C, but preferably forms a stable base pair with the ribonucleotide at position 9. The aptamer preferably has a melting temperature ($T_m$) that exceeds 37° C., such that the aptamer remains in a folded state under cellular conditions.

Figure 17:
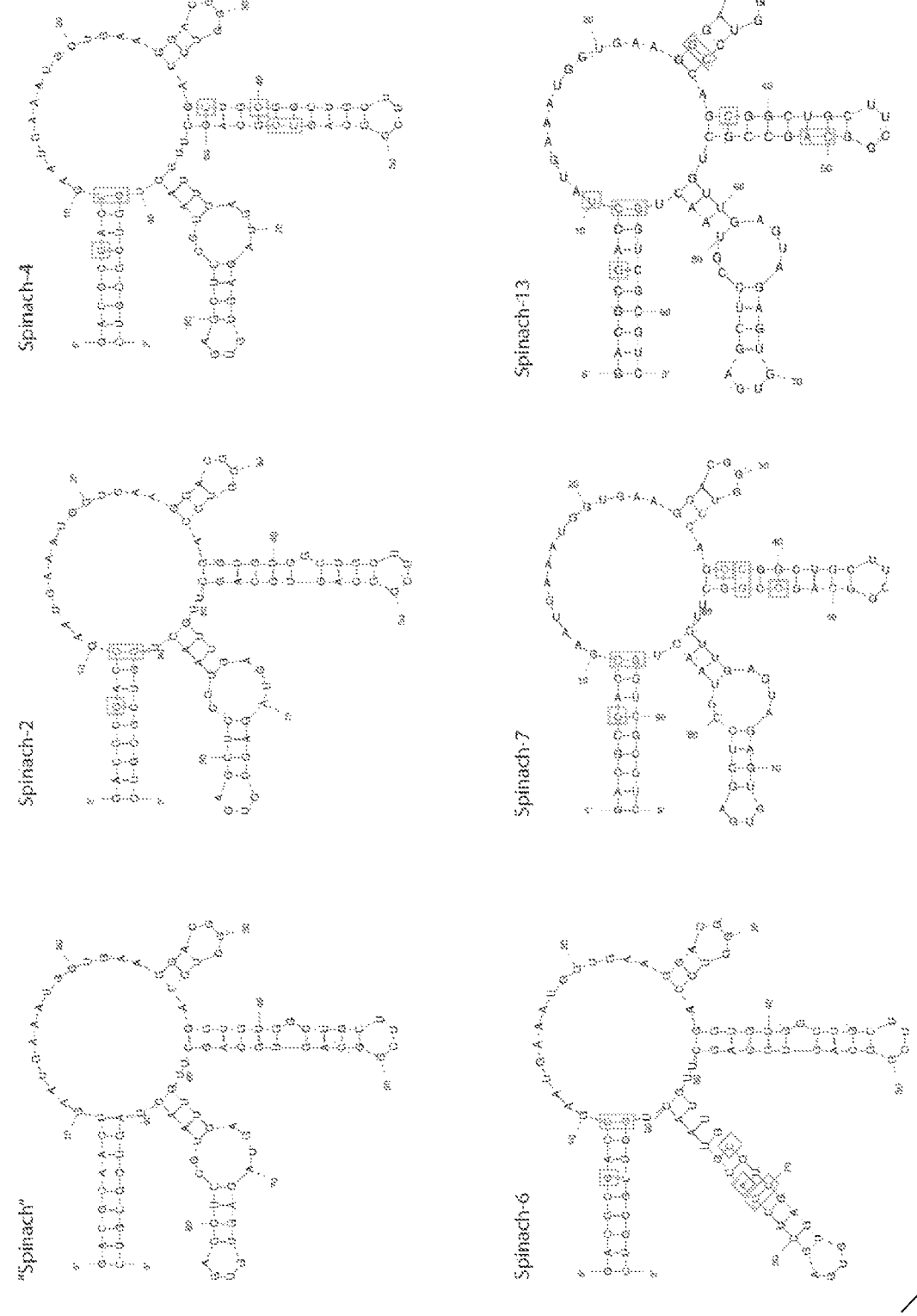
FIG. 17 illustrates the RNA sequences and secondary structures of Spinach (SEQ ID NO: 10), and five derivatives thereof, which are designated Spinach-2 (SEQ ID NO: 12), Spinach-4 (SEQ ID NO: 13), Spinach-6 (SEQ ID NO: 14), Spinach-7 (SEQ ID NO: 15), and Spinach-13 (SEQ ID NO: 11). RNA structure is shown as predicted by Mfold web-based software (Zuker, "Mfold Web Server for Nucleic Acid Folding and Hybridization Prediction," *Nucl. Acids Res.* 31(13): 3406-3415 (2003), which is hereby incorporated by reference in its entirety). Substitutions present in the derivatives, relative to Spinach, are shown with a box formed around the base.

Exemplary aptamers that bind to DFHBI include those of SEQ ID NOS: 5-10, 12, 13, and 15 (see FIGS. 1 and 17). Other aptamers that bind to DFHBI include those shown and described in PCT Application Publ. No. WO/2010/096584 to Jaffrey and Paige, which is hereby incorporated by reference in its entirety. One such aptamer is illustrated in FIG. 1 as SEQ ID NO: 4.

Exemplary aptamer molecules that bind specifically to the fluorophores DMHBI, HBI, and DMABI include those shown and described in PCT Application Publ. No. WO/2010/096584 to Jaffrey and Paige, which is hereby incorporated by reference in its entirety.

Additional exemplary aptamers include, without limitation, the following:

| Fluorophore | Aptamer Sequence |
|---|---|
| DFHO<br>Em = 550 nm<br>Ex = 480 nm | GGGAGACGCAACUGAAUGAAGUUGGCCCAUGAUAGAAAGCAGGGUG<br>CUGCUUCGGCAGUUGUCGGAGGGUGGGGGAUUGACUAUCCGUAAC<br>UAGUCGCGUCAC<br>(SEQ ID NO: 51) |
| DFHO<br>Em = 540 nm<br>Ex = 490 nm | GGGCGACUCACUAUAGGGAGACGCAACUGAAUGAAGCGAAGAAGGA<br>GGUCUGAGGAGGUCACUGCUUCGGCAGUGGGGCGUUUUCCCUGGGG<br>GUGUUGAUCCGUAACUAGUCGCGUCAC<br>(SEQ ID NO: 52) |
| DFHO<br>Em = 560 nm<br>Ex = 520 nm | GGGAGACGCAACUGAAUGAAAGACCUGACGAGGGUGAAGCGGUUGU<br>CUGCUUCGGCAGCAUUGAAAGGGUGGGGUGUAGGAUGGUCCGUAAC<br>UAGUCGCGUCAC<br>(SEQ ID NO: 53) |
| DFHO<br>Em = 545 nm<br>Ex = 500 nm | GGGAGACGCAACUGAAUGAAGCGAGGAAGGAGGUCUGAGGAGGUCA<br>CUGCUUCGACAGUGGGCGUUUUCCCUGGGGGUGUUGAUCCGUAAC<br>UAGUCGCGUCAC<br>(SEQ ID NO: 54) |
| MFHO<br>Em = 430 nm<br>Ex = 580 nm | GGGAGACGCAACUGAAUGAAGCGAGGAAGGAGGUCUGAGGAGGUCA<br>CUGCUUCGACAGUGGGCGUUUUCCCUGGGGGUGUUGAUCCGUAAC<br>UAGUCGCGUCAC<br>(SEQ ID NO: 55) |
| MFHO<br>Em = 570 nm<br>Ex = 550 nm | GGGAGACGCAACUGAAUGAAUGAGUAUGAUGCACGGUUAAAAUCCA<br>CUGCUUCGGCAGGAGUUGCGUUAGGAGGGUCGGGAGUCUCCGUAAC<br>UAGUCGCGUCAC<br>(SEQ ID NO: 56) |
| DFAME<br>Em = 570 nm<br>Ex = 620 nm | GGGAGACGCAACUGAAUGAAAGACCUGACGAGGGUGAAGCGGUUGU<br>CUGCUUCGGCAGCAUUGAAAGGGUGGGGUGUAGGAUGGUCCGUAAC<br>UAGUCGCGUCAC<br>(SEQ ID NO: 57) |
| DFAME<br>Em = 610 nm<br>Ex = 510 nm | GGGAGACGCAACUGAAUGAAGCCUCCGUGCGACAUCAUGCGCGCGA<br>CUGCUUCGGCAGAGGUGGGUGGUGUGGAGGAGUAUCUGUCCGUAAC<br>UAGUCGCGUCAC<br>(SEQ ID NO: 58) |
| DFAN<br>Em = 550 nm<br>Ex = 480 nm | GGGAGACGCAACUGAAUGAAAUACUUGGGAUGGUAAUGGCCUGGAG<br>CUGCUUCGGCAGACCCGUGCAAGGACGUGGGAGAGGGUCCGUAAC<br>UAGUCGCGUCAC<br>(SEQ ID NO: 59) |

The nucleic acid aptamers of the present invention include both monovalent aptamers that contain a single first domain for binding to the fluorophore, as well as multivalent aptamers that contain more than one aptamer domain.

According to one embodiment, the nucleic acid aptamer molecule can include a plurality of first domains for binding to multiple identical fluorophore compounds per molecule. These can be in the form of concatamers of a single type of aptamer that binds to a single fluorophore. Examples of these concatamers that are useful for expanding the fluorescent emissions per molecule include 2-mers, 4-mers, 8-mers, 12-mers, 16-mers, and 32-mers. In forming these concatamers, the plurality of aptamer domains can be separated by linker regions of a suitable length (e.g., about 30 to about 100 nts) that prevents steric or folding interference between the distinct aptamer domains, allowing each to properly fold and bind to their target fluorophores. Alternatively, the concatamers can contain multiple types of aptamers that bind to a several different fluorophores, and collectively achieve a blended emission profile.

According to another embodiment, the nucleic acid aptamer molecules can include one or more first domains that bind specifically to multiple identical fluorophore compounds per molecule, and one or more second domains that bind specifically to a target molecule of interest (i.e., one that is distinct of the fluorophore). Also contemplated herein are concatamers of these dual domain aptamer molecules, having the structure (first domain-second domain)$_m$, where m is an integer greater than 1. In these concatamers, the first domain of each functional two-domain sensor can be the same or different. Likewise, the second domain of each functional two-domain sensor can be the same or different. In another embodiment, the concatamer includes a plurality of first domains, which can be the same or different but bind specifically to the same fluorophore, and a single second domain that binds specifically to the target molecule of interest.

The target molecule of interest can be any biomaterial or small molecule including, without limitation, proteins, nucleic acids (RNA or DNA), lipids, oligosaccharides, carbohydrates, small molecules, hormones, cytokines, chemokines, cell signaling molecules, metabolites, organic molecules, and metal ions. The target molecule of interest can be one that is associated with a disease state or pathogen infection.

In one embodiment, the second domain is itself an aptamer that binds specifically to the target molecule.

In another embodiment, the second domain binds specifically to a target nucleic acid via hybridization (e.g., Watson-Crick base-pairing). Thus, the second domain has a nucleotide sequence that is sufficiently complementary to its target nucleic acid so as to hybridize under appropriate conditions with a target nucleic acid molecule that is physiologically found within a cell or within a biological sample. Upon hybridization between the second domain and the target, and the binding of the first domain to a fluorophore (introduced to the sample or cell), the target nucleic acid molecule is effectively labeled by the fluorophore. Presence of the target nucleic acid therefore can be detected based on the presence of fluorescence by the particular fluorophore employed.

Protein or polypeptide targets can be any length, and can include, without limitation, phosphoproteins, lipid-modified proteins, nitrosylated proteins, sulfenated proteins, acylated proteins, methylated proteins, demethylated proteins, C-terminal amidated proteins, biotinylated proteins, formylated proteins, gamma-carboxylated proteins, glutamylated proteins, glycylated proteins, iodinated proteins, hydroxylated proteins, isoprenylated proteins, lipoylated proteins (including prenylation, myristoylation, farnesylation, palmitoylation, or geranylation), proteins covalently linked to nucleotides such as ADP ribose (ADP-ribosylated) or flavin, oxidated proteins, proteins modified with phosphatidylinositol groups, proteins modified with pyroglutamate, sulfated proteins, selenoylated proteins, proteins covalently linked to another protein (including sumoylation, neddylation, ubiquitination, or ISGylation), citrullinated proteins, deamidated proteins, eliminylated proteins, disulfide bridged proteins, proteolytically cleaved proteins, proteins in which proline residues have been racemized, any peptides sequences that undergo the above mentioned modifications, and proteins which undergo one or more conformational changes. In addition, proteins or peptides that possess a mutation can be distinguished from wildtype forms. Complexes of two or more molecules include, without limitation, complexes have the following interactions: protein-protein, protein-cofactor, protein-inhibiting small molecules, protein-activating small molecules, protein-small molecules, protein-ion, protein-RNA, protein-DNA, DNA-DNA, RNA-DNA, RNA-RNA, modified nucleic acids-DNA or RNA, aptamer-aptamer. In addition, nucleic acids that possess a mutation can be distinguished from wildtype forms.

Nucleic acid targets can be any type of nucleic acid including, without limitation, DNA, RNA, LNA, PNA, genomic DNA, viral DNA, synthetic DNA, DNA with modified bases or backbone, mRNA, noncoding RNA, PIWI RNA, termini-associated RNA, promoter-associated RNA, tRNA, rRNA, microRNA, siRNA, post-transcriptionally modified RNA, synthetic RNA, RNA with modified bases or backbone, viral RNA, bacteria RNA, RNA aptamers, DNA aptamers, ribozymes, and DNAzymes.

Lipid targets include, without limitation, phospholipids, glycolipids, mono-, di-, tri-glycerides, sterols, fatty acyl lipids, glycerolipids, glycerophospholipids, sphingolipids, sterol lipids, prenol lipids, saccharolipids, polyketides, eicosanoids, prostaglandins, leukotrienes, thromboxanes, N-acyl ethanolamine lipids, cannabinoids, anandamides, terpenes, and lipopolysaccharides.

Small molecule targets include, without limitation, carbohydrates, monosaccharides, polysaccharides, galactose, fructose, glucose, amino acids, peptides, nucleic acids, nucleotides, nucleosides, cyclic nucleotides, polynucleotides, vitamins, drugs, inhibitors, single atom ions (such as magnesium, potassium, sodium, zinc, cobalt, lead, cadmium, etc.), multiple atom ions (such as phosphate), radicals (such as oxygen or hydrogen peroxide), and carbon-based gases (carbon dioxide, carbon monoxide, etc.).

Targets can also be whole cells or molecules expressed on the surface of whole cells. Exemplary cells include, without limitation, cancer cells, bacterial cells, or normal cells. Targets can also be viral particles.

A number of aptamers for these classes of target biomolecules have been identified previously, and can be incorporated into the multivalent nucleic acid aptamer constructs of the present invention. For example, other known RNA aptamers include, without limitation, RNA ligands of T4 DNA polymerase, RNA ligands of HIV reverse transcriptase, RNA ligands of bacteriophage R17 coat protein, RNA ligands for nerve growth factor, RNA ligands of HSV-1 DNA polymerase, RNA ligands of *Escherichia coli* ribosomal protein S1, and RNA ligands of HIV-1 Rev protein (U.S. Pat. No. 5,270,163 to Gold et al., which is hereby incorporated by reference in its entirety); RNA ligands of *Bacillus subtilis* ribonuclease P (U.S. Pat. No. 5,792,613 to Schmidt et al., which is hereby incorporated by reference); RNA ligands of ATP and RNA ligands of biotin (U.S. Pat. No. 5,688,670 to Szostak et al., which is hereby incorporated by reference in its entirety); RNA ligands of prion protein (Weiss et al., "RNA Aptamers Specifically Interact with the Prion Protein PrP," *J. Virol.* 71(11):8790-8797 (1997), which is hereby incorporated by reference in its entirety); RNA ligands of hepatitis C virus protein NS3 (Kumar et al., "Isolation of RNA Aptamers Specific to the NS3 Protein of Hepatitis C Virus from a Pool of Completely Random RNA," *Virol.* 237(2):270-282 (1997); Urvil et al., "Selection of RNA Aptamers that Bind Specifically to the NS3 Protein of Hepatitis C Virus," *Eur. J. Biochem.* 248(1):130-138 (1997); Fukuda et al., "Specific RNA Aptamers to NS3 Protease Domain of Hepatitis C Virus," *Nucleic Acids Symp. Ser.* 37:237-238 (1997), each of which is hereby incorporated by reference in its entirety); RNA ligands of chloramphenicol (Burke et al., "RNA Aptamers to the Peptidyl Transferase Inhibitor Chloramphenicol," *Chem. Biol.* 4(11):833-843 (1997), which is hereby incorporated by reference in its entirety); RNA ligands of the adenosine moiety of S-adenosyl methionine (Burke and Gold, "RNA Aptamers to the Adenosine Moiety of S-Adenosyl Methionine: Structural Inferences from Variations on a Theme and the Reproducibility of SELEX," *Nucleic Acids Res.* 25(10):2020-2024 (1997), which is hereby incorporated by reference in its entirety); RNA ligands of protein kinase C (Conrad et al., "Isozyme-Specific Inhibition of Protein Kinase C by RNA Aptamers," *J. Biol. Chem.* 269(51):32051-32054 (1994); Conrad and Ellington, "Detecting Immobilized Protein Kinase C Isozymes with RNA Aptamers," *Anal. Biochem.* 242(2):261-265 (1996), each which is hereby incorporated by reference in its entirety); RNA ligands of subtilisin (Takeno et al., "RNA Aptamers of a Protease Subtilisin," *Nucleic Acids Symp. Ser.* 37:249-250 (1997), which is hereby incorporated by reference in its entirety); RNA ligands of yeast RNA polymerase II (Thomas et al., "Selective Targeting and Inhibition of Yeast RNA Polymerase II by RNA Aptamers," *J. Biol. Chem.* 272(44): 27980-27986 (1997), which is hereby incorporated by reference in its entirety); RNA ligands of human activated protein C (Gal et al., "Selection of a RNA Aptamer that Binds to Human Activated Protein C and Inhibits its Protein Function," *Eur. J. Biochem.* 252(3):553-562 (1998), which is hereby incorporated by reference in its entirety); and RNA ligands of cyanocobalamin (Lorsch and Szostak, "In vitro Selection of RNA Aptamers Specific for Cyanocobalamin," *Biochem.* 33(4):973-982 (1994), which is hereby incorporated by reference in its entirety). Additional RNA aptamers are continually being identified and isolated by those of ordinary skill in the art, and these, too, can be incorporated into the multivalent aptamer constructs of the present invention.

According to one embodiment, the multivalent nucleic acid aptamer molecules of the invention include a first domain that binds to the fluorophore substantially only after the second domain binds to the target molecule. As demonstrated in the examples, in multivalent nucleic acid aptamer molecules of this type, the second domain possesses a stable structure and is capable of binding to the target molecule, whereas the first domain or regions of the nucleic acid molecule adjacent to the first domain possess a structure that is substantially incapable of binding the fluorophore (or does so with reduced affinity). Upon binding of the target molecule by the second domain, however, the secondary structure of the first domain is altered and adopts a structure that is capable of binding the fluorophore with sufficiently high affinity. As a consequence of target molecule binding, the fluorophore becomes bound by the first domain and upon exposure to radiation of appropriate wavelength emits a fluorescent emission signal. Multivalent aptamers of this type can be used as "turn-on" sensors.

Figure 7A:
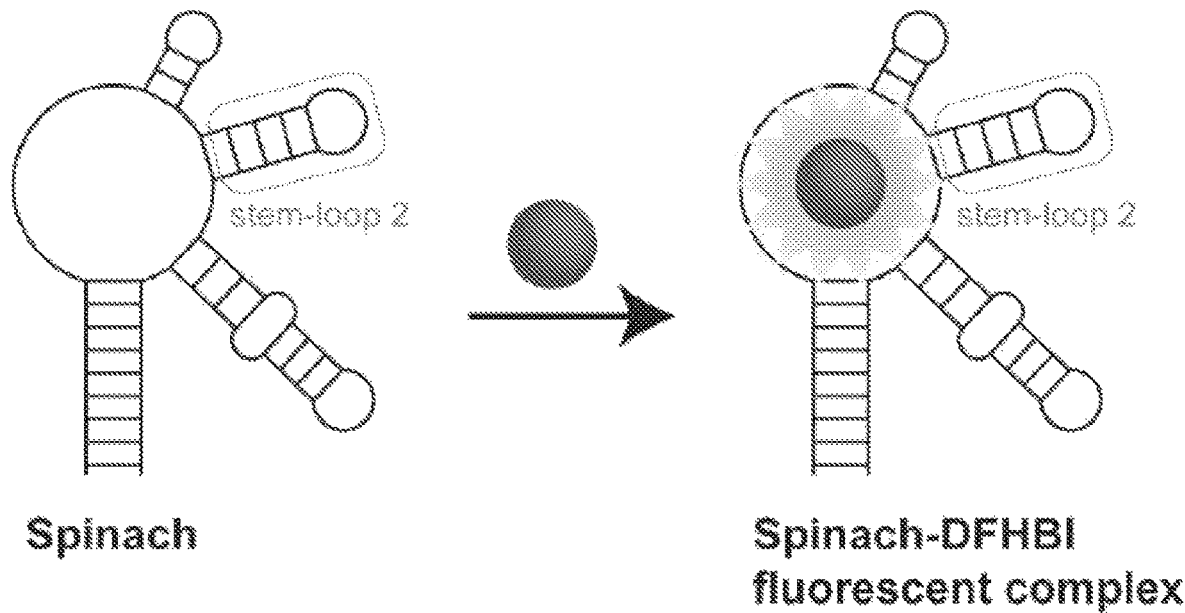
FIGS. 7A-C illustrate the design of modular Spinach-based fluorescent sensors.
Figure 7B:
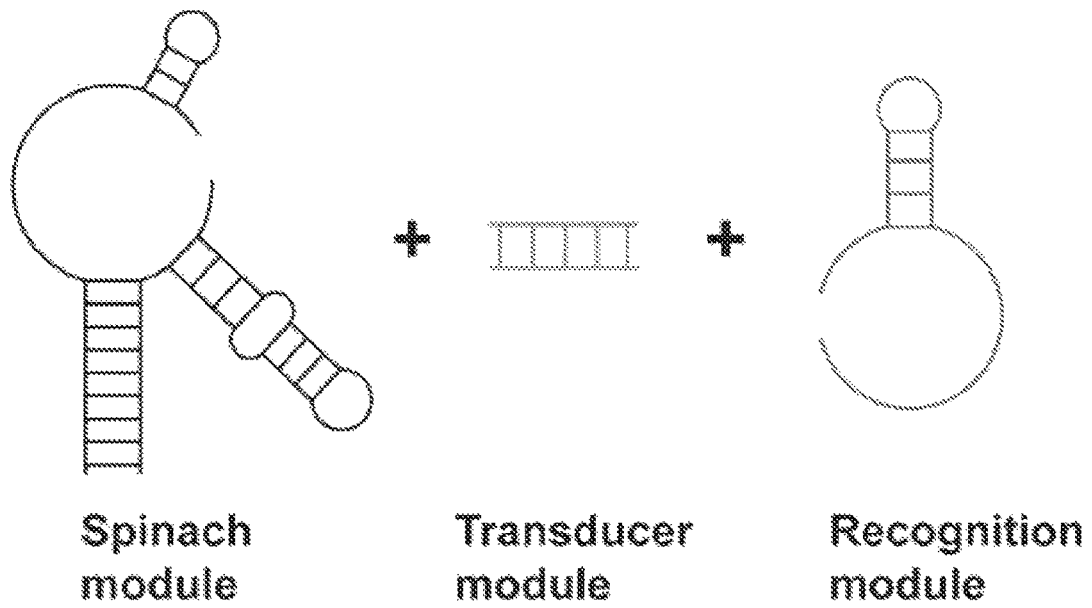
Figure 7C:
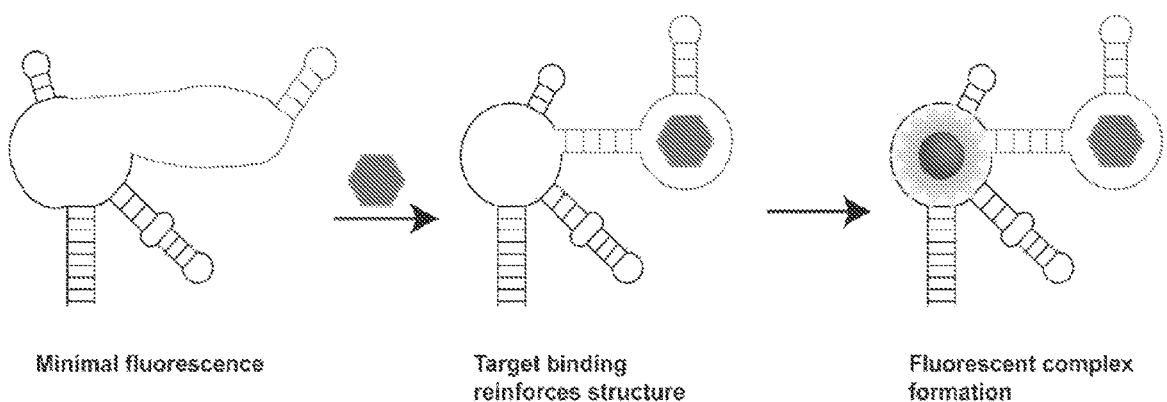

As illustrated in FIGS. 7B-C, to facilitate the ability of these sensors to "turn-on" in the presence of the target analyte, the aptamer for the target molecule can be coupled at its 5' and 3' ends to the aptamer specific for the fluorophore via a transducer molecule. The transducer molecule includes a pair of antiparallel stem-forming sequences, one coupled by phosphodiester bond between a first portion of the fluorophore-specific aptamer and a 5' end of the target-binding aptamer, and the other coupled by phosphodiester bond between a second portion of the fluorophore-specific aptamer and a 3' end of the target-binding aptamer. The transducer molecule preferably includes one or more mismatched base pairs or an overall low number of base pairs (e.g., one or two base pairs) such that stem formation of the transducer molecule is thermodynamically unfavorable in the absence of target molecule binding to the target-binding aptamer, and thermodynamically favorable after target molecule binding to the target-binding aptamer.

As demonstrated in the accompanying examples, multivalent aptamer sensors of this embodiment have been developed that are specific for the biomolecules ADP, adenosine, guanine, GTP, SAM, and streptavidin.

An exemplary "turn-on" sensor for adenosine has the nucleotide sequence according to SEQ ID NO: 18 as follows:

```
GACGCGACUG AAUGAAAUGG UGAAGGACGG GUCCAGUAAU

GGGAAGAAAC UGUGGCACUU CGGUGCCAGC GUUGCUUGUU

GAGUAGAGUG UGAGCUCCGU AACUAGUCGC GUC
```

In this sensor, nts 1-35 and 76-113 (bold) correspond to the DFHBI aptamer, nts 36-41 and 70-75 (italics) correspond to the transducer molecule, and nts 42-69 correspond to the adenosine aptamer.

An exemplary "turn-on" sensor for ADP has the nucleotide sequence according to SEQ ID NO: 26 as follows:

```
GACGCGACUG AAUGAAAUGG UGAAGGACGG GUCCAGCACG

AGGGGGAAAC CCCGGACAAU CAGACACGGU GCUUGUUGAG

UAGAGUGUGA GCUCCGUAAC UAGUCGCGUC
```

In this sensor, nts 1-35 and 73-110 (bold) correspond to the DFHBI aptamer, nts 36-39 and 68-72 (italics) correspond to the transducer molecule, and nts 40-67 correspond to the ADP aptamer.

An exemplary "turn-on" sensor for guanine has the nucleotide sequence according to SEQ ID NO: 42 as follows:

```
GACGCGACUG AAUGAAAUGG UGAAGGACGG GUCCAGAUAA

UCGCGUGGAU AUGGCACGCA AGUUUCUACC GGGCACCGUA

AAUGUCCGAC UCUUGUUGAG UAGAGUGUGA GCUCCGUAAC

UAGUCGCGUC
```

In this sensor, nts 1-35 and 93-130 (bold) correspond to the DFHBI aptamer, nts 36-37 and 91-92 (italics) correspond to the transducer molecule, and nts 38-90 correspond to the guanine aptamer.

An exemplary "turn-on" sensor for GTP has the nucleotide sequence according to SEQ ID NO: 43 as follows:

```
GACGCGACUG AAUGAAAUGG UGAAGGACGG GUCCAGCAGA

AGAGCACGUA UACGCAAGCU UGUUGAGUAG AGUGUGAGCU

CCGUAACUAG UCGCGUC
```

In this sensor, nts 1-35 and 60-97 (bold) correspond to the DFHBI aptamer, nts 36-37 and 58-59 (italics) correspond to the transducer molecule, and nts 38-57 correspond to the GTP aptamer.

An exemplary "turn-on" sensor for SAM has the nucleotide sequence according to SEQ ID NO: 32 as follows:

```
GACGCGACUG AAUGAAAUGG UGAAGGACGG GUCCACGAAA

GGAUGGCGGA AACGCCAGAU GCCUUGUAAC CGAAAGGGUU

GUUGAGUAGA GUGUGAGCUC CGUAACUAGU CGCGUC
```

In this sensor, nts 1-35 and 79-116 (bold) correspond to the DFHBI aptamer, nts 36 and 78 (italics) correspond to the transducer molecule, and nts 37-77 correspond to the SAM aptamer.

An exemplary "turn-on" sensor for streptavidin has the nucleotide sequence according to SEQ ID NO: 44 as follows:

```
GACGCGACUG AAUGAAAUGG UGAAGGACGG GUCCACGACC

GACCAGAAUC AUGCAAGUGC GUAAGAUAGU CGCGGGCCGG

GGUUGUUGAG UAGAGUGUGA GCUCCGUAAC UAGUCGCGUC
```

In this sensor, nts 1-35 and 83-120 correspond to the DFHBI aptamer and nts 36-82 (italics) correspond to the streptavidin aptamer. In this embodiment, the transducer molecule, forming the partially destabilized stem of stem-loop 2, was present in the original streptavidin aptamer.

According to another embodiment, the multivalent nucleic acid aptamer molecule of the invention includes a first domain that binds to the fluorophore substantially only in the absence of the second domain binding to the target molecule. In multivalent nucleic acid aptamer molecules of this type, the second domain possesses a stable structure and is capable of binding to the target molecule, and the first domain or regions of the nucleic acid molecule adjacent to the first domain possess a structure that is capable of binding the fluorophore with sufficiently high affinity. Upon binding of the target molecule by the second domain, however, the secondary structure of the first domain is altered and adopts a structure that is substantially incapable of binding the fluorophore with high affinity. As a consequence of target molecule binding, the fluorophore dissociates from the first domain and despite exposure to radiation of appropriate wavelength the fluorophore will no longer emit a fluorescent emission signal (or emits only a substantially diminished level of fluorescent emissions). Multivalent aptamers of this type can be used as "turn-off" sensors.

As discussed below, the monovalent aptamers and aptamer constructs of the invention can be used as sensors for tracking the presence, location, or quantity of a fused nucleic acid molecule of interest in a cell or an in vitro sample; for determining the presence, location, or quantity of a target molecule of interest in a cell or an in vitro sample; for high throughput screening assays to assess the ability of an agent to modulate certain cellular functions, such as transcription levels or splicing, or for modulating the activity or availability of a target molecule; for microarray detection of analytes or genes of interest; and de novo screening of sensor molecules for particular targets of interest using a modified SELEX.

In many of these aptamer constructs, where a single fluorophore binding domain is used, the single fluorophore binding domain can be replaced with a concatamer containing multiple fluorophore binding domains. For example, multiple fluorophore binding sequences, e.g., 8, 12, 16, 20, 24, or more, can be linked together in series with adjacent fluorophore binding sequences separated by a spacer sequence that is sufficiently long (e.g., 30 to 100 nucleotides) so as to inhibit interference between adjacent fluorophore binding sequences. In certain embodiments, the fluorophore binding sequences can be slightly different from one another other (or at least relative to immediately adjacent fluorophore binding sequences) to ensure that each aptamer sequence self-hybridizes to fold properly rather than hybridize with other aptamer sequences. Because each individual aptamer sequence within the concatamer is capable of binding to its fluorophore, use of the concatamer is expected to increase the fluorescence per aptamer construct. In this way, it is possible to design aptamer constructs where as few as a single molecule can be detected.

The nucleic acid aptamer molecules of the present invention can also be directed to specific cellular locations by creating a nucleic acid fusion with a particular signaling molecule or signal-interacting molecule.

According to another embodiment, a nucleic acid aptamer construct of the invention includes one or more first domains that bind specifically to multiple identical fluorophore compounds per molecule, and a second domain that includes a random nucleotide sequence.

By "random," it is contemplated that the entirety of the second domain, or merely a portion thereof, contains a nucleotide sequence that is not known a priori, but rather is generated randomly. Thus, a portion of the second domain may contain a known sequence, but the entirety of the second domain sequence is not known. Multivalent aptamer constructs of this type are prepared as "turn-on" sensors, as described above, and are useful for de novo screening and identification of aptamers having affinity for a target molecule of interest. These multivalent nucleic acid aptamer constructs can be generated during a modified SELEX process as described hereinafter. Thus, the present invention also encompasses a library of these multivalent nucleic acid aptamer constructs. In the library, each member of the initial library preferably contains a unique or substantially unique random sequence (i.e., shared by few, if any, other initial library members).

Molecular Complexes

A further aspect of the invention relates to molecular complexes that are formed using the fluorescent compounds and nucleic acid aptamers of the present invention, which are specifically bound to the fluorescent compounds such that the fluorophore has substantially enhanced fluorescence (i.e., in comparison to the fluorophore prior to specific binding) upon exposure to radiation of suitable wavelength.

According to one embodiment, the nucleic acid molecule includes one or more first domains, as described above, and the molecular complex is therefore formed by the nucleic acid molecule and one or more fluorescent compounds that are bound to at least one, and optionally all, of the first domains present in the nucleic acid molecule. These molecular complexes can exist in vitro, in isolated form, or in vivo following introduction of the nucleic acid molecule (or a genetic construction or expression system encoding the same) into a host cell.

According to another embodiment, the nucleic acid molecule includes one or more first domains and a second domain that binds specifically to a target molecule of interest. The molecular complex, therefore, can include the nucleic acid molecule, the target molecule (bound specifically by the second domain), and one or more fluorescent compounds that are bound to the first domain(s). These molecular complexes can exist in vitro, in isolated form or tethered to a substrate such as on an arrayed surface, or in vivo following introduction of the nucleic acid molecule (or a genetic construction or expression system encoding the same) into a host cell.

According to another embodiment, the nucleic acid molecule includes a plurality of aptamer sensor concatamers, each monomer including a first domain and a second domain. The molecular complex, therefore, can include the nucleic acid molecule, a plurality of target molecules (bound specifically by the plurality of second domains), and a plurality of fluorescent compounds that are bound to the plurality of first domain(s). These molecular complexes can exist in vitro, in isolated form or tethered to a substrate such as on an arrayed surface, or in vivo following introduction of the nucleic acid molecule (or a genetic construction or expression system encoding the same) into a host cell.

According to another embodiment, the nucleic acid molecule includes an aptamer sequence linked to a hybridization probe sequence that is complementary to a target nucleic acid molecule. The molecular complex, therefore, can include the nucleic acid molecule hybridized to the target nucleic acid molecule, and one or more fluorophores bound specifically to the fluorophore-specific aptamer domain. These molecular complexes can exist in vitro, in isolated form or tethered to a substrate such as on an arrayed surface, or in vivo following introduction of the nucleic acid molecule (or a genetic construction or expression system encoding the same) into a host cell. In certain embodiments, these complexes can exist in fixed cells or on histologic tissue sections in the manner of an in situ hybridization protocol.

Specific examples of these types of molecular complexes, formed in vitro and in vivo, are disclosed in the accompanying Examples. Although in vitro host cells are described in the accompanying Examples, it should be appreciated to skilled artisans that the host cells can be present in a whole organism, preferably a non-human organism.

For formation of the molecular complex inside a cell, the fluorophore is introduced into the cell where it can interact with (and be bound by) the aptamer that specifically binds to it. According to one approach, the cell or the sample is contacted with the fluorophore by incubating the cell or the sample with the fluorophore. The fluorophore will be taken up by the cell, where it may freely diffuse throughout the cell. According to another approach, the fluorophore is injected into the cell or administered to a plant, embryo, mammal, or transgenic animal including the cell.

Genetic Constructs

While the RNA aptamer molecules of the present invention can be synthesized from chemical precursor, they also can be prepared either in vitro or in vivo using recombinant templates or constructs, including transgenes, that encode the RNA aptamer molecules of the present invention. Whether using in vitro transcription or transgenes suitable for expression in vivo, these genetic constructs can be prepared using well known recombinant techniques.

A further aspect of the present invention relates to a constructed DNA molecule that includes a first region encoding an RNA aptamer molecule of the invention.

According to one embodiment, the constructed DNA molecule encodes an RNA fusion product. Such a product is formed by joining together one piece of DNA encoding an RNA molecule of interest and a second piece of DNA encoding an RNA aptamer molecule that binds specifically to a fluorophore of the invention. As described above, the RNA aptamer molecule can be in the form of a concatamer that contains multiple fluorophore-binding domains.

According to another embodiment, the constructed DNA molecule encodes a molecular sensor of the invention, which is formed by joining together one piece of DNA encoding an RNA aptamer molecule that is specific for a target molecule and a second piece of DNA encoding an RNA aptamer molecule that binds specifically to a fluorophore of the invention, and optionally a third piece of DNA encoding the transducer molecule. The conjoined RNA sequences can cooperate in the manner described above, so as to achieve a "turn-on" sensor or "turn-off" sensor.

According to yet another embodiment, an empty construct can be prepared for preparation of an RNA fusion product. Such an empty construct includes a DNA sequence encoding an RNA aptamer molecule that binds specifically to a fluorophore of the invention, along with appropriate regulatory sequences (discussed below), and a restriction enzyme insertion site that can be used for subsequent insertion of a desired DNA molecule (encoding an RNA molecule of interest). As described above, the RNA aptamer molecule can include a concatamer of fluorophore-binding domains. The restriction enzyme insertion site can include one or more enzymatic cleavage sites to facilitate insertion of virtually any DNA coding sequence as desired. The restriction enzyme insertion site is preferably located between the promoter sequence and the aptamer-encoding DNA sequence.

According to a further embodiment, the constructed DNA molecule encodes an RNA aptamer of the invention, however, within the region encoding the RNA aptamer, an intron is positioned therein. This spatially segregates the RNA aptamer-encoding regions, whereby transcription in the absence of a proper spliceosome will not afford a functional aptamer molecule. In the presence of a proper spliceosome, excision of the intron from a transcript of the constructed DNA molecule affords the RNA aptamer molecule of the invention. This will allow the RNA aptamer to bind to the fluorophore to induce fluorescence.

In an alternative embodiment, the sequences within the intron contribute to the fluorophore-binding aptamer, whereby prior to splicing the RNA molecule is capable of exhibiting fluorescence when bound to the fluorophore. However, in the presence of a proper spliceosome, splicing of the RNA molecule destroys the fluorophore-binding aptamer, thereby inhibiting fluorescence.

Preparation of the DNA molecule can be carried out by well-known methods of DNA ligation. DNA ligation utilizes DNA ligase enzymes to covalently link or ligate fragments of DNA together by catalyzing formation of a phosphodiester bond between the 5' phosphate of one strand of DNA and the 3' hydroxyl of another. Typically, ligation reactions require a strong reducing environment and ATP. The commonly used T4 DNA ligase is an exemplary DNA ligase in preparing the DNA molecule of the present invention. Once the DNA molecule of the present invention has been constructed, it can be incorporated into host cells as described infra.

Transcription of the DNA molecule of the present invention is often dependent upon the presence of a promoter, which is a DNA sequence that directs the binding of RNA polymerase and thereby promotes RNA synthesis. Accordingly, the DNA molecule of the present invention may include a promoter operably coupled to the first region to control expression of the RNA aptamer. Because not all polymerases require promoters, the promoter sequence is optional.

The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters are not recognized and do not function in eukaryotic cells.

Promoters vary in their "strength" (i.e., their ability to promote transcription). Depending on the application, it may be desirable to use strong promoters in order to obtain a high level of transcription. For instance, when used simply as a label high expression levels may be preferred, whereas to assess transcript behavior it may be desirable to obtain lower levels of expression that allow the cell to process the transcript.

Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV 5, ompF, bla, lpp, and the like, may be used to direct high levels of transcription of adjacent DNA segments. Additionally, a hybrid trp-lacUV 5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

As described above, one type of regulatory sequence is a promoter located upstream or 5' to the coding sequence of the DNA molecule. Depending upon the desired activity, it is possible to select the promoter for not only in vitro production of the RNA aptamer, but also in vivo production in cultured cells or whole organisms, as described below. Because in vivo production can be regulated genetically, another suitable class of promoters is an inducible promoter which induces transcription of the DNA molecule in response to specific conditions, thereby enabling expression of the RNA aptamer as desired (i.e., expression within specific tissues, or at specific temporal and/or developmental stages). The various promoter types can be driven by RNA polymerases I, II, or III.

Suitable promoters for use with the constructed DNA molecule of the present invention include, without limitation, a T7 promoter, a SUP4 tRNA promoter, an RPR1 promoter, a GPD promoter, a GAL1 promoter, an hsp70 promoter, an Mtn promoter, a UAShs promoter, and functional fragments thereof. The T7 promoter is a well-defined, short DNA sequence that can be recognized and utilized by T7 RNA polymerase of the bacteriophage T7. The T7 RNA polymerase can be purified in large scale and is commercially available. The transcription reaction with T7 promoter can be conducted in vitro to produce a large amount of the molecular complex of the present invention (Milligan et al., "Oligoribonucleotide Synthesis Using T7 RNA Polymerase and Synthetic DNA Templates," *Nucleic Acids Res.* 15(21): 8783-8798 (1987), which is hereby incorporated by reference in its entirety). The T7 RNA polymerase can also be used in mammalian and bacterial cells to produce very high levels of RNA. The SUP4 tRNA promoter and RPR1 promoter are driven by RNA polymerase III of the yeast *Saccharomyces cerevisiae*, and suitable for high level expression of RNA less than 400 nucleotides in length (Kurjan et al., Mutation at the Yeast SUP4 tRNA$^{tyr}$ Locus: DNA Sequence Changes in Mutants Lacking Suppressor Activity," *Cell* 20:701-709 (1980); Lee et al., "Expression of RNase P RNA in *Saccharomyces cerevisiae* is Controlled by an Unusual RNA Polymerase III Promoter," *Proc. Natl. Acad. Sci. USA* 88:6986-6990 (1991), each of which is hereby incorporated by reference in its entirety). The glyceraldehyde-3-phosphate dehydrogenase (GPD) promoter in yeast is a strong constitutive promoter driven by RNA polymerase II (Bitter et al., "Expression of Heterologous Genes in *Saccharomyces cerevisiae* from Vectors Utilizing the Glyceraldehyde-3-phosphate Dehydrogenase Gene Promoter," Gene 32:263-274 (1984), which is hereby incorporated by reference in its entirety). The galactokinase (GAL1) promoter in yeast is a highly inducible promoter driven by RNA polymerase II (Johnston and Davis, "Sequences that Regulate the Divergent GAL1-GAL10 Promoter in *Saccharomyces cerevisiae,*" *Mol. Cell. Biol.* 4:1440-1448 (1984), which is hereby incorporated by reference in its entirety). The heat shock promoters are heat inducible promoters driven by the RNA polymerase II in eukaryotes. The frequency with which RNA polymerase II transcribes the major heat shock genes can be increased rapidly in minutes over 100-fold upon heat shock. Another inducible promoter driven by RNA polymerase II that can be used in the present invention is a metallothionine (Mtn) promoter, which is inducible to the similar degree as the heat shock promoter in a time course of hours (Stuart et al., "A 12-Base-Pair Motif that is Repeated Several Times in Metallothionine Gene Promoters Confers Metal Regulation to a Heterologous Gene," *Proc. Natl. Acad. Sci. USA* 81:7318-7322 (1984), which is hereby incorporated by reference in its entirety).

Initiation of transcription in mammalian cells requires a suitable promoter, which may include, without limitation, β-globin, GAPDH, β-actin, actin, Cstf2t, SV40, MMTV, metallothionine-1, adenovirus E1a, CMV immediate early, immunoglobulin heavy chain promoter and enhancer, and RSV-LTR. Termination of transcription in eukaryotic genes involves cleavage at a specific site in the RNA which may precede termination of transcription. Also, eukaryotic termination varies depending on the RNA polymerase that transcribes the gene. However, selection of suitable 3' transcription termination regions is well known in the art and can be performed with routine skill.

Spatial control of an RNA molecule can be achieved by tissue-specific promoters, which have to be driven by the RNA polymerase II. The many types of cells in animals and plants are created largely through mechanisms that cause different genes to be transcribed in different cells, and many specialized animal cells can maintain their unique character when grown in culture. The tissue-specific promoters involved in such special gene switching mechanisms, which are driven by RNA polymerase II, can be used to drive the transcription templates that code for the molecular complex of the present invention, providing a means to restrict the expression of the molecular complex in particular tissues. Any of a variety of tissue-specific promoters can be selected as desired.

For gene expression in plant cells, suitable promoters may include, without limitation, nos promoter, the small subunit ribulose bisphosphate carboxylase genes, the small subunit chlorophyll A/B binding polypeptide, the 35S promoter of cauliflower mosaic virus, and promoters isolated from plant genes, including the Pto promoter itself (See Vallejos, et al., "Localization in the Tomato Genome of DNA Restriction Fragments Containing Sequences Homologous to the $_r$RNA (45S), the major chlorophyll$_{A/B}$ Binding Polypeptide and the Ribulose Bisphosphate Carboxylase Genes," *Genetics* 112: 93-105 (1986) (disclosing the small subunit materials), which is hereby incorporated by reference in its entirety). The nos promoter and the 35S promoter of cauliflower mosaic virus are well known in the art.

In addition, the constructed DNA molecule may also include an operable 3' regulatory region, selected from among those which are capable of providing correct transcription termination and polyadenylation of mRNA for expression in plant cells. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l. Acad. Sci. USA,* 80:4803-4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature,* 313(6005):810-812 (1985), which is hereby incorporated by reference in its entirety). Virtually any 3' regulatory region known to be operable in plants would suffice for proper expression of the coding sequence of the constructed DNA molecule of the present invention.

Another type of regulatory sequence is known as an enhancer. Enhancer elements do not need to be located immediately upstream of the promoter or the sequence which encodes the transcript that will be made. Enhancers can, in fact, be located very far away. Nevertheless, they can also serve as regulatory elements, and could potentially be regulated by signaling molecules and thereby influence the expression of a target RNA inside a cell. Exemplary enhancer elements include, without limitation, the well-known SV40 enhancer region and the 35S enhancer element.

Once the DNA molecule of the present invention has been constructed, it can be incorporated into cells using conventional recombinant DNA technology. Generally, this involves inserting the DNA molecule into an expression system to which the DNA molecule is heterologous (i.e., not normally present). The heterologous DNA molecule is inserted into the expression system or vector in proper sense orientation. The vector contains the necessary elements for their persistent existence inside cells and for the transcription of an RNA molecule that can be translated into the molecular complex of the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and transfection, and replicated in cultures including prokaryotic organisms and eukaryotic cells grown in tissue culture.

Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see Studier et al., "Use of T7 RNA Polymerase to Direct Expression of Cloned Genes," *Gene Expression Technology*, vol. 185 (1990), which is hereby incorporated by reference in its entirety), pIIIEx426 RPR, pIIIEx426 tRNA (see Good and Engelke, "Yeast Expression Vectors Using RNA Polymerase III Promoters," *Gene* 151:209-214 (1994), which is hereby incorporated by reference in its entirety), p426GPD (see Mumberg et al., "Yeast Vectors for the Controlled Expression of Heterologous Proteins in Different Genetic Background," *Gene* 156: 119-122 (1995), which is hereby incorporated by reference in its entirety), p426GAL1 (see Mumberg et al., "Regulatable Promoters of *Saccharomyces cerevisiae*: Comparison of Transcriptional Activity and Their Use for Heterologous Expression," *Nucl. Acids Res.* 22:5767-5768 (1994), which is hereby incorporated by reference in its entirety), pUAST (see Brand and Perrimon, "Targeted Gene Expression as a Means of Altering Cell Fates and Generating Dominant Phenotypes," *Development* 118:401-415 (1993), which is hereby incorporated by reference in its entirety), and any derivatives thereof. Suitable vectors are continually being developed and identified.

A variety of host-vector systems may be utilized to express the DNA molecule. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, retroviral vectors, etc.); insect cell systems infected with virus (e.g., baculovirus); and plant cells infected by bacteria or transformed via particle bombardment (i.e., biolistics). The expression elements of these vectors vary in their strength and specificities. Depending upon the host-vector system utilized, any one of a number of suitable transcription elements can be used.

Once the constructed DNA molecule has been cloned into an expression system, it is ready to be incorporated into a host cell. Such incorporation can be carried out by the various forms of transformation, depending upon the vector/host cell system such as transformation, transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference in its entirety. Suitable host cells include, but are not limited to, bacteria, yeast, mammalian cells, insect cells, plant cells, and the like. The host cell is preferably present either in a cell culture (ex vivo) or in a whole living organism (in vivo).

Mammalian cells suitable for carrying out the present invention include, without limitation, COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, NS-1 cells, embryonic stem cells, induced pluripotent stem cells, and primary cells recovered directly from a mammalian organism. With regard to primary cells recovered from a mammalian organism, these cells can optionally be reintroduced into the mammal from which they were harvested or into other animals.

The expression of high levels of functional RNA aptamers within cells can be complicated by several factors including RNA stability, short half-life, and difficulties in cellular targeting. Nonetheless, substantial progress has been achieved over the last several years. The first demonstration of aptamer function in live cells involved nuclear targets (Klug et al., "In Vitro and In Vivo Characterization of Novel mRNA Motifs that Bind Special Elongation Factor SelB," *Proc. Natl. Acad. Sci. USA* 94:6676-6681 (1997); Shi et al., "RNA Aptamers as Effective Protein Antagonists In a Multicellular Organism," *Proc. Natl. Acad. Sci. USA* 96:10033-10038 (1999); Thomas et al., "Selective Targeting and Inhibition of Yeast RNA Polymerase II by RNA Aptamers," *J. Biol. Chem.* 272: 27980-27986 (1997), which are hereby incorporated by reference in their entirety). Aptamer function within the nucleus of mammalian cells has also been demonstrated (Symensma et al., "Polyvalent Rev Decoys Act as Artificial Rev-Responsive Elements," *J. Virol.* 73:4341-4349 (1999), which is hereby incorporated by reference in its entirety). More recently, effective strategies for cytoplasmic targeting of aptamer have also been developed. For example, the human tRNA initiator sequence, which mediates highly efficient nuclear export to deliver functional chimeric RNA aptamers to the cytosol has been used (Chaloin et al., "Endogenous Expression of a High-Affinity Pseudoknot RNA Aptamer Suppresses Replication of HIV-1," *Nucl. Acids Res.* 30:4001-4008 (2002), which is hereby incorporated by reference in its entirety). Functional RNA aptamers have also been directly delivered to the cytoplasm by lipofection (Theis et al., "Discriminatory Aptamer Reveals Serum Response Element Transcription Regulated by Cytohesin-2," *Proc. Natl. Acad. Sci. USA* 101:11221-11226 (2004), which is hereby incorporated by reference in its entirety). Finally, most recently, very high levels of aptamer expression ($1\times10^7$ molecules per cell) have been achieved by fusion with a highly stable transcript (Choi et al., "Intracellular Expression of the T-cell Factor-1 RNA Aptamer as an Intramer," *Mol. Cancer Ther.* 5:2428-2434 (2006), which is hereby incorporated by reference in its entirety).

Plant tissues suitable for transformation include leaf tissue, root tissue, meristems, zygotic and somatic embryos, and anthers. It is particularly preferred to utilize embryos obtained from anther cultures. The expression system of the present invention can be used to transform virtually any plant tissue under suitable conditions, and the transformed cells can be regenerated into whole plants.

One approach to transforming plant cells and/or plant cell cultures, tissues, suspensions, etc. with a DNA molecule of the present invention is particle bombardment (also known as biolistic transformation) of the host cell. This technique is disclosed in U.S. Pat. Nos. 4,945,050, 5,036,006, and 5,100,792, all to Sanford, et al., which are hereby incorporated by reference in their entirety. Another method of introducing DNA molecules into a host cell is fusion of protoplasts with other entities, either minicells, cells, lysosomes, or other fusible lipid-surfaced bodies that contain the DNA molecule (Fraley et al., "Expression of Bacterial Genes in Plant Cells," *Proc. Natl. Acad. Sci. USA* 80:4803-4807 (1983), which is hereby incorporated by reference in its entirety). The DNA molecule of the present invention may also be introduced into the plant cells and/or plant cell cultures, tissues, suspensions, etc. by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety).

In producing transgenic plants, the DNA construct in a vector described above can be microinjected directly into plant cells by use of micropipettes to transfer mechanically the recombinant DNA (Crossway, "Integration of Foreign DNA Following Microinjection of Tobacco Mesophyll Protoplasts," *Mol. Gen. Genetics* 202:179-85 (1985), which is hereby incorporated by reference in its entirety). The genetic material may also be transferred into the plant cell using polyethylene glycol (Krens et al., "In Vitro Transformation of Plant Protoplasts with Ti-Plasmid DNA," *Nature* 296:72-74 (1982), which is hereby incorporated by reference in its entirety). Alternatively, genetic sequences can be introduced into appropriate plant cells by means of the Ti plasmid of *A. tumefaciens* or the Ri plasmid of *A. rhizogenes*, which is transmitted to plant cells on infection by *Agrobacterium* and is stably integrated into the plant genome (Schell, "Transgenic Plants as Tools to Study the Molecular Organization of Plant Genes," *Science* 237:1176-83 (1987), which is hereby incorporated by reference in its entirety). After transformation, the transformed plant cells must be regenerated, and this can be accomplished using well known techniques as described in Evans et al., *Handbook of Plant Cell Cultures*, Vol. 1, MacMillan Publishing Co., New York (1983); and Vasil (ed.), *Cell Culture and Somatic Cell Genetics of Plants*, Acad. Press, Orlando, Vol. I (1984) and Vol. III (1986), each of which is hereby incorporated by reference in its entirety.

Methods of Use

In the various methods of use, the formation of molecular complexes of the invention (e.g., fluorophore:aptamer complexes or fluorophore:aptamer:target complexes) can be identified, quantified, and monitored for various purposes, as discussed more fully below. Detection of molecular complex formation, through the fluorescent output of the fluorophore or a FRET partner (e.g., donor or acceptor), can be used to detect complex formation in a cell-free sample (e.g., cell extracts, fractions of cell extracts, or cell lysates), histological or fixed samples, tissues or tissue extracts, bodily fluids, serum, blood and blood products, environmental samples, or in whole cells. Thus, detection and quantification can be carried out in vivo by fluorescence microscopy or the like, or detection and quantification can be carried in vitro on any of the above extracts or on a sample obtained via in vitro mixing of sample materials and reagents.

The genetic constructs can be introduced into living cells using infective or non-infective transformation procedures that are well known in the art.

Regardless of the intended use, a suitable radiation source is used to illuminate the fluorophore after exposing the fluorophore and aptamer to one another. The radiation source can be used alone or with optical fibers and any optical waveguide to illuminate the sample. Suitable radiation sources include, without limitation, filtered, wide-spectrum light sources (e.g., tungsten, or xenon arc), laser light sources, such as gas lasers, solid state crystal lasers, semiconductor diode lasers (including multiple quantum well, distributed feedback, and vertical cavity surface emitting lasers), dye lasers, metallic vapor lasers, free electron lasers, and lasers using any other substance as a gain medium. Common gas lasers include Argon-ion, Krypton-ion, and mixed gas (e.g., Ar Kr) ion lasers, emitting at 455, 458, 466, 476, 488, 496, 502, 514, and 528 nm (Ar ion); and 406, 413, 415, 468, 476, 482, 520, 531, 568, 647, and 676 nm (Kr ion). Also included in gas lasers are Helium Neon lasers emitting at 543, 594, 612, and 633 m. Typical output lines from solid state crystal lasers include 532 nm (doubled Nd:YAG) and 408/816 nm (doubled/primary from Ti:Sapphire). Typical output lines from semiconductor diode lasers are 635, 650, 670, and 780 rnm. Infrared radiation sources can also be employed.

Excitation wavelengths and emission detection wavelengths will vary depending on both the fluorophore and the nucleic acid aptamer molecule that are being employed. Examples of different aptamer:fluorophore combinations are described in PCT Application Publ. No. WO/2010/096584 to Jaffrey and Paige, which is hereby incorporated by reference in its entirety. As demonstrated therein, several different aptamer molecules can differently affect the emission spectrum of a single fluorophore, affording very distinct emission patterns.

Detection of the emission spectra can be achieved using any suitable detection system. Exemplary detection systems include, without limitation, a cooled CCD camera, a cooled intensified CCD camera, a single-photon-counting detector (e.g., PMT or APD), dual-photon counting detector, spectrometer, fluorescence activated cell sorting (FACS) systems, fluorescence plate readers, fluorescence resonance energy transfer, and other methods that detect photons released upon fluorescence or other resonance energy transfer excitation of molecules.

In one embodiment, the detector is optically coupled to receive the output emissions of the fluorophore:aptamer complex through a lens system, such as in an optical microscope. In another embodiment, a fiber optic coupler is used, where the input to the optical fiber is placed in close proximity to the substrate surface of a biosensor, either above or below the substrate. In yet another embodiment, the optical fiber provides the substrate for the attachment of nucleic acid sensor molecules and the biosensor is an integral part of the optical fiber.

In one embodiment, the interior surface of a glass or plastic capillary tube provides the substrate for the attachment of the fluorophore or the sensor molecule (or molecular complex). The capillary can be either circular or rectangular in cross-section, and of any dimension. The capillary section containing the biosensors can be integrated into a microfluidic liquid-handling system which can inject different wash, buffer, and analyte-containing solutions through the sensor tube. Spatial encoding of the fluorophore or nucleic acid sensor molecules can be accomplished by patterning them longitudinally along the axis of the tube, as well as radially, around the circumference of the tube interior. Excitation can be accomplished by coupling a laser source (e.g., using a shaped output beam, such as from a VCSEL) into the glass or plastic layer forming the capillary tube. The coupled excitation light will undergo TIR at the interior surface/solution interface of the tube, thus selectively exciting fluorescently labeled biosensors attached to the tube walls, but not the bulk solution. In one embodiment, detection can be accomplished using a lens-coupled, or proximity-coupled large area segmented (pixelated) detector, such as a CCD. In a particular embodiment, a scanning (i.e., longitudinal/axial and azimuthal) microscope objective lens/emission filter combination is used to image the biosensor substrate onto a CCD detector. In a different embodiment, a high resolution CCD detector with an emission filter in front of it is placed in extremely close proximity to the capillary to allow direct imaging of the fluorophore:nucleic acid aptamer complexes. In a different embodiment, highly efficient detection is accomplished using a mirrored tubular cavity that is elliptical in cross-section. The sensor tube is placed along one focal axis of the cavity, while a side-window PMT is placed along the other focal axis with an emission filter in front of it. Any light emitted from the biosensor tube in any direction will be collected by the cavity and focused onto the window of the PMT.

In still another embodiment, the optical properties of a molecular complex are analyzed using a spectrometer (e.g., such as a luminescence spectrometer). The spectrometer can perform wavelength discrimination for excitation and detection using either monochromators (i.e., diffraction gratings), or wavelength bandpass filters. In this embodiment, the fluorophores of the molecular complexes are excited at absorption maxima appropriate to the fluorophore being used and fluorescence intensity is measured at emission wavelengths appropriate for the complexes being detected. Given that the intensity of the excitation light is much greater than that of the emitted fluorescence, even a small fraction of the excitation light being detected or amplified by the detection system will obscure a weak biosensor fluorescence emission signal. In one embodiment, the biosensor molecules are in solution and are pipetted (either manually or robotically) into a cuvette or a well in a microtiter plate within the spectrometer. In a further embodiment, the spectrometer is a multifunction plate reader capable of detecting optical changes in fluorescence or luminescence intensity (at one or more wavelengths), time-resolved fluorescence, fluorescence polarization (FP), absorbance (epi and transmitted), etc., such as the Fusion multifunction plate reader system (Packard Biosciences, Meriden, Conn.). Such a system can be used to detect optical changes in biosensors either in solution, bound to the surface of microwells in plates, or immobilized on the surface of solid substrate (e.g., a microarray on a glass substrate). This type of multiplate/multisubstrate detection system, coupled with robotic liquid handling and sample manipulation, is particularly amenable to high-throughput, low-volume assay formats.

In embodiments where the sensor molecules or fluorophores are attached to substrates, such as a glass slide or in microarray format, it is desirable to reject any stray or background light in order to permit the detection of low intensity fluorescence signals. In one embodiment, a small sample volume (about 10 nl) is probed to obtain spatial discrimination by using an appropriate optical configuration, such as evanescent excitation or confocal imaging. Furthermore, background light can be minimized by the use of narrow-bandpass wavelength filters between the sample and the detector and by using opaque shielding to remove any ambient light from the measurement system.

In one embodiment, spatial discrimination of a molecular complex of the invention (fluorophore:nucleic acid aptamer complexes or fluorophore:nucleic acid aptamer:target molecule complexes) attached to a substrate in a direction normal to the interface of the substrate is obtained by evanescent wave excitation. This is illustrated in PCT Application Publ. No. WO/2010/096584 to Jaffrey and Paige, which is hereby incorporated by reference in its entirety. Evanescent wave excitation utilizes electromagnetic energy that propagates into the lower-index of refraction medium when an electromagnetic wave is totally internally reflected at the interface between higher and lower-refractive index materials. In this embodiment a collimated laser beam is incident on the substrate/solution interface (at which the fluorophore:nucleic acid aptamer complexes or fluorophore:nucleic acid aptamer:target molecule complexes are immobilized) at an angle greater than the critical angle for total internal reflection (TIR). This can be accomplished by directing light into a suitably shaped prism or an optical fiber. In the case of a prism, the substrate is optically coupled (via index-matching fluid) to the upper surface of the prism, such that TIR occurs at the substrate/solution interface on which the molecular complexes are immobilized. Using this method, excitation can be localized to within a few hundred nanometers of the substrate/solution interface, thus eliminating autofluorescence background from the bulk analyte solution, optics, or substrate. Target recognition is detected by a change in the fluorescent emission of the molecular complex, whether a change in intensity or polarization. Spatial discrimination in the plane of the interface (i.e., laterally) is achieved by the optical system.

In the embodiment described above, a TIRF evanescent wave excitation optical configuration is implemented using a detection system that includes a universal fluorescence microscope. Any fluorescent microscope compatible with TIRF can be employed. The TIRF excitation light or laser can be set at either an angle above the sample shining down on the sample, or at an angle through the objective shining up at the sample. Effective results can been obtained with immobilization of either the aptamer or the fluorophore using NHS-activated glass slides. The fluorophore containing a free amine (at the $R_1$ position) can be used to react with the NHS-slide. RNA can be modified with a 5' amine for NHS reactions by carrying out T7 synthesis in the presence of an amine modified GTP analog (commercially available).

In the several embodiments described above, the output of the detection system is preferably coupled to a processor for processing optical signals detected by the detector. The processor can be in the form of personal computer, which contains an input/output (I/O) card coupled through a data bus into the processor. CPU/processor receives and processes the digital output signal, and can be coupled to a memory for storage of detected output signals. The memory can be a random access memory (RAM) and/or read only memory (ROM), along with other conventional integrated circuits used on a single board computer as are well known to those of ordinary skill in the art. Alternatively or in addition, the memory may include a floppy disk, a hard disk, CD ROM, or other computer readable medium which is read from and/or written to by a magnetic, optical, or other reading and/or writing system that is coupled to one or more processors. The memory can include instructions written in a software package (for image processing) for carrying out one or more aspects of the present invention as described herein.

In addition to their specificity in binding to fluorophores, a number of the aptamers have demonstrated that their affinity for the target fluorophore can be modulated by environmental conditions.

Figure 3A:
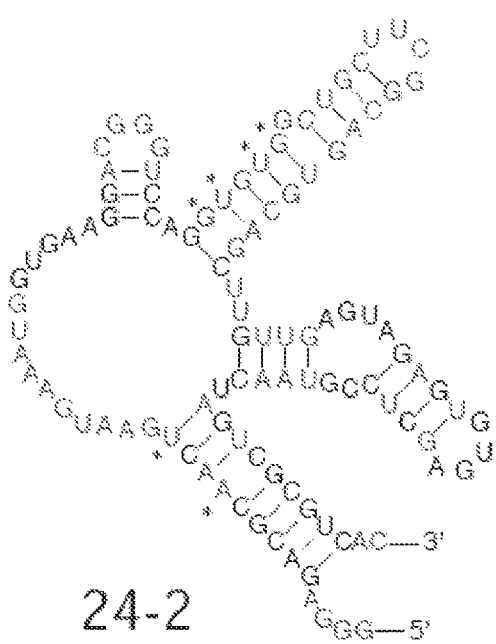
FIGS. 3A-C illustrate the secondary structures of three RNAs: the original 24-2 structure (3A, SEQ ID NO: 5), a minimized structure 24-2-min (3B, SEQ ID NO: 7), and a first generation derivative of 24-2, designated "Spinach" (3C, SEQ ID NO: 6). RNA structure is shown as predicted by Mfold web-based software (Zuker, "Mfold Web Server for Nucleic Acid Folding and Hybridization Prediction," *Nucl. Acids Res.* 31(13): 3406-3415 (2003), which is hereby incorporated by reference in its entirety).

According to one embodiment, the affinity of the aptamer for the fluorophore is partially or entirely ion dependent, i.e., any mono or divalent ion. For example, PCT Application Publ. No. WO/2010/096584 to Jaffrey and Paige, which is hereby incorporated by reference in its entirety, describes aptamers that are responsive to $Mg^{2+}$ or $K^+$. As shown in FIG. 3D, the aptamer of SEQ ID NO: 5 is responsive to $Mg^{2+}$ concentration. Others have identified aptamers that bind specifically to other ions, and can be incorporated into the sensors of the present invention. These include, without limitation, aptamers specific to zinc (Rajendran et al., "Selection of Fluorescent Aptamer Beacons that Light Up in the Presence of Zinc," Anal. Bioanal. Chem. 390(4):1067-1075 (2008), which is hereby incorporated by reference in its entirety), cobalt (Breaker et al., "Engineered Allosteric Ribozymes as Biosensor Components," Curr. Op. in Biotech 13(1):31-39 (2002), which is hereby incorporated by reference in its entirety), and lead (Brown et al., "A Lead-dependent DNAzyme with a Two-step Mechanism," Biochem. 42(23):7152-7161 (2003), which is hereby incorporated by reference in its entirety).

According to another embodiment, the affinity of the aptamer for the fluorophore is temperature dependent. Thus, a titration exists where at very high temperatures, no binding will occur, but at lower temperatures the highest degree of binding will occur. Based on the profile of a particular aptamer-fluorophore pair, the temperature within a system can be determined based on the measured fluorescence output. Aptamers that possess this property can be used as a sensor (discussed below) to determine the temperature of the environment.

According to another embodiment, the affinity of the aptamer for the fluorophore is partially pH dependent. The aptamers are fairly stable near neutral pH, but at higher or lower pH, the folding of the aptamer or the interaction between fluorophore/aptamer is disrupted such that changes in fluorescence can be measured as the pH varied away from neutral. Aptamers that possess this property can be used as a sensor (discussed below) to determine the pH of the environment.

The multivalent aptamers having first and second domains can be used for detection of a target molecule in a medium or sample. This is carried out by exposing the nucleic acid aptamer molecule of the invention to a medium suspected to contain the target molecule under conditions effective to allow the second domain to bind specifically to the target molecule, if present, and also exposing the nucleic acid molecule and medium to a fluorophore of the invention under conditions effective to allow the first domain to bind specifically to the fluorophore after binding of the target molecule by the second domain, thereby inducing the fluorophore to adopt a conformation that exhibits enhanced fluorescent emissions. Detection of molecular complex formation is then achieved by exciting the fluorophore (or FRET partner) with radiation of appropriate wavelength and detecting fluorescence by the fluorophore (or FRET partner), whereby the detection of fluorescence emissions by the fluorophore indicates binding of the nucleic acid molecule to the target molecule and, hence, its presence.

This embodiment can be carried out in whole cells either by introducing the nucleic acid aptamer molecule into the whole cell, or by transforming the whole cell with a transgene encoding the nucleic acid aptamer molecule. The fluorophore can be introduced into the environment of the whole cell, where it is readily taken up. This embodiment can also be carried out in vitro, i.e., in a cell free environment. An image of the detection process can also be acquired or generated using the detection systems described above.

This aspect of the invention is particularly adaptable to a microarray format, where the nucleic acid aptamer molecules are tethered at discrete locations on a substrate surface, i.e., solid support. The solid support used to form the microarray surface can include, without limitation, glass, metal, and ceramic supports. Tethering of the nucleic acid aptamer molecules can be carried out using a 5' biotin to streptavidin-coated glass (ArrayIt, Inc). Alternatively, the sensor molecules of the present invention can be provided with an extraneous sequence at its 5' end, where the extraneous sequence allows for tethering the sensor molecule to a hybridization partner tethered to the array surface using standard techniques. The hybridization partners can be printed onto the array surface, and the sensor molecules allowed to hybridize prior to or after exposing the sensor to the sample. In these array systems, fluorophore is in solution and is recruited to the glass surface only if the target molecule binds the second domain of the surface-bound aptamer, thereby creating a fluorophore:aptamer:target complex that can be detected, e.g., using TIRF. The sensors can be spotted in an array format, i.e., an array of microspots, or configured in other shapes or designs on surfaces, so that the sensors are positioned in a spatially defined manner. This will allow one or a series of sensors that are specific to distinct target molecules to be assayed following contact with a mixture that contains one or more of the target molecules at known or unknown concentrations. The fluorescence intensity can be used to determine the concentrations if suitable solutions containing known amounts of target analytes are used to calibrate the fluorescence signals.

Detection assays can also be carried out using the aptamer constructs that include a first domain that contains the fluorophore-binding aptamer and a second domain that is a hybridization probe has a nucleotide sequence complementary to a target nucleic acid molecule. For example, to detect viral RNA present in a sample, the hybridization probe will contain a nucleotide sequence complementary to the viral RNA. After attaching any nucleic acid in a sample to a substrate (e.g., glass surface), the sample is exposed to the fluorophore and the aptamer construct under conditions to allow hybridization to occur. Subsequent detection of the molecular complex (fluorophore:aptamer construct:complementary viral RNA target), as measured by the fluorescent emissions by the fluorophore on the substrate via TIRF, indicates presence of the viral RNA target. This same assay can be carried out using an aptamer construct that possess a second domain, which instead of being a hybridization probe, includes either an aptamer sequence or a non-aptamer sequence that binds to a specific protein (e.g., MS2 sequence binds the MS2 protein or a fusion protein containing the same), in which case binding of the protein to the substrate (e.g., in an ELISA format) will also allow for detection.

Alternatively, detection assays can be carried out using these same types of aptamer constructs using a fixed cell sample or histologic tissue sample. Where ever the target molecule is present in these samples, the aptamer construct can be bound to the sample and the fluorophore will identify its presence.

While microarrays for monitoring the transcriptome are commonplace and have revolutionized biology, similar approaches are not available to study the proteome. The system and method of the invention allow the production of a protein-sensing microarray. This novel platform for protein detection has the potential to dramatically speed up the analysis of proteins for innumerable applications. For example, these arrays can be used to assay a set of specific proteins, such as clinically relevant biomarkers, or large sections of the proteome, such as proteins of specific functional classes. Current microarray technologies that utilize a panel of antibodies requires labeling of the proteins in biological samples with fluorescent dyes, such as Cy5-NHS, in order for the protein to be detected after binding to the antibodies. This is problematic, because this labeling procedure may affect the epitope recognized by the antibody. In contrast, the sensor arrays of the present invention do not require target labeling because the sensor will only bind to the fluorophore (at its first domain) after that target molecule has been bound by its second domain. The microarray format of the present invention also overcomes a number of challenges that plagued antibody arrays due to: (1) the low cost of the aptamer sensor molecule; (2) the ease with which oligonucleotides can be coupled to microarray surfaces; (3) the ability to reliably synthesize homogeneous preparations of oligonucleotides, which is a challenge with antibodies; (4) the increased stability of oligonucleotides compared to antibodies; (5) the highly specific nature of aptamer-protein interactions, which typically involve large surfaces (Stoltenburg et al., "SELEX—A Revolutionary Method to Generate High-affinity Nucleic Acid Ligands," *Biomolecular Engineering* 24:381-403 (2007); Hermann and Patel, "Adaptive Recognition by Nucleic Acid Aptamers," *Science* 287:820-825 (2000), each of which is hereby incorporated by reference in its entirety) rather than short epitopes as with antibodies; and (6) the ease of sample preparation, as the fluorescent signaling obtained using these protein sensors does not require the sample processing step of fluorescent dye tagging. Instead, binding of the target protein to the sensor is sufficient to elicit a fluorescent signal (in the presence of the solution phase fluorophore), thereby dramatically simplifying the analysis of protein mixtures.

Thus, upon exposure to the target and fluorophore, the molecular complex will form and the fluorophore, upon illumination, will exhibit emission patterns from the discrete location on the array surface. Using appropriate mapping software, the presence of the fluorescent emission signal will positively identify the target molecule as being present in the sample being queried. As noted above, quantification can be carried out if reliable calibration is performed.

A further aspect of the invention involves using an aptamer construct having a first domain that includes a fluorophore-specific aptamer and a second domain that binds specifically to the target molecule for determining the location of a target molecule, particularly within a whole cell. This aspect of the invention involves forming a molecular complex (fluorophore:aptamer:target molecule), exciting the fluorophore with light of an appropriate wavelength, and then detecting fluorescence by the fluorophore, whereby fluorescence by the fluorophore identifies presence of the target molecule. In whole cells, this embodiment can be carried out by introducing the nucleic acid aptamer molecule into the whole cell, or by transforming the whole cell with a transgene encoding the nucleic acid aptamer molecule. Once inside the cell, the nucleic acid aptamer molecule will bind specifically to the target molecule via its second domain. The fluorophore can be introduced into the environment of the whole cell, where it is readily taken up. An image of the detection process can also be acquired or generated using the detection systems described above.

A DNA construct encoding an RNA aptamer molecule can be used to measure the transcription by a promoter of interest in a cell. This can be carried out by introducing a DNA construct or transgene encoding the RNA aptamer molecule into a cell, introducing the fluorophore into the cell, and then determining whether the aptamer:fluorophore complex forms, as measured by the amount of fluorescence detected within the cell.

This aspect of the invention can be used to screen agents for their ability to modulate transcription of the DNA construct and, thus, native genes that contain the same promoter as the DNA construct. When screening an agent, the agent is introduced to the cell, preferably prior to introducing the fluorophore. After a suitable time delay (to allow for transcription of the nucleic acid aptamer to occur, the fluorophore can be introduced to the cell. The detection of an increase or decrease in fluorescence by the fluorophore:aptamer complex within the cell, relative to an otherwise identical but untreated control cell, indicates that the agent altered the level of transcription by the promoter.

In an alternative embodiment, the same DNA construct can be used in an in vitro detection procedure, whereby the DNA construct and agent are both introduced into a cell and the fluorophore may or may not be introduced to the cell. In one approach, RNA transcription are recovered from the cell (using known cell lysis and RNA collection procedures) after exposure to the fluorophore. In another approach, RNA transcripts are first recovered from the cell, and then the fluorophore is introduced to the recovered RNA transcripts. The fluorophore can be bound to a solid surface of a suitable detection device, such as TIRF system or other detectors of the type described above. The detection of an increase or decrease in fluorescence by the fluorophore:aptamer complex within the recovered RNA transcripts, relative to the RNA transcripts recovered from an otherwise identical but untreated control cell, indicates that the agent altered the level of transcription by the promoter.

As a further alternative, the entire transcription and detection process can be carried out in vitro in the presence of the agent. This can be used to monitor the production of transcripts, and the effects of the agents on those transcripts.

In these embodiments, the agent can be, without limitation, a genetic or transgenic condition unique to a particular cell type, a drug (small molecule), amino acid, protein, peptide, polypeptide, vitamin, metal, carbohydrate, lipid, a polymer, or RNAi that influences transcription levels.

A further aspect of the invention relates to the monitoring an RNA molecule within a cell. This aspect of the invention involves the use of a DNA construct of the invention that expresses an RNA fusion that includes an RNA aptamer of the invention joined to an RNA molecule of interest. After introducing the DNA construct into a cell and allowing for transcription to occur, the fluorophore of the invention can be introduced to the cell. Alternatively, the RNA molecule can be expressed or synthesized in vitro and later introduced into the cell. Regardless of the approach, this will allow the RNA aptamer portion of the RNA fusion molecule to bind specifically to the fluorophore (forming an aptamer:fluorophore complex) and enhance its fluorescence emissions. Detection of the RNA fusion molecule (including its location, its quantitation, or its degradation) can be carried out by exposing the cell to radiation of a wavelength suitable to induce fluorescence emissions by the fluorophore within the molecular complex; and then measuring the fluorescent emissions of the fluorophore or a FRET partner. The (sub) cellular location of the fluorescence emissions indicates the location of the transcript. Also, any decrease in the fluorescence emissions over time indicate degradation of the transcript. The latter can be confirmed by recovering RNA transcripts and measuring for the RNA fusion using, e.g., RT-PCR. Finally, the level of fluorescence correlates to the quantity of the RNA fusion molecule that is present.

In this embodiment, the RNA product to be monitored can be any of a variety of RNA molecules having diverse functions. These include, without limitation, pre-mRNA, mRNA encoded a native or non-native expression product, pre-rRNA, rRNA, tRNA, hnRNA, snRNA, miRNA, siRNA, shRNA, long noncoding RNA, PIWI RNA, termini-associated RNA, noncoding RNAs, promoter-associated RNAs, viral RNAs, ribozyme, a stabilizing RNA molecule, an RNA sequence that binds a protein such as a MS2 protein-binding RNA, a targeting element that can localize the fusion nucleic acid molecule to a specific localization in the cell. The RNA product can be fused to either the 5' end or the 3' end of the aptamer molecule of the present invention.

The monitoring of the RNA can also be carried out by exposing the cell to an extracellular RNA molecule that includes an aptamer of the present invention, and cellular uptake of the RNA molecule can be observed via microscopy or measurement of the fluorescent emissions upon exposure to the fluorophore (either before or after cell uptake).

Thus, this aspect can used to monitor the effects of an experimental treatment on RNA localization, trafficking, expression levels, rate of degradation, etc., where the experimental treatment can be exposing the cell or organism to an agent such as a drug (small molecule), amino acid, protein, peptide, polypeptide, vitamin, metal, carbohydrate, lipid, a polymer, or RNAi that influences the target molecule or the expression level of another protein in a pathway influenced by the target RNA molecule, expression of a native or foreign gene in the cell or organism, or exposing the cell or organism to a change in environmental conditions (e.g., temperature, hypoxic or hyperoxic conditions, atmospheric pressure, pH, etc.). These treatments can be carried out directly on a transformed cell or cell population. Alternatively, these treatments can be performed on an organism that contains one or more cells transformed with a DNA construction encoding the fusion RNA molecule of interest.

To enhance the fluorescent signal, it is possible to tailor the number of fluorophores that can be bound to a single RNA transcript by using a concatamer of RNA aptamers. In addition, this aspect of the invention is particularly adaptable to assessing the trafficking or degradation of multiple RNA molecules simultaneously. This is possible due to the tailored emission spectra of different aptamer:fluorophore complexes. Thus, this aspect can include introducing a second DNA construct into a cell, wherein the second DNA construct encoding a distinct RNA fusion molecule that includes a distinct RNA aptamer of the invention (or a concatamer thereof) joined to a distinct RNA molecule of interest. After introducing the DNA construct into the cell or organism, and allowing for transcription to occur, a second fluorophore of the invention can be introduced to the cell or organism, i.e., one that is bound specifically by the aptamer present in the second RNA fusion molecule but not the first, and vice versa. This will allow the fluorophore-specific aptamer portion of the RNA to bind specifically to the fluorophore (forming an aptamer:fluorophore complex) and enhance its fluorescence emissions. Detection of fluorescence can be carried out as described above. Simultaneous detection of separate emission peaks will allow for detecting localization or co-localization of both complexes.

In a related aspect, the inventive materials can be used to assess RNA folding, unfolding, or folding-unfolding kinetics by monitoring changes in fluorescence after exposing the RNA fusion protein to a fluorophore of the present invention (to form a molecular complex). The unfolding or folding event can be produced by exposing the molecular complex to an agent such as a protein (e.g., enzyme such as helicase), chemical (e.g., a small organic molecule, vitamin, amino acid, antibiotic, protein, lipid, carbohydrate, polymer, nucleotide, RNA-binding protein, or RNA-binding molecule), ribozyme, or environmental changes (e.g., temperature, hypoxic or hyperoxic conditions, atmospheric pressure, pH, etc.). The RNA aptamer can be the target of the folding or unfolding, or the RNA aptamer can be fused to the target of the folding or unfolding and, as such, incidentally be subject to its folding or unfolding. For the fusion RNA molecule, this aspect of the invention can be practiced in vivo in which case the folding or unfolding event can be affected by the expression of a gene within a cell or organism where the gene encodes a protein, an RNA, a non-coding RNA, an RNAi molecule (e.g., siRNAi, shRNA). Detection of unfolding can be measured by a decrease in fluorescence, and detection of folding can be measured by an increase in fluorescence, following exposure of the in vitro system or cell to radiation of a wavelength suitable to induce fluorescence emissions by the fluorophore within the molecular complex; and then measuring the fluorescent emissions of the fluorophore or a FRET partner.

In a related aspect, the inventive materials can be used to assess RNA binding to another moiety by observing the proximity of the fluorescence signal generated by the RNA aptamer (or RNA fusion) to a moiety. The moiety can be an RNA sequence (e.g., mRNA encoding a protein or noncoding RNA of the types described above), DNA or modified nucleic acid molecule. The RNA aptamer can be the target of the binding event, or the RNA aptamer can be fused to the target of the RNA binding event and, as such, incidentally be subject to structural changes following the binding event. For the fusion RNA molecule, this aspect of the invention can be practiced in vivo in which case the RNA binding event can be carried by the expression of a transgene encoding the RNA fusion molecule within a cell or organism. Detection of RNA binding can be measured by a decrease in fluorescence, and a decrease in RNA binding can be measured by an increase in fluorescence, following exposure of the in vitro system or cell to radiation of a wavelength suitable to induce fluorescence emissions by the fluorophore within the molecular complex; and then measuring the fluorescent emissions of the fluorophore or a FRET partner.

A further aspect of the invention relates to monitoring a target molecule in a cell. This aspect of the invention can be carried out using a nucleic acid aptamer molecule that includes first and second domains, as described above, where the first domain binds specifically to the fluorophore only after the second domain binds specifically to the target molecule. Both the nucleic acid aptamer molecule and a fluorophore of the invention are introduced into a cell, allowing the fluorophore:aptamer:target complex to form in the presence of the target molecule and enhancing the fluorescence emissions by the fluorophore. Upon exposure of the cell to radiation of suitable wavelength to induce fluorescence emissions by the fluorophore that is bound in the complex or a FRET partner; and then measuring the fluorescent emissions of the fluorophore or FRET partner to monitor the target molecule. In this manner, the cellular location of the fluorescence emissions indicates the location of the target molecule, a decrease in the fluorescence emissions over time indicates degradation of the target molecule, and an increase in the fluorescence emissions over time indicates accumulation of the target molecule. Quantitation of the target molecule can be correlated to the level of fluorescence measured.

The target molecule in this aspect of the invention can be any protein, lipid, carbohydrate, hormone, cytokine, chemokine, cell signaling molecule, metabolite, organic molecule, or metal ion, as described above.

This aspect of the invention can be carried by introducing the nucleic acid aptamer molecule directly into the cell or, alternatively, by introducing into the cell a gene that encodes the nucleic acid aptamer molecule.

Another aspect of the present invention relates to a method of screening a drug that modifies gene expression. This aspect can be carried out using a transgene that encodes an RNA aptamer molecule of the present invention. The transgene can be provided with a promoter of interest whose activity is being monitored with respect to the drug being screened. After introducing the transgene into a cell, the cell is exposed to the drug and a fluorophore of the invention, effectively introducing these compounds into the cell. Thereafter, the level of RNA aptamer transcription is measured by exposing the cell to radiation of a wavelength suitable to induce fluorescence emissions by the fluorophore that is bound by the RNA aptamer molecule or a FRET partner, and the fluorescent emissions of the fluorophore or FRET partner are measured, as described above. A reduction or absence of fluorescent emissions, relative to an otherwise identical control cell that is not exposed to the drug, indicates that the drug inhibits expression of the transgene. An increase of fluorescent emissions, relative to an otherwise identical control cell that is not exposed to the drug, indicates that the drug promotes expression of the transgene.

Another aspect of the present invention relates to a method of screening a drug that modifies RNA splicing. This aspect can be carried out using a transgene that encodes an RNA aptamer molecule of the present invention, wherein the RNA transcript of the transgene includes an intron that, with proper splicing, will result in a mature RNA molecule that is a functional fluorophore-binding RNA aptamer of the invention. This method is carried out by introducing the transgene into a cell and exposing the cell to a drug, and allowing transcription to occur such that both the immature transcript and the drug will both be present in the cell when splicing is to occur. A fluorophore of the invention is also introduced into the cell, whereby the mature RNA aptamer, if properly spliced, will be able to bind specifically to the fluorophore to enhance its fluorescence emissions. Detection of whether proper splicing occurred (or not) can be carried out by exposing the cell to radiation of a wavelength suitable to induce fluorescence emissions by the fluorophore (that is bound by the mature RNA aptamer molecule), or its FRET partner, and then measuring the fluorescent emissions of the fluorophore or FRET partner. A reduction or absence of fluorescent emissions, relative to an otherwise identical control cell that is not exposed to the drug, indicates that the drug inhibits proper splicing of the transcript. An increase of fluorescent emissions, relative to the otherwise identical control cell that is not exposed to the drug, indicates that the drug promotes proper splicing of the transcript.

This aspect of the invention can also be carried out in vitro. Basically, a medium is provided that contains the immature RNA transcript (with intron), a spliceosome including an appropriate splicing enzyme, a drug to be screened, and the fluorophore. As noted above, the immature RNA transcript includes first and second exons having an intervening intron region, and the first and second exons, upon excision of the intron, form an RNA aptamer molecule of the present invention. Upon exposing the medium to radiation of a wavelength suitable to induce fluorescence emissions by the fluorophore that is bound by the RNA aptamer molecule (or a FRET partner), any fluorescent emissions of the fluorophore (or FRET partner) are measured. A reduction or absence of fluorescent emissions, relative to an otherwise identical medium that lacks the drug, indicates that the drug inhibits proper splicing of the transcript. An increase of fluorescent emissions, relative to an otherwise identical medium that lacks the drug, indicates that the drug promotes proper splicing of the transcript.

In these embodiments, as an alternative to exposing the cell or organism to a drug, the cell or organism can be exposed to a protein or polypeptide, modifying the expression level of a gene with the cell or organism where the gene encodes a protein, an RNA, a non-coding RNA, a shRNA, or other RNA, introducing a transgene into the cell or organism where the transgene expresses and RNAi molecule, or exposing the cell or organism to a change in environmental conditions of the types described above.

Yet another aspect of the invention relates to a method of screening a drug for activity on a target molecule (i.e., either enhancing or diminishing activity of the target molecule). This process is carried out by introducing or expressing within a cell a nucleic acid molecule aptamer molecule of the present invention that includes first and second domains, as described above, where the first domain binds specifically to the fluorophore only after the second domain binds specifically to the target molecule. A fluorophore of the type described above is also introduced into the cell, where the fluorophore is bound specifically to the first domain of the nucleic acid molecule when the target molecule is bound by the second domain, thereby enhancing fluorescent emissions by the first fluorophore. Upon exposure of the cell to radiation of suitable wavelength to induce fluorescence emissions by the fluorophore that is bound in the complex or a FRET partner, and then measuring the fluorescent emissions of the fluorophore or FRET partner, it is possible to determine whether the activity of the target molecule is modified by the drug. Where a difference exists in the fluorescent emissions by the fluorophore or FRET partner, relative to an otherwise identical cell that lacks the drug, then this will indicates that the drug modifies the activity of the target molecule.

A further aspect of the invention relates to the de novo creation of aptamer-based sensor molecules for a particular target, without any prior knowledge of the aptamer for the particular target. This process is achieved using a modified SELEX procedure, where the nucleic acid molecules of the pool each contain a partially destabilized aptamer molecule that contains a first domain that binds specifically to a fluorophore of the present invention, and a second domain that comprises a wholly or partly random sequence. By partially destabilizing the first domain, only after binding of the second domain to the target molecule is first domain capable of binding specifically to the fluorophore. This is effectively the same approach used in FIG. 7C for the Spinach-derived sensor.

SELEX is carried out by exposing the pool of nucleic acid molecules to a target molecule and the fluorophore (whereby fluorescence emissions by the fluorophore are enhanced by the binding of the first domain to the fluorophore). Illuminating the fluorophore with light of a wavelength suitable to induce fluorescence emissions by the fluorophore that is bound by the first domain molecule, and measuring the fluorescent emissions of the fluorophore provide an indication as to whether any members of the pool bound to the target molecule (via their second domain).

RNAs members of the pool can be "precleared" by passing the RNAs over fluorophore-bound to agarose. This will remove all library members that retain constitutive fluorophoe-binding activity (i.e., even in the absence of a functional second domain that binds to the target). In the next step, the pool is exposed to the fluorophore-bound agarose, except that this time the target will be added to the incubation buffer. All washes will also contain target. After washing, the elution will occur in the same buffer, except that no target will be present. Thus, any RNAs whose binding to the fluorophore is dependent on target will elute. These RNAs will be recovered and used for subsequent rounds of SELEX to enrich for target-regulated sensors. The fluorescence of each pool will be tested as above in the presence of the fluorophore with or without the target of interest, and individual clones that exhibit target-dependent fluorescence can be isolated.

A negative selection can also be used to ensure that the sensors do not respond to structurally related molecules. To do this, the structurally related molecules can also be introduced in the elution buffer, so that if they promote fluorophore binding they will be retained on the agarose (whereas sensor constructs that are unaltered by these structurally related molecules will elute).

Fundamentally, this same approach can be used to screen drugs for binding to a target nucleic acid molecule of interest. RNA sequences of interest that have no known drug to target the same can be screened against a library, for instance a chemical library, to find new molecules that would bind to this RNA sequence of interest. Because binding of drugs typically stabilizes RNA sequences, the sensor can be a turn-on sensor of the type described above. Rather than using a random nucleotide sequence for the second domain, the RNA sequence of interest is used as the second domain and it is fused to the fluorophore-binding aptamers of the invention (a first domain). Upon drug binding to the second domain, the nucleic acid molecule will adopt a stabilized conformation that allows the first domain to bind and induce fluorescence of a fluorophore. Thus, the chemical library can be screened based on whether or not the test molecule increases the overall fluorescence. This will allow for the rapid screening of chemical libraries for the discovery of new drugs that bind to known RNA sequences of interest.

In a further aspect of the invention, a transgene of the present invention can be inserted into a viral genome and then packaged to form an infective delivery vehicle, or the transgene can be inserted into a virus like particle to form a pseudovirion. Infection of a cell by the virus or pseudovirus can be detected by measuring expression of the transgene encoding the RNA aptamer or RNA fusion. Expression of the transgene can be detected by exposing the cell to the fluorophore and then exposing the cell to radiation of a wavelength suitable to induce fluorescence emissions by the fluorophore that is bound by the RNA aptamer molecule (or a FRET partner). Any fluorescent emissions of the fluorophore (or FRET partner) reflect transgene expression and, hence, viral or pseudoviral infection of the cell. In contrast, the absence of fluorescence indicates that the virus or pseudovirus did not infect the cell. This aspect of the invention can be used to screen putative therapeutic agents for their ability to inhibit viral infection. Additionally, viral particles themselves can be quantified by fluorescence if the viral particle contains single-stranded RNA containing the aptamer sequence and the fluorophore.

Kits

A further aspect of the present invention relates to various kits that can be used for practicing the present invention. The kit components can vary depending upon the intended use, and any reagents identified in this application can be included in the one or more kits. The kits can be packaged with components in separate containers or as mixtures, as noted below. Instructions for use may also be provided.

For example, according to one embodiment, the kit can include one or more fluorophores of the type described above and one or more nucleic acid aptamers or genetic constructs encoding those aptamers. The genetic construct can be designed for RNA trafficking studies, or for expression of multivalent sensor molecules.

In one embodiment, the aptamer component that is responsible for binding to the fluorophore can be selected such that each of a plurality of nucleic acid aptamers causes a different emission profile by a single fluorophore. In this way, a single fluorophore can be used for multiple, simultaneous detections. According to this embodiment, the plurality of nucleic acid aptamers can be supplied separately, e.g., in different containers, or they can be supplied as a mixture or as a range of mixtures, such that each mixture is characterized by a different blended fluorescent emission pattern with the same fluorophore.

According to another embodiment, the kit can include one or more fluorophores that are immobilized on a substrate to allow for SELEX. The substrate can be an FTIR suitable flow cell. The kit can also include one or more "turn-on" sensor molecules, which are matched for each of the one or more fluorophores, i.e., the fluorophore-specific domain of the sensor is specific for only one of the surface-bound fluorophores or elicits distinct emissions by two or more of the surface-bound fluorophores. This will allow for detection of the target molecule in a sample.

According to another embodiment, the kit can include one or more nucleic acid aptamers that are immobilized on a support, which can be a surface of a substrate. Examples of suitable supports include, without limitation, another nucleotide sequence including RNA, DNA, PNA or modifications or mixtures of these oligonucleotides; a macromolecular structure composed of nucleic acid, such as DNA origami; a surface composed of glass, such as a glass slide; a surface formed of a plastic material such as plastic slides; a protein or polypeptide, such as an antibody; an oligosaccharide; a bead or resin. The substrate can be provided with a plurality of the nucleic acid aptamers that are positioned at discrete locations so as to form an array. The spots on the array where the nucleic acid aptamers are retained can have any desired shape or configuration.

According to another embodiment, the kit can include a plurality of distinct fluorophores of the invention, and a plurality of distinct nucleic acid molecules of the invention which bind specifically to at least one of the plurality of fluorophores. Preferably, only a single monovalent or multivalent nucleic acid aptamer molecule is provided for each fluorophore. To enable their use together, each fluorophore:aptamer pair should be characterized by a distinct emission spectrum such that each can be detected independently. As demonstrated by the accompanying examples, a plurality of distinct aptamer/fluorophore complexes can achieve distinguishable emission spectra. The multiple colors will allow imaging of multiple RNAs simultaneously and allow the development of protein-RNA and RNA-RNA FRET systems.

For example, using multiple sensor molecules with distinct fluorophores that are compatible with FRET, detection of interactions of RNA or DNA with fluorescent proteins, RNAs, or other molecules can be achieved. FRET occurs if an appropriate acceptor fluorophore is sufficiently close to the acceptor fluorophore. Therefore, the interaction of a fluorescent protein, RNA, DNA, or other molecule with an RNA-fluorophore complex can be detected by measuring the FRET emission upon photoexcitation of the acceptor. Measurements like this can be used to measure the rate of binding of a fluorescent molecule to an RNA that is tagged with an RNA-fluorophore complex in both in vitro and in vivo settings. In a similar application, the RNA-fluorophore complex can serve as a donor and a fluorescent protein, RNA, DNA, other molecule can serve as the acceptor. In these cases, the RNA-fluorophore complex can be excited, and FRET emission can be detected to confirm an interaction. As used herein, a FRET partner refers to either a FRET acceptor or a FRET donor, which is used in combination with the fluorophore/aptamer complex of the present invention.

According to another embodiment, the kit can include an empty genetic construct of the invention, as described above, along with one or more of the following: one or more restriction enzymes, one or more fluorophore compounds of the invention (which are operable with the aptamer sequence encoded by the construct), and instructions for inserting a DNA molecule encoding an RNA molecule of interest into the restriction sites for formation of a genetic construct that encodes a transcript comprising the RNA molecule of interest joined to the RNA aptamer molecule.

EXAMPLES

The following examples are intended to illustrate practice of the invention, and are not intended to limit the scope of the claimed invention.

Materials and Methods for Example 1-4

Reagents and Equipment:

Unless otherwise stated, all chemistry reagents were purchased from Acros Organics and all cell culture reagents were purchased from Invitrogen. Commercially available starting reagents were used without further purification. DFHBI was synthesized as described in PCT Application Publ. No. WO/2010/096584 to Jaffrey and Paige; Paige and Jaffrey, "RNA Mimics of Green Fluorescent Protein," *Science* 333(6042):642-646 (2011), each of which is hereby incorporated by reference in its entirety. Flash chromatography was conducted with 200-400 mesh silica gel 60 (EMD) and with ACS or HPLC grade solvents (Fisher). NMR spectra were recorded on a Bruker DMX-500 spectrometer at 500 MHz. Chemical shifts were reported as parts per million (ppm) downfield from an internal tetramethylsilane standard ($\delta$=0.0 for $^1$H NMR) or from solvent references. LC/MS (MS: ESI$^+$) was performed on a Waters Acquity ultra-performance liquid chromatography (UPLC) system connected to a Waters Micromass SQ electrospray ionization (ESI) spectrometer. UPLC was performed at a flow rate of 0.5 ml/min (monitored with a PDA from 210-500 nm) using a Waters C18 column. Absorbance spectra were recorded with a Thermo Scientific NanoDrop 2000 spectrophotometer with cuvette capability. Fluorescence excitation and emission spectra were measured with a Perkin Elmer LS-55 fluorescence spectrometer.

Preparation of Affinity Matrix:

Amine-functionalized fluorophores, such as DFHBI, were first dissolved in DMSO at a concentration of 40 mM and then diluted into 100 mM HEPES buffer pH 7.5 with a final concentration of 5% DMSO and 2 mM fluorophore. This fluorophore solution was then added to NHS-activated Sepharose (GE Life Sciences), which had been pre-equilibrated with 2 volumes of ice-cold buffer. The resin was then incubated with fluorophore solution overnight at 4° C. in the dark. The resin was washed with reaction buffer and incubated with 100 mM Tris pH 8.0 for 2 h at 25° C. to react with any remaining NHS-activated sites. After thorough washing, the resin was stored in 1:1 ethanol:100 mM sodium acetate pH 5.4 at 4° C. The efficiency of Sepharose coupling was monitored by measuring the absorbance at 400 nm of free fluorophore in the flow-through. Using this approach, it was estimated that the resin contains approximately 5 μmols of fluorophore per ml.

Affinity Measurements:

Dissociation constants ($K_D$) for the RNA-fluorophore complexes were determined by measuring the increase in fluorescence as a function of increasing fluorophore concentration in the presence of a fixed concentration of RNA aptamer. For each concentration of fluorophore measured, a background signal for fluorophore alone was also measured and subtracted from the signal measured for RNA and fluorophore together. Curves were determined using a non-linear regression analysis in Prism software and matched by least squares fitting to a standard dose-response model for 1:1 complexation.

Quantum Yield Measurements:

All quantum yields were determined by comparing the integral of the corrected emission spectra for each fluorophore or RNA-fluorophore complex with the corresponding integral obtained from a solution of the same concentration of lucifer yellow and acridine yellow (for DFHBI). Integrals at various concentrations were then plotted against the absorbance obtained at the wavelength corresponding to the excitation wavelength and the slope of the curve was compared to the slope of the curves found for reference fluorophores. All measurements for RNA-fluorophore complexes were taken in the presence of excess RNA to avoid interference from unbound fluorophore. The absolute quantum yields for reference fluorophores were taken to be 0.21 for lucifer yellow (Stewart, "Synthesis of 3,6-Disulfonated 4-aminonaphthalimides," *J. Am. Chem. Soc.* (1981), which is hereby incorporated by reference in its entirety), and 0.47 for acridine yellow (Olmsted, "Calorimetric Determinations of Absolute Fluorescence Quantum Yields," *J. Phys. Chem.* (1979), which is hereby incorporated by reference in its entirety).

Photobleaching Curves:

Photobleaching experiments were performed on fluorescein, EGFP and 24-2-DFHBI complexes immobilized on chemically functionalized glass slides (MicroSurfaces). To immobilized fluorescein, fluorescein cadaverine (Sigma-Aldrich) was reacted in 40 mM HEPES pH 8.0 with NHS-activated glass slides for 2 h at 25° C. Slides were then incubated in 100 mM Tris pH 8.0 to quench any unreacted NHS-activated sites. For EGFP, His$_6$-EGFP was expressed from pTrcHis in *E. coli* strain BL21 (Novagen), purified on TALON metal affinity resin (Clontech) and immobilized by incubating with nitrilotriacetic acid chelated copper functionalized glass slides for 2 h at 25° C. To immobilize 24-2-DFHBI, a 3' amine modified 21-nt DNA oligo (sequence: 5'-GGT TGT AAG TTT TAG GTT GCC-NH$_2$-3', SEQ ID NO: 45; Integrated DNA Technologies) was reacted with NHS-activated glass slides. Unreacted NHS-activated sites were blocked as above. 24-2 RNA was then in vitro synthesized with a 5' overhang complimentary to the immobilized DNA oligo. Purified 24-2 RNA was denatured at 65° C. and incubated with the slide at 25° C. for 20 min to allow hybridization to the immobilized oligonucleotide. All slides were then washed several times and incubated in either PBS pH 7.4 (EGFP and fluorescein) or selection buffer (pH 7.4) with 20 µM DFHBI (24-2) for 30 min and then illuminated continuously with a Nikon Intensilight C-HGFIE 130 W mercury lamp for 45 min. Images were captured every 10 s with a CoolSnap HQ2 CCD camera through a 10× air objective mounted on a Nikon TE2000 microscope and analyzed with the NIS-Elements software. Mock-treated slides incubated with either PBS (EGFP and fluorescein) or selection buffer with 10 µM DFHBI (24-2) were used to calculate background levels. Total fluorescence was then plotted against exposure time and normalized to the maximum intensity of each fluorophore.

Visualization of Nonspecific Fluorescence Activation by Cellular Components:

HEK293 cells were grown on PLL-coated glass-bottom dishes (MatTek) in DMEM plus 10% FBS to ~80% confluency. Media was removed, cells were washed twice with microscopy media (20 mM HEPES pH 7.4, 119 mM NaCl, 5 mM KCl, 2 mM CaCl$_2$, 2 mM MgCl$_2$, and 30 mM glucose) and then incubated for 30 min with microscopy media plus vehicle (0.2% DMSO) or 10 µM N,N-Dimethyl-4'-nitro-4-stilbenamine, thiazole orange, malachite green, or DFHBI. Live fluorescence images were then taken with a CoolSnap HQ2 CCD camera through a 40× oil objective mounted on a Nikon TE2000 microscope and analyzed with the NIS-Elements software.

Cytotoxicity Assays:

HEK293 cells were grown on PLL-coated glass-bottom dishes as indicated above. At ~80% confluency, the media was removed and cells were incubated for 30 min with fresh media alone, media plus vehicle (0.2% DMSO) or media plus 10 µM DMHBI, DFHBI or MG. Cells were then illuminated for 10 min at 37° C. with a Nikon Intensilight C-HGFIE 130 W mercury lamp with FITC (DMHBI and DFHBI) or Cy5 (malachite green) filter sets (Chroma Technology) on an inverted epifluorescence microscope. Control cells were illuminated for 10 min under identical conditions but in the absence of any fluorophore. Cells were then washed several times with media to remove fluorophores and assayed for mitochondrial activity with MTT (3-[4,5-dimethylthiazol-2-yl]-2,5-diphenyltetrazolium bromide) based cell proliferation kit (Roche) and prepared according to manufacturers instructions. MTT absorbance readings were performed at 550 nm with 650 nm absorbance used for background subtraction. Values are reported as percent change in viability compared to control samples (illumination without fluorophore or without vehicle) and each condition was repeated in triplicate and averaged.

Example 1

Library Design and SELEX for DFHBI-Binding Aptamers

For selections against DFHBI, a partially-structured library was used in which two 26-base random stretches were separated by a 12-base fixed sequence (5'-CTG CCG AAG CAG-3', SEQ ID NO: 46), which coded for a 4-base pair stem and a stable UUCG tetraloop in the transcribed RNA. This library has previously been described and used to obtain aptamers to small molecules with unusually high affinities (Davis and Szostak, Isolation of High-affinity GTP Aptamers from Partially Structured RNA Libraries," *Proc Natl Acad Sci USA*. 99:11616 (2002), which is hereby incorporated by reference in its entirety). The primer complimentary to the 5' end (5'-GTA TAA TAC GAC TCA CTA TAG GGA GAC GCA ACT GAA TGA A-3', SEQ ID NO: 47) includes the T7 promoter, while the 3' primer was considerably shorter (5'-GTG ACG CGA CTA GTT ACG GA-3', SEQ ID NO: 48) and complimentary to the 3' end of the RNA library. The single stranded DNA libraries were synthesized on a one-micromole scale (Keck Oligonucleotide Synthesis Facility, Yale University). The libraries were purified on a 10% TBE-Urea acrylamide gel. Full-length DNA was visualized and cut out of the gel with UV shadowing and then recovered from the gel using the crush and soak method. Purified single stranded DNA library was then used in a PCR reaction to gently amplify the library and to create double stranded DNA templates for RNA in vitro synthesis. To reduce PCR-induced bias, $10^{14}$ DNA molecules were amplified in a 10 ml PCR reaction for only 14 cycles. The PCR products were purified by DNA clean up columns (Zymo Research) to remove proteins, primers, and salts, and used for in vitro transcription.

$5.0 \times 10^{13}$ different sequences of double stranded DNA were transcribed in a 250 µl T7 RNA polymerase transcription reaction using the T7-flash kit (Epicentre Biotechnologies). After treatment with DNase (New England Biolabs) for 1 h, RNAs were precipitated using 1 volume 5 M ammonium acetate, incubated on ice for 15 min, then centrifuged at 4° C. for 15 min at 13,000×g. The supernatant was removed and pellets were washed twice with cold 75% ethanol. After air drying, the RNA pellets were resuspended in selection buffer containing 40 mM HEPES pH 7.4 (or 40 mM Bicine pH 8.0), 125 mM KCl, 5 mM MgCl$_2$, and 5% DMSO. The RNA was then heat denatured at 75° C. for 5 min and quickly placed on ice to cool. To remove RNAs that bound to the affinity matrix or recognized the aminohexyl linker of the fluorophore resin, the RNA library was first incubated for 30 min with 500 µl of "mock" resin. The mock resin consisted of NHS-activated Sepharose that had been treated with free hexylamine under the exact same reaction conditions and stoichiometry as the fluorophore resin coupling. RNAs were then incubated for 30 min with 500 µl of fluorophore resin and washed with 1 ml selection buffer: 6 times (rounds 1-5), 20 times (round 6), or 10 times (rounds 7-10). RNAs were then eluted 4 times with 500 µl selection buffer containing with 1-2 mM free fluorophore for 30 min. RNAs were eluted over the course of two hours to ensure the enrichment of high affinity aptamers (Davis and Szostak, "Isolation of High-affinity GTP Aptamers from Partially Structured RNA Libraries," *Proc Natl Acad Sci USA*. 99:11616 (2002), which is hereby incorporated by reference in its entirety). Eluting RNAs with free fluorophore rather than with RNA denaturing reagents, such as EDTA or heat, further ensured that selected RNAs do not require the affinity matrix or the aminohexyl linker for binding. The eluted RNAs were then ethanol precipitated with 1 µg of glycogen, reverse-transcribed, PCR amplified and in vitro transcribed to yield the pool for the next round. After several rounds, shorter incubation times and less resin volume was used to further force the selection of aptamers with the highest affinity for fluorophore. In later rounds the stringency of the washing steps was increased by including brief washes with fluorophore itself in an attempt to eliminate low and moderate affinity aptamer (Davis and Szostak, "Isolation of High-affinity GTP Aptamers from Partially Structured RNA Libraries," *Proc Natl Acad Sci USA*. 99:11616 (2002), which is hereby incorporated by reference in its entirety). From round five through ten, both the number and incubation time of the fluorophore wash steps was slowly increased.

After eight rounds of SELEX at pH 8.0 using DFHBI-agarose, clones were identified that switched on DFHBI fluorescence. The most promising clone, 24-2, exhibited an emission peak at 501 nm, with an excitation peak at 469 nm (FIG. 2A). The RNA sequence for clone 24-2 (SEQ ID NO: 5) appears in FIG. 1.

Figure 2B:
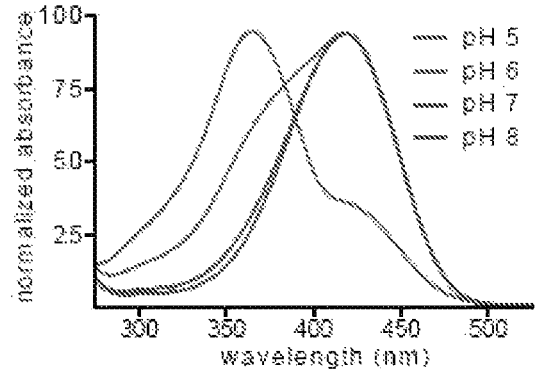

Remarkably, 24-2-DFHBI complexes were 7-fold brighter than 13-2-DMHBI complexes. The quantum yield was 0.72, which is 20% higher than EGFP. The molar brightness of 24-2-DFHBI is 53% of EGFP, but brighter than other fluorescent proteins, such as mHoneydew or mCherry (Shaner et al., "Improved Monomeric Red, Orange and Yellow Fluorescent Proteins Derived from *Discosoma* sp. Red Fluorescent Protein," *Nat. Biotechnol.* 22:1567 (2004), which is hereby incorporated by reference in its entirety). The brightness and the presence of a single major excitation peak at a position consistent with the deprotonated form of DFHBI (FIG. 2B) indicates that the 24-2-DFHBI complex, like EGFP, primarily involves fluorescent activation of the phenolate form of the fluorophore.

Example 2

Characterization of DFHBI-Binding Aptamer 24-2

Figure 2C:
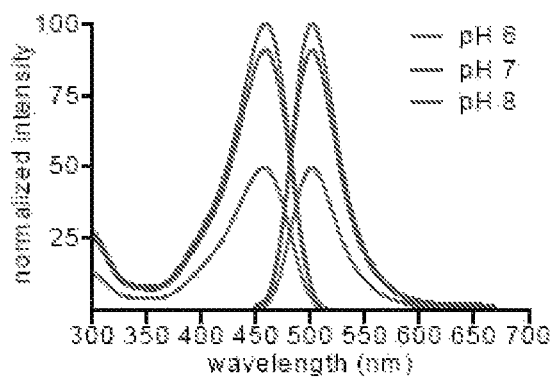
Figure 2D:
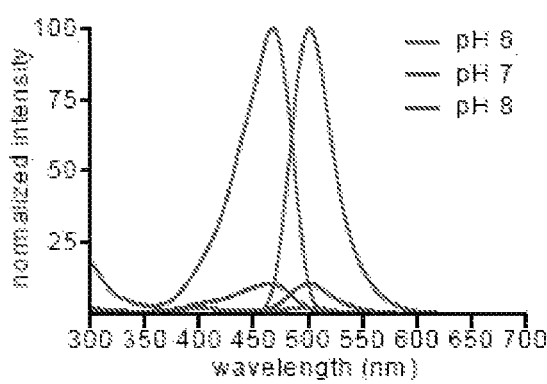

It was next determined whether 24-2 selectively binds the phenolate form of DFHBI or whether the binding was independent of the protonation state. DFHBI is primarily phenolic at pH 8.0 and 7.0, while at pH 6.0, both the phenolic and phenolate forms are detected (FIG. 2B). 24-2-DFHBI complexes are fluorescent at each of these pHs, with decreasing fluorescence observed at pH 6.0. Notably, as the pH is lowered, no new excitation peak corresponding to the protonated DFHBI is observed (FIG. 2C), suggesting that 24-2 does not bind protonated DFHBI. To further test the phenolate preference of 24-2, fluorescence emissions of 24-2 complexed with HBI was measured. HBI is similar in structure to DFHBI, but lacks the pair of fluorines. Nevertheless, HBI binds 24-2, albeit with reduced overall brightness (FIG. 2D). Because the $pK_a$ of HBI is 8.1 (Bell et al., "Probing the Ground State Structure of the Green Fluorescent Protein Chromophore using Raman Spectroscopy," *Biochemistry (Mosc.)*. 39:4423 (2000), which is hereby incorporated by reference in its entirety), both the phenolate and phenolic form of HBI are present at pH 8.1, and negligible amounts of the phenolate form are expected at pH 7.0 and 6.0. Consistent with the model in which only the phenolate form of the fluorophore binds 24-2, robust fluorescence of the 24-2-HBI complex was observed at pH 8.0, but only minimal fluorescence at pH 7.0 or 6.0. Taken together, these data show that 24-2 selectively recognizes the phenolate form of the fluorophore.

Figure 2E:
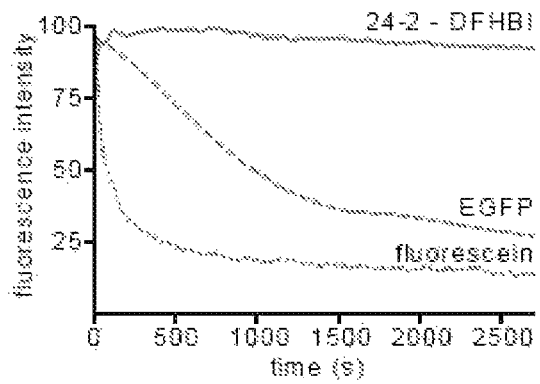

The photobleaching properties of 24-2-DFHBI complexes were examined next. Illumination of GFP leads to photobleaching, which ultimately limits the duration in which GFP can be imaged (Tsien, "The Green Fluorescent Protein," *Annu. Rev. Biochem.* 67:509 (1998), which is hereby incorporated by reference in its entirety). To assess the photostability of 24-2-DFHBI, 24-2, EGFP, and fluorescein were immobilized to glass slides. Total fluorescence was measured during continuous illumination. As expected, EGFP was considerably more stable than fluorescein (FIG. 2E). However, 24-2-DFHBI exhibited no measurable loss of fluorescence under identical conditions. In the case of 24-2-DFHBI complexes, the buffer contained 10 μM DFHBI. The lack of photobleaching suggests that exchange of bound DFHBI with DFHBI in solution ensures that complexes of 24-2 bound to photobleached DFHBI do not accumulate. Together, these studies indicate that 24-2 bound to the phenolate form of DFHBI exhibits enhanced brightness, and that 24-2-DFHBI fluorescence is unusually resistant to photobleaching.

Example 3

Aptamer 24-2 Structure Predictions and Mutagenesis

Secondary structure prediction was performed using Mfold online software (Zuker, "Mfold Web Server for Nucleic Acid Folding and Hybridization Prediction," *Nucl. Acids Res.* 31(13): 3406-3415 (2003), which is hereby incorporated by reference in its entirety). Mutated and truncated RNAs were created by ordering single stranded DNA templates (Integrated DNA Technologies) with the desired mutations or truncations and PCR amplifying these sequences to create double stranded DNA templates using primers which included a 5' T7 promoter sequence. PCR products were then purified with PCR purification columns (Qiagen) and used as templates for in vitro T7 transcription reactions (Epicentre).

Figure 3B:
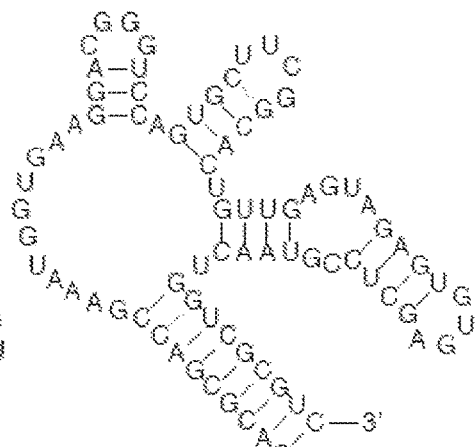

Truncation analysis indicated that an 80-nt domain within 24-2 is the minimal domain required for fluorescence (FIG. 3B). Although this minimal domain was slightly less fluorescent than the parent aptamer, mutagenesis experiments identified mutations that maintained the fluorescence of the final aptamer at the same level as the parent aptamer. Mutagenesis experiments also supported the predicted secondary structure (FIG. 3A). Maximal fluorescence was achieved at 3 mM magnesium, and greater than 50% maximal fluorescence was achieved even at 0.1 mM magnesium, which is the lower end of basal magnesium concentrations in most cell types (London, "Methods for Measurement of Intracellular Magnesium: NMR and Fluorescence," *Annu. Rev. Physiol.* 53:241 (1991), which is hereby incorporated by reference in its entirety) (FIG. 3D).

Example 4

Live Cell Imaging in Mammalian Cells

Figure 3C:
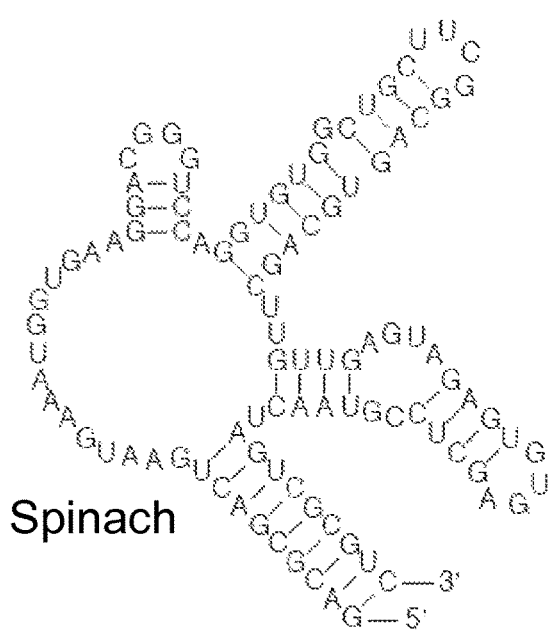
Figure 3D:
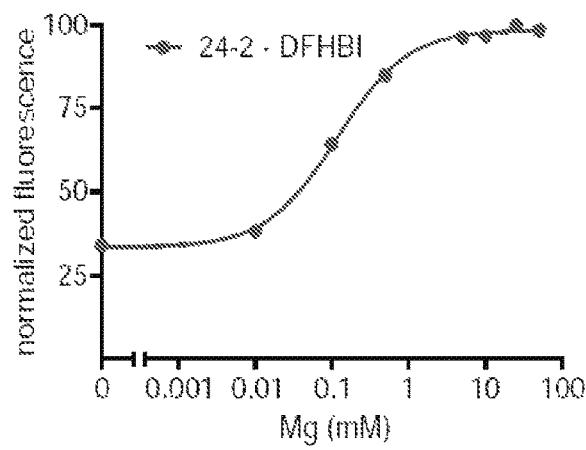
FIG. 3D illustrates the magnesium dependence of 24-2-DFHBI fluorescence. The fluorescence of the 24-2-DFHBI complex was measured at pH 7.4 in the presence of increasing magnesium concentrations. Interestingly, 24-2-DFHBI retained significant fluorescence even in the absence of magnesium.

Because of the spectral properties and green fluorescence of 24-2-DFHBI complexes, a 24-2 derivative was designated "Spinach" (FIG. 3C). The brightness of Spinach-DFHBI complexes suggested that it may be valuable for imaging RNA in cells.

HEK293 cells cultured on 24-well glass-bottom dishes were transfected with 0.2 μg of pAV-5S construct expressing full length human 5S RNA from its endogenous promoter fused through its 3' end with either a control sequence (lambda fragment ~400 nt) or the Spinach aptamer sequence using FuGene 6 (Roche) per manufacturer's instructions. Imaging experiments were performed 48 hours after transfection. Thirty minutes prior to experiment, HEK293 cell media was replaced with imaging media (DMEM with no phenol red or vitamins and supplemented with 25 mM HEPES, 5 mM MgSO$_4$, and 10 µg/ml Hoechst 33342) and 20 µM DFHBI or vehicle were added to the cells to promote RNA-fluorophore complex formation. To induce stress granule formation, cells were treated with 100 mM MgSO$_4$ or 600 mM sucrose for 30 minutes prior to imaging. Live fluorescence images of HEK293 cells were taken with a CoolSnap HQ2 CCD camera through a 100× oil objective mounted on a Nikon TE2000 microscope and analyzed with the NIS-Elements software. A filter cube typically used for fluorescein/EGFP with sputter coated excitation filter 470/40, dichroic mirror 495 (long pass), and emission filter 525/50 (Chroma Technology) was used to detect Spinach.

Figure 4A:
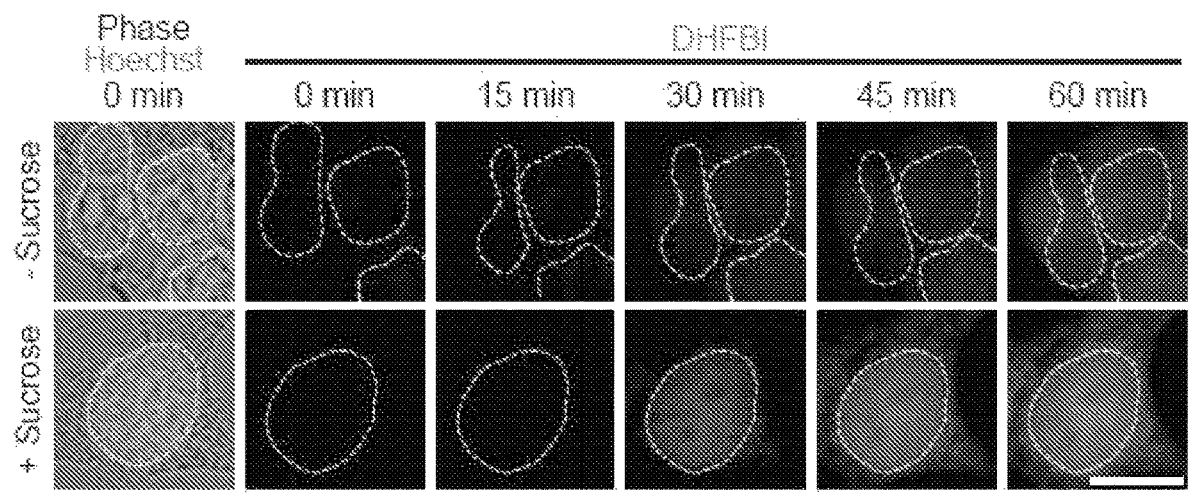
FIGS. 4A-B illustrate the live mammalian cell imaging of Spinach-tagged 5S RNA in HEK293T. The Spinach element, stabilized by a modified tRNA scaffold, was fused to the 3' end of the 5S RNA sequence and the entire fusion construct was expressed using the endogenous mammalian 5S promoter. A U5 transcription termination signal was present at the 3' end to ensure predictable 3' structure and increase the stability of the RNA. Fluorescence and phase images of HEK293T cells expressing a Lambda-tagged 5S RNA in the presence of 20 µM DFHBI with or without 30 minutes stimulation with 600 mM sucrose (↑Suc), Spinach-tagged 5S RNA in the presence of DMSO, or Spinach-tagged 5S RNA in the presence of 20 µM DFHBI with no stimulation or after 30 minutes stimulation with 100 mM MgSO4 (↑Mg) or 600 mM sucrose (↑Suc). 20 µm scale bar.
Figure 5:
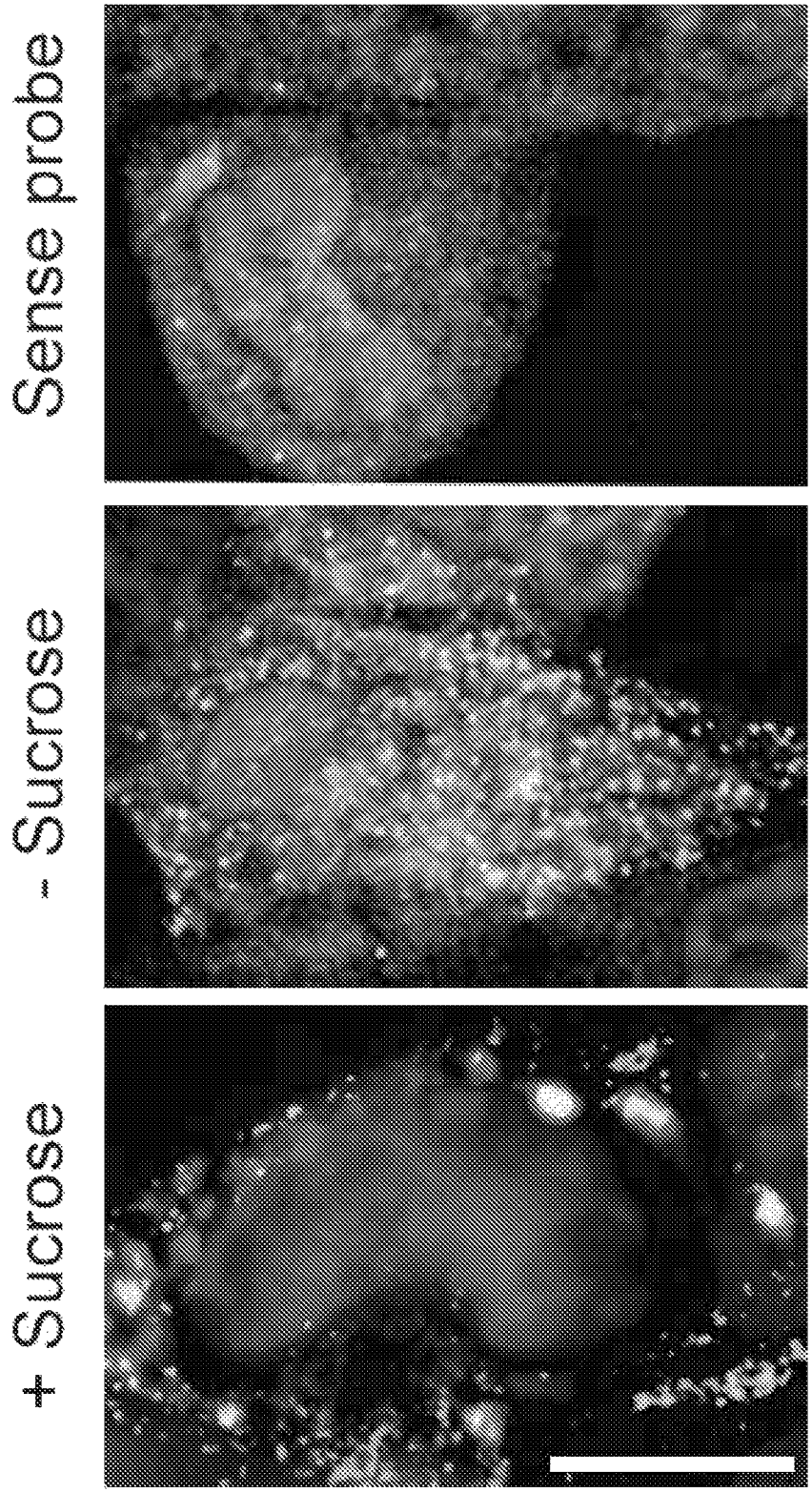
FIG. 5 is a series of images showing the co-staining of HEK293T cells for 5S-Spinach RNA and TIAR, a widely used protein marker for stress granules, which illustrates that sucrose treatment causes 5S-Spinach to accumulate into stress granules. In these experiments, in situ hybridization was performed using digoxigenin (Dig)-labeled riboprobes directed against the Spinach sequence, followed by Hoechst staining (blue) and immunostaining of Dig (green) and TIAR (red). Sense Spinach riboprobes were used as a negative control, and show negligible nonspecific probe labeling (upper panel). A z-stack slice from 5S-Spinach expressing cells not treated with 600 mM sucrose shows 5S-Spinach RNA diffusely localized throughout the nucleus and cytoplasm (central panel). After 30 min of sucrose stimulation, both 5S-Spinach and TIAR were localized to granular structures and exhibited prominent co-localization indicated in yellow (bottom panel). These results indicate that 5S-Spinach localizes to TIAR-positive stress granules under conditions of high sucrose. Scale bar, 10 µm.

To determine if Spinach could be used to tag RNAs in living mammalian cells, Spinach was fused to the 3' end of 5S, a small noncoding RNA transcribed by RNA polymerase III (Pol III) that associates with the large ribosomal subunit, and transfected this construct into HEK293T cells. The 3' end of 5S is solvent exposed, and addition of short sequences to the 3' end does not affect 5S localization (Paul et al., "Localized Expression of Small RNA Inhibitors in Human Cells," *Mol. Ther.* 7:237 (2003), which is hereby incorporated by reference in its entirety). 5S-Spinach fluorescence was detected throughout cells (FIG. 4A), with a distribution similar to that of endogenous 5S in the same cell type (Paul et al., "Localized Expression of Small RNA Inhibitors in Human Cells," *Mol. Ther.* 7:237 (2003), which is hereby incorporated by reference in its entirety). Following application of 600 mM sucrose, a form of cellular stress which induces the formation of cytoplasmic RNA granules (Thomas et al., "RNA Granules: The Good, the Bad and the Ugly," *Cell. Signal.* 23(2):324-34 (2010), which is hereby incorporated by reference in its entirety), 5S-Spinach relocalized to large (~2-3 µm) cytosolic foci, many of which colocalize with TIAR, a marker of stress granules (Kedersha et al., "RNA-binding Proteins TIA-1 and TIAR Link the Phosphorylation of eIF-2 alpha to the Assembly of Mammalian Stress Granules," *J. Cell Biol.* 147:1431 (1999), which is hereby incorporated by reference in its entirety) (FIG. 5).

Figure 4B:
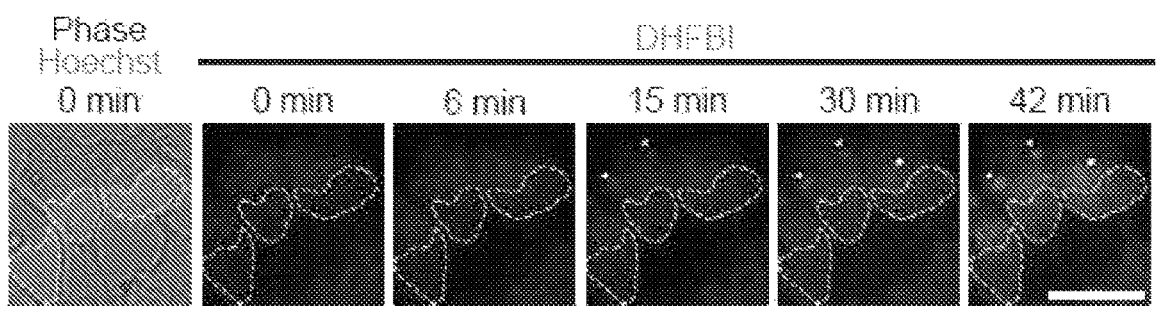

To monitor live cell 5S dynamics, cells were treated with the Pol III inhibitor ML-60218 (Wu et al., "Novel Small-molecule Inhibitors of RNA Polymerase III," *Eukaryot. Cell.* 2:256 (2003), which is hereby incorporated by reference in its entirety), which reduces 5S-Spinach fluorescence to baseline levels. The nuclear export of 5S-Spinach was monitored. After washout of ML-60218, cells were incubated with leptomycin B, an inhibitor of nuclear export of 5S (Murdoch et al., "Nuclear Export of 5S rRNA-containing Ribonucleoprotein Complexes Requires CRM1 and the RanGTPase Cycle," *Eur. J. Cell Biol.* 81:549 (2002), which is hereby incorporated by reference in its entirety). Under these conditions, 5S-Spinach accumulates in the nucleus. Upon removal of leptomycin-B, 5S-Spinach rapidly appeared in the cytosol, indicating highly efficient nucleocytoplasmic trafficking of 5S. The induction of 5S-Spinach in response to sucrose was also monitored. After washout of ML-60218, treatment of cells with sucrose resulted in rapid induction of 5S-Spinach over 60 min, and a higher total level of 5S-Spinach than in untreated cells (FIG. 4A). Unlike control cells, sucrose treatment caused 5S-Spinach to accumulate to higher levels in the nucleus than in the cytosol (FIG. 6), possibly reflecting saturation of the nuclear export machinery. Additionally, 5S-Spinach accumulated in cytoplasmic granular structures 30 min after sucrose treatment, consistent with stress granule formation. The time course of relocalization of 5S-Spinach into granules in cells not treated with ML-60218 was next examined. Prior to experimental treatment, 5S-Spinach exhibited diffuse nuclear and cytoplasmic localization (FIG. 4B). Following sucrose treatment, 5S-Spinach clustered into granules in as little as 9 min, with new granules continuing to form up to 30 min later. Together, these data show the ability of Spinach to the reveal intracellular dynamics of RNA in living cells.

Discussion of Examples 1-4

GFP turned out to be an ideal fluorescent system on which to base this fluorescent RNA technology. Nonspecific fluorescence activation by cellular constituents is a major problem that prevents the application of most conditionally fluorescent molecules in a cellular context. HBI derivatives exhibit minimal fluorescence in cells, indicating that cellular constituents are unable to suppress the nonradiative decay of the photoexcited fluorophore. This property, as well as low cytotoxicity upon illumination, makes this class of fluorophores ideal for applications involving live cells. RNA aptamers were able to induce fluorescence of GFP fluorophores, in many cases to levels that exceed fluorescent proteins. Because of the similarity of the RNA-fluorophore complexes to various GFP-related proteins, the brightest RNA was named after the vegetable spinach, in analogy to the fruits which have been used to name fluorescent proteins.

Spinach-DFHBI complexes exhibit EGFP-like fluorescence, in that this complex is strongly fluorescent and the fluorophore is a deprotonated HBI-derivative. Spinach is different from the fluorescent proteins in that it exhibits remarkable resistance to photobleaching, which likely reflects exchange of the bound fluorophore with fluorophore in solution, preventing the accumulation of photobleached RNA-fluorophore complexes. Moreover, fluorescence is observed shortly after Spinach transcription in cells, which contrasts with the delay in acquisition of fluorescence by nascent GFP due to the requirement for fluorophore maturation. Because these fluorophores are cell compatible, they can be used for various applications involving biological materials or living cells.

RNAs can be tagged with Spinach, providing a simple strategy for introducing a compact fluorescent tag for live cell imaging of RNAs. Existing techniques to genetically encode fluorescently tagged RNAs are problematic since they usually involve the recruitment of EGFP-fusion proteins which contain their own trafficking elements. Typically, the EGFP fusion contains a nuclear localization sequence (EGFP-NLS), which is used to reduce background fluorescent signals in the cytosol by targeting EGFP-NLS to the nucleus. However, as described by Tyagi, "Imaging Intracellular RNA Distribution and Dynamics in Living Cells," *Nat Methods* 6(5):331-338 (2009), which is hereby incorporated by reference in its entirety, the addition of an NLS or other targeting elements to RNAs raises concerns about the physiological relevance of the behavior of EGFP-NLS-tagged RNAs, since these RNAs are modified to bind 24-48 copies of MS2-GFP-NLS. As a result, these RNAs contain 24-48 NLS targeting elements which could affect their trafficking behavior (Tyagi, "Imaging Intracellular RNA Distribution and Dynamics in Living Cells," *Nat Methods* 6(5):331-338 (2009), which is hereby incorporated by reference in its entirety). Furthermore, the accumulation of MS2-GFP-NLS in the nucleus can also complicate nuclear imaging of RNA. An additional drawback of this approach is that the large payload of EGFP and EGFP-binding RNA elements makes this technique problematic for imaging small and medium-sized RNAs. The RNA tags described here provide the opportunity to genetically encode fluorescent RNAs with compact sequence tags and no NLS targeting elements, reducing the potential for perturbing the biological properties of the tagged RNA.

The results described here could be extended for using genetically encoded RNA-fluorophore complexes for other applications, including RNA-RNA and RNA-protein fluorescence resonance energy transfer, and simultaneous imaging of multiple RNAs. Therefore, this approach has the potential for developing a catalog of fluorescent tools for RNA-based applications akin to those previously developed for proteins.

Materials and Methods for Example 5-8

Reagents and Equipment:

Unless otherwise stated, all reagents were purchased from Sigma-Aldrich. Commercially available reagents were used without further purification. HPLC assays were performed on an Agilent 1100 series HPLC with a Zorbax C8 column. Absorbance spectra were recorded with a Thermo Scientific NanoDrop 2000 spectrophotometer with cuvette capability. Fluorescence excitation and emission spectra were measured with a Perkin Elmer LS-55 fluorescence spectrometer.

$EC_{50}$ Measurements:

Dose-response curves for each sensor in response to the target metabolite were determined by measuring the increase in fluorescence as a function of increasing target concentration in the presence of a fixed concentration of RNA sensor (10-50 nM) and a fixed concentration of fluorophore (10 µM). Curves were determined using a nonlinear regression analysis in Prism software and matched by least squares fitting to a standard dose-response model for 1:1 complexation.

Preparation of RNA Sensors and Mutants:

Secondary structure prediction was performed using Mfold online software. Mutated and truncated RNAs were created by ordering single stranded DNA templates (Integrated DNA Technologies) with the desired mutations or truncations and PCR amplifying these sequences to create double stranded DNA templates using primers which included a 5' T7 promoter sequence. PCR products were then purified with PCR purification columns (Qiagen) and used as templates for in vitro T7 transcription reactions (Epicentre).

Sensor Activation Rates:

A solution of RNA sensor (1 µM) and DFHBI (10 µM) was incubated with continuous stirring at 37° C. in a buffer containing 40 mM HEPES pH 7.4, 125 mM KCl and 1 mM $MgCl_2$. The target metabolite (1 mM) was then rapidly added to the stirring solutions and fluorescence emission was recorded over a 15 min period under continuous illumination at 37° C. using the following instrumental parameters: excitation wavelength, 460 nm; emission wavelength, 500 nm; increment of data point collection, 0.05 s; slit widths, 10 nm. The fluorescence increase was then plotted against exposure time and normalized to the maximum intensity of each fluorophore.

Cloning Sensors for Expression in *E. coli*:

ADP and SAM sensors were PCR amplified with primers containing either EagI or SacII restriction sites on the 5' or 3' ends of the sensor sequence, respectively. Sensors were then cloned into a plasmid containing a chimera of the human $tRNA^{Lys}_3$ scaffold, which has previously been shown to stabilize heterologous expression of RNA aptamers in *E. coli*. The entire tRNA-sensor construct was then PCR amplified with a forward primer containing a BglII site (italics) and a T7 promoter sequence (bold): 5'-CAG TCA AGA *TCT CGA TCC CGC GAA AT* TAA TAC GAC TCA CTA TAG GG-3' (SEQ ID NO: 49), and a reverse primer containing a XhoI site (italics) and a T7 terminator sequence (bold): 5'-CAT CAG *CTC GAG* CAA AAA ACC CCT CAA GAC CCG TTT AGA GGC CCC AAG GGG TTA TGC TA-3' (SEQ ID NO: 50). This PCR product was then cloned into a pET28c vector with BglII and XhoI restriction sites.

Live Cell Imaging of ADP Dynamics:

BL21-A Star *E. coli* cells (Invitrogen) were transformed with 40 ng of plasmid DNA expressing the tRNA-sensor chimeras in pET28c under the control of a T7 promoter. Cells were plated, grown overnight and single colonies were picked for inoculation in Luria Broth containing kanamycin (LB-Kan). At $OD_{600}$=0.4, 1 mM of IPTG was added to the culture and shaking was continued at 37° C. for more 2 hours. 100 uL of culture was then removed, spun down to pelleted the culture, and resuspended in 2 mL of pH 6.0 M9 minimal media. A 200 µl aliquot of resuspended culture was then plated on poly-L-lysine (PLL)-coated 24-well glass-bottom dishes (MatTek) and incubated for 45 minutes at 37° C. Adherent cells were washed twice and then incubated with 200 µM DFHBI in pH 6.0 M9 minimal media for 45 min at 37° C. Cells then were washed twice and incubated with M9 media containing 200 µM DFHBI and the appropriate carbon source (2 mg/ml glucose, 6.65 mg/ml potassium acetate, 4.05 mg/ml glycerol or 5.51 mg/ml succinate). Live fluorescence images were taken with a CoolSnap HQ2 CCD camera through a 60× oil objective mounted on a Nikon TE2000 microscope and analyzed with the NIS-Elements software. The filter set used was a sputter coated filter cube with excitation filter 470/40, dichroic mirror 495 (long pass) and emission filter 525/50 (Chroma Technology).

Biochemical Measurement of ADP Levels:

Cells transformed with ADP sensor were grown overnight in LB-Kan. Cultures were then diluted to $OD_{600}$=0.1 in 200 mL LB-Kan and grown to $OD_{600}$=0.4. Cells were then induced for 2 hours with 1 mM IPTG at 37° C. with constant shaking. The entire culture was split in two samples and then placed in a centrifuged for 5 min at 1,000×g. Pellets were then washed once and resuspended in 400 mL of M9 media containing 200 µM DFHBI and either 2.00 mg/ml glucose or 6.68 mg/ml potassium acetate as the carbon source. After a 2 hr incubation, cells incubated in glucose were switched a media containing acetate and cells incubated in acetate were switched to a media containing glucose. Aliquots of culture were removed every 30 min, pelleted, lysed, and ADP levels were measured with an ADP Fluorometric Assay Kit (Abcam) according to manufacturer's instructions.

Live Cell Imaging of SAM Accumulation:

Expression of the SAM aptamer and intracellular imaging was performed as described above for the ADP sensor: BL21-A Star *E. coli* cells (Invitrogen) were transformed with 40 ng of plasmid DNA expressing the tRNA-sensor chimeras in pET28c under the control of a T7 promoter. Cells were plated, grown overnight and single colonies were picked for inoculation in LB-Kan. At $OD_{600}$=0.4, 1 mM of IPTG was added to the culture and shaking was continued at 37° C. for more 2 hours. 100 µL of culture was then removed, spun down to pellet the culture, and resuspended in 2 mL of pH 6.0 M9 minimal media. A 200 µl aliquot of resuspended culture was then plated on PLL-coated 24-well glass-bottom dishes (MatTek) and incubated for 45 minutes at 37° C. Adherent cells were washed twice and then incubated with 200 µM DFHBI in pH 6.0 M9 minimal media for 2 hours at 37° C. Cells were then treated with methionine alone or methionine with inhibitors by adding 2 µl of a 100× stock of the compound to a final concentration of 50 µg/ml for L-methionine, 25 µM for adenosine periodate, and 2.5 µM for MT-DADMe-ImmA. Live fluorescence images were taken with a CoolSnap HQ2 CCD camera through a 60× oil objective mounted on a Nikon TE2000 microscope and analyzed with the NIS-Elements software. The filter set used was a sputter coated filter cube with excitation filter 470/40, dichroic mirror 495 (long pass) and emission filter 525/50 (Chroma Technology).

HPLC Measurement of Aggregate SAM Levels:

Cells transformed with SAM sensors were grown overnight in LB-Kan. Cultures were then diluted to $OD_{600}=0.1$ in 200 mL LB-Kan and grown to $OD_{600}=0.4$. Cells were then induced for 2 hours with 1 mM IPTG at 37° C. with constant shaking. The entire culture was centrifuged for 5 min at 1,000×g, pellets were resuspended and washed once with M9 media and then resuspended in 400 mL of M9 media containing 200 µM DFHBI and divided into two samples. Methionine (50 µg/ml) or vehicle was then added to either sample and cultures were incubated between 32-37° C. 25 ml aliquots were removed from methionine- and vehicle-treated sample at each time point, centrifuged for 5 min at 1,000×g, and flash frozen in liquid nitrogen. Cells were thawed on ice and lysed by resuspending the pellet in 300 µl of cold 4% perchloric acid. Insoluble material was then pelleted by spinning at 1,000×g for 5 min and the supernatant was transferred to a dialysis spin column with a 10,000 molecular weight cut off (Amicon) and spun at 10,000×g for 10 min at 4° C. A portion of the flow through (50 µl) was then injected on a Zorbax C8 column (Agilent) on an Agilent 1100 HPLC. Samples were loaded and eluted for 15 min with an aqueous buffer containing 3.6% acetonitrile, 40 mM ammonium phosphate, and 5 mM sodium 1-heptanesulfonate which was brought to pH 5.0 with hydrochloric acid. After each sample was eluted, the column was washed with a gradient of 3.6-25% acetonitrile for 30 min prior to the next samples being injected. SAM standards were used to calibrate SAM levels measured using this assay.

Population Analysis of SAM Production:

Population analysis was carried out using NIS-Elements software. Individual cells in a captured field were manually traced as Region of Interests (ROIs) and tracked through the different time points of image capture. Fluorescence intensity was then calculated by dividing the total fluorescence by the area for each ROI, which gives the mean intensity per unit area. Fold increase in fluorescence over time is calculated as the ratio of mean intensity at a desired time point and at time zero. Values in fold increase in fluorescence over time are plotted as frequency distributions or further used in statistical analyses.

Levene Test for Equality of Variances:

Levene tests for equality of variances were conducted using the Microsoft Excel QI Macros 2011 plug-in.

Example 5

Tolerance of Spinach Stem-Loop 2 to Manipulation

To assess the ability of Spinach to be fused to a small molecule-binding RNA aptamer in such a way that ligand binding activates the ability of Spinach to bind DFHBI, leading to fluorescence, it was first determined which portion of Spinach would tolerate the insertion of a metabolite-binding aptamer. As illustrated in FIG. 3C (SEQ ID NO: 6) and 11A (SEQ ID NO: 8), Spinach and its derivative are predicted to contain three stem-loop structures that encircle a large central loop. One of these stem-loops, stem-loop 2, was present in the original random library from which Spinach was derived. Stem-loop 2 of SEQ ID NO: 8 includes a highly stable 12-base stem-loop structure, composed of a 4-base pair stem and a stable UUCG tetraloop (FIG. 11A). Because stem-loop 2 was a fixed sequence in every library member, it may be less likely to make sequence-specific contacts with DFHBI, and more likely to have a structural role in DFHBI binding that could be exploited in sensor design.

Figure 11B:
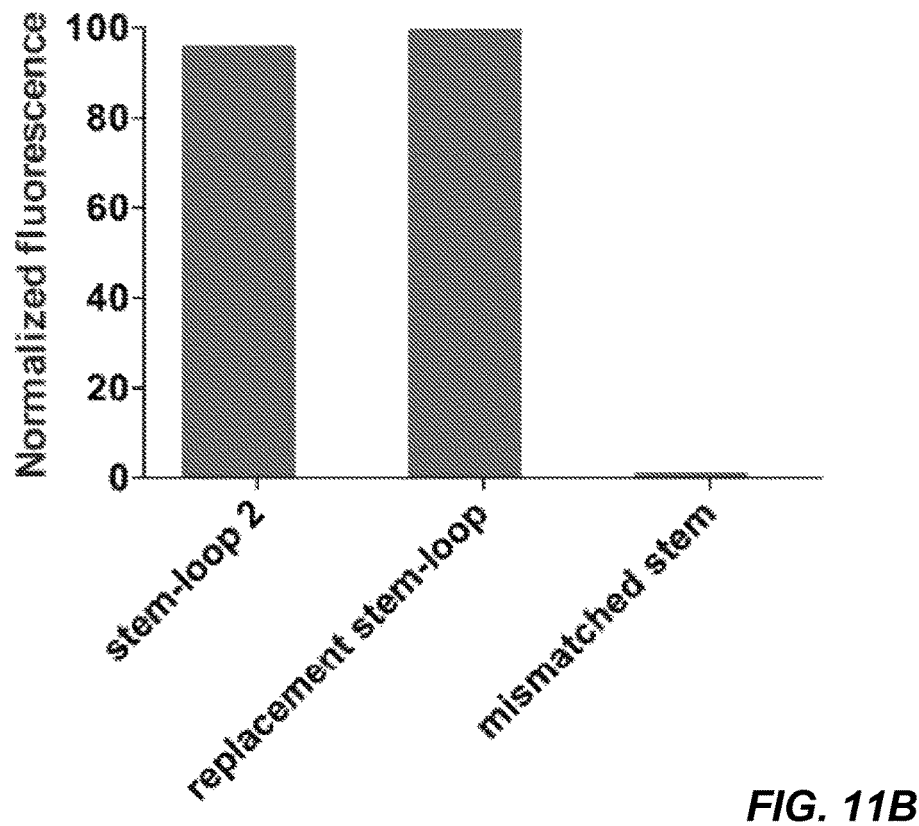
FIG. 11B is a graph confirming that stem-loop 2 has a structural role in Spinach-induced DFHBI fluorescence. Stem-loop 2 and the replacement stem-loop have nearly identical fluorescence intensities even though they are completely unrelated sequences. However, the mismatched stem reduces fluorescence intensity to baseline even though it retains the original UUCG tetraloop. This indicates that Spinach is amenable to changes in the sequence at the position of stem-loop 2; however, rigidification at the stem portion is necessary for fluorescence activation of DFHBI.

To determine if stem-loop 2 primarily has a structural role in Spinach, mutations were introduced at the stem-loop 2 positions shown in FIG. 11A to test the tolerance of Spinach to mutations at these positions. This was assayed by DFHBI fluorescence. In these experiments, the minimized Spinach structure (SEQ ID NO: 8) in which stem-loop 2 is predicted to sit adjacent to the large internal loop (FIG. 11A). This minimized Spinach sequence exhibits essentially identical fluorescence as the full length Spinach sequence. To determine if stem-loop 2 can be swapped with a different stem-loop with similar stability without perturbing Spinach-induced DFHBI fluorescence, the UUCG loop sequence was replaced with GAAA and the 4-base pair stem was replaced with a different but still complementary 4-base pair stem (FIG. 11A, SEQ ID NO: 9). These substitutions did not reduce DFHBI fluorescence (FIG. 11B). However, when mismatched bases were inserted in the stem region to prevent the formation of a duplex, DFHBI fluorescence was lost (FIG. 11B). Together, these data indicate that Spinach fluorescence requires a stable stem at the stem-loop 2 position.

It was then explored whether stem-loop 2 could be an entry point for the insertion of metabolite-binding aptamers. Small molecule-binding aptamers are often predominantly unstructured in solution, but become folded upon binding their targets (Hermann and Patel, "Adaptive Recognition by Nucleic Acid Aptamers," *Science* 287:820 (2000), which is hereby incorporated by reference in its entirety). If the aptamers are not unstructured without aptamers, judicious insertion of mutations can be used to reduce the stability at the desired temperature, such that folding will only occur on binding the analyte. If the metabolite-binding aptamer and Spinach share the critical stem required for Spinach-induced DFHBI fluorescence, metabolite binding can stabilize the stem, resulting in fluorescence. It was therefore realized that Spinach-based sensors could be constructed using a modular approach comprising: (1) a recognition module which constitutes a metabolite-binding aptamer, (2) a transducer module that has an essential structural role in stabilizing Spinach and "transmits" the metabolite binding event, and (3) a Spinach module (FIGS. 7A-C). This approach of using small molecules to allosterically regulate RNA structure has been used to develop small molecule-regulated ribozymes and aptamers (Tang and Breaker, "Rational Design of Allosteric ribozymes," *Chem. Biol.* 4:453 (1997); Tang and Breaker, "Mechanism for Allosteric Inhibition of an ATP-sensitive Ribozyme," *Nucleic Acids Res.* 26:4214 (1998); Soukup and Breaker, "Design of Allosteric Hammerhead Ribozymes Activated by Ligand-induced Structure Stabilization," *Structure* 7:783 (1999); Win and Smolke, "Higher-order Cellular Information Processing with Synthetic RNA Devices," *Science* 322:456 (2008), each of which is hereby incorporated by reference in its entirety), and these RNA devices have been shown to undergo structural rearrangements upon ligand binding which serves to increase ribozyme or other activities (Win et al., "Frameworks for Programming Biological Function through RNA Parts and Devices," *Chem. Biol.* 16:298 (2009); Buskirk et al., "Engineering a Ligand-dependent RNA Transcriptional Activator," *Chem. Biol.* 11:1157 (2004), each of which is hereby incorporated by reference in its entirety).

Example 6

Sensitive and Specific Detection of Metabolites Using Spinach-Based Sensors

Figures 8A, 8B, 8C:
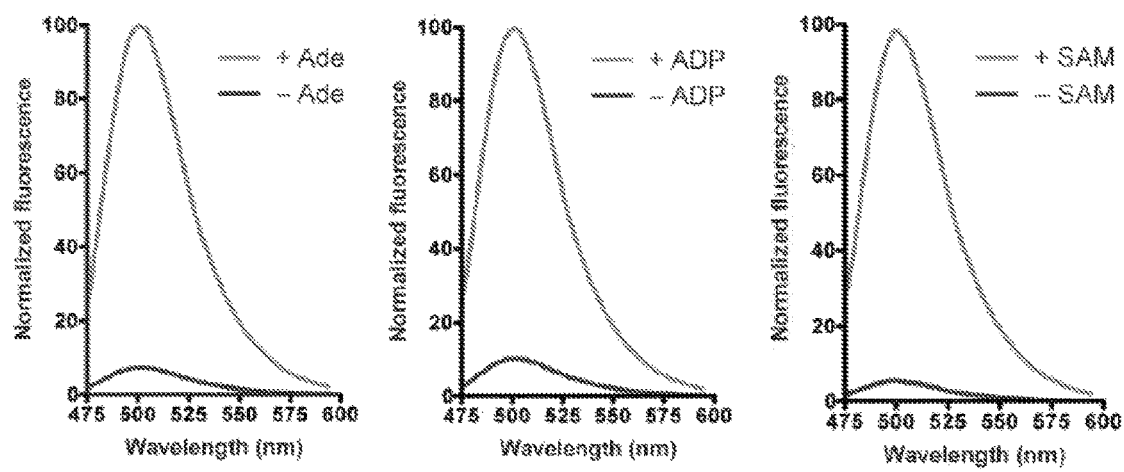
FIGS. 8A-I demonstrate that Spinach-based fluorescent sensors are selective and linearly detect metabolites at physiological concentrations.
Figure 8D:
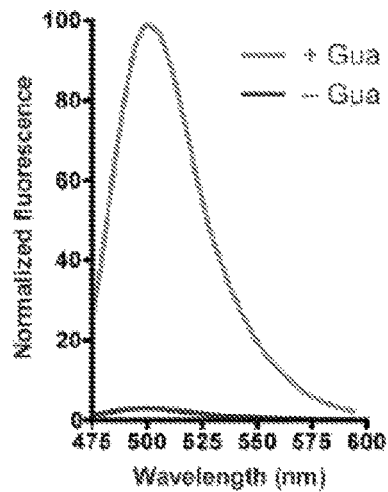
Figure 8E:
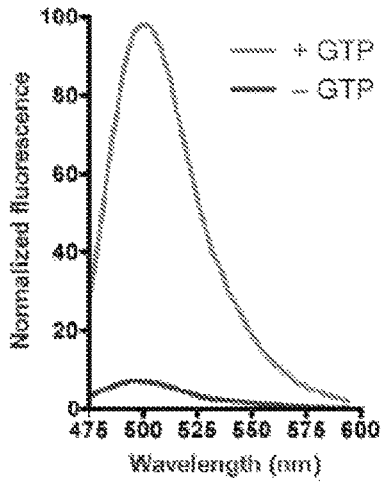
Figure 8F:
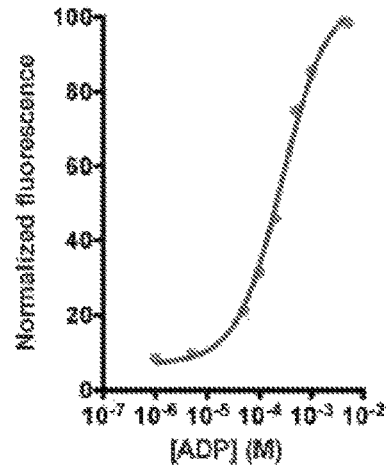
Figure 8G:
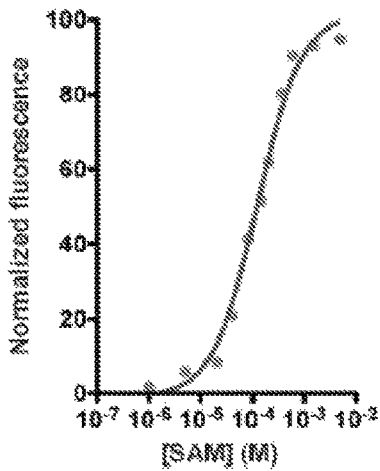
Figure 12A:
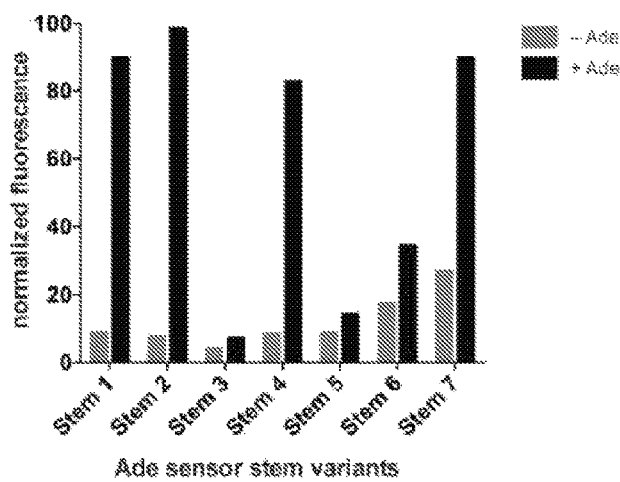
FIGS. 12A-C illustrate the optimization of stem transducer modules for adenosine, ADP and SAM sensors.
Figure 12B:
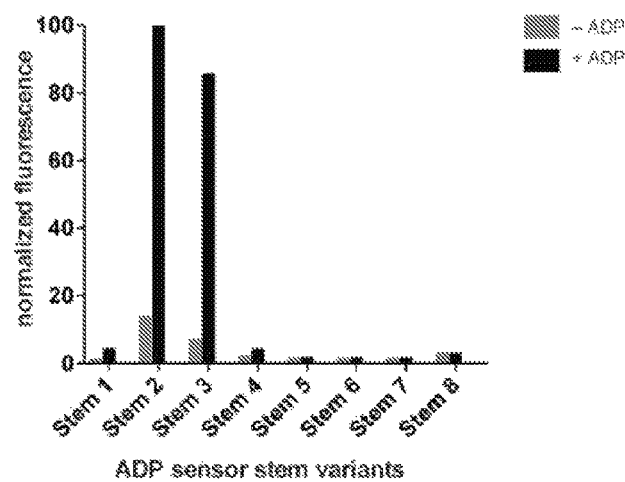
Figure 12C:
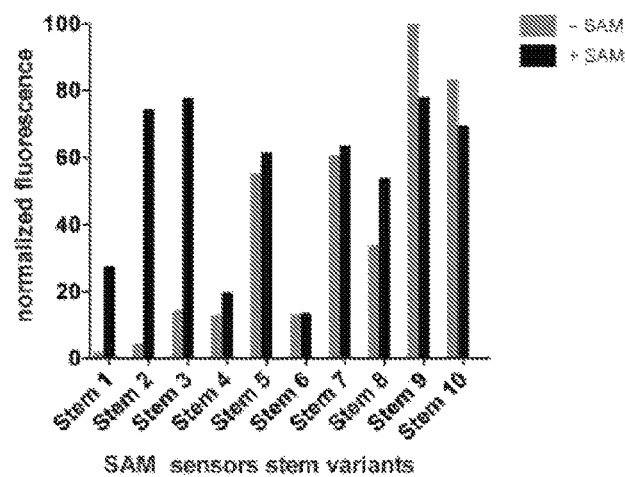

To determine if this strategy could regulate Spinach fluorescence, and was generally applicable to a wide range of metabolites, several metabolite-binding aptamers were fused to Spinach. The metabolite binding aptamers were chosen in part due to the structural diversity of the metabolites to which the aptamers bind, demonstrating the versatility of the approach. Aptamers which bind adenosine (Sassanfar and Szostak, "An RNA Motif that Binds ATP," *Nature* 364:550 (1993), which is hereby incorporated by reference in its entirety), adenosine 5'-diphosphate (ADP) (Sassanfar and Szostak, "An RNA Motif that Binds ATP," *Nature* 364:550 (1993), which is hereby incorporated by reference in its entirety), S-adenosylmethionine (SAM) (Lu et al., "Crystal Structures of the SAM-III/SMK Riboswitch Reveal the SAM-dependent Translation Inhibition Mechanism," *Nat. Struc. & Mol. Biol.* 15:1076 (2008), which is hereby incorporated by reference in its entirety), guanine (Batey et al., "Structure of a Natural Guanine-responsive Riboswitch Complexed with the Metabolite Hypoxanthine," *Nature* 432:411 (2004), which is hereby incorporated by reference in its entirety), and guanosine 5'-triphosphate (GTP) (Carothers et al., "Informational Complexity and Functional Activity of RNA Structures," *J. Am. Chem. Soc.* 126:5130 (2004), which is hereby incorporated by reference in its entirety) were each fused to Spinach via a transducer module, which was inserted in place of stem-loop 2 of Spinach. The transducer modules were designed so that hybridization of the stem sequences is thermodynamically unfavorable, because either (1) the transducer comprises sequences that are predicted to form short stems, (2) the sequences are composed of base pairs which form weaker interactions, such as A-U or G-U, (3) the sequences are predicted to form stems with mismatched base pairs, or (4) combinations thereof Using a series of different transducer modules, the sensors molecules were screened with for their ability to induce fluorescence in a metabolite-dependent manner (FIG. 12A, SEQ ID NOS: 17-23; FIG. 12B, SEQ ID NOS: 24-31; FIG. 12C, SEQ ID NOS: 32-41). The optimal sensors were chosen based on their low fluorescence in the absence of metabolite and the relative increase in fluorescence upon binding to the metabolite. The optimal adenosine sensor contained a transducer comprising a stem with base pairs primarily composed of weaker A-U and G-U pairs (FIG. 12A, stem 2 (SEQ ID NO: 18)). This sensor increased fluorescence nearly 20-fold in the presence of adenosine (FIG. 8A). In the case of the ADP and SAM sensors, shorter transducer modules with only 4 base pairs and 1 base pair, respectively, resulted in optimal metabolite-induced fluorescence (FIG. 12B, SEQ ID NO: 26; FIG. 12C, SEQ ID NO: 32). The ADP sensor exhibited a 20-fold increase in fluorescence in the presence of ADP and the SAM sensor became 25-fold more fluorescent in the presence of SAM (FIGS. 8B-C). The transducer modules for the guanine and GTP sensors were composed of truncated stems found in the parent aptamers. The sensors for guanine and GTP displayed a 32-fold and 15-fold increase in fluorescence, respectively (FIGS. 8D-E). Notably, there are no genetically encoded protein-based sensors or obvious approaches for designing FRET-based sensors for any of these metabolites.

Figure 13A:
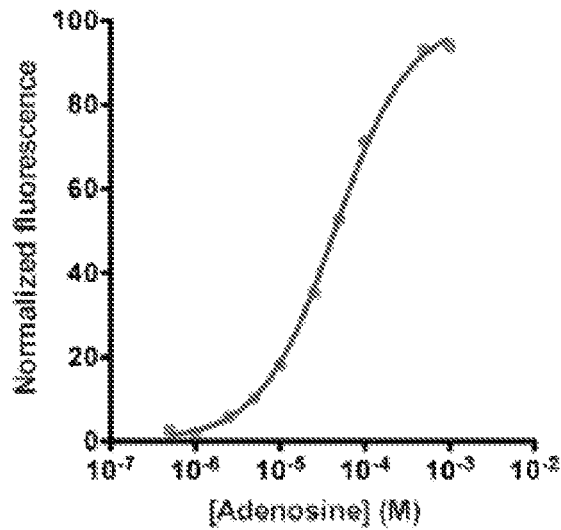
FIGS. 13A-H illustrate dose-response, specificity and kinetics experiments for RNA sensors.
Figure 13B:
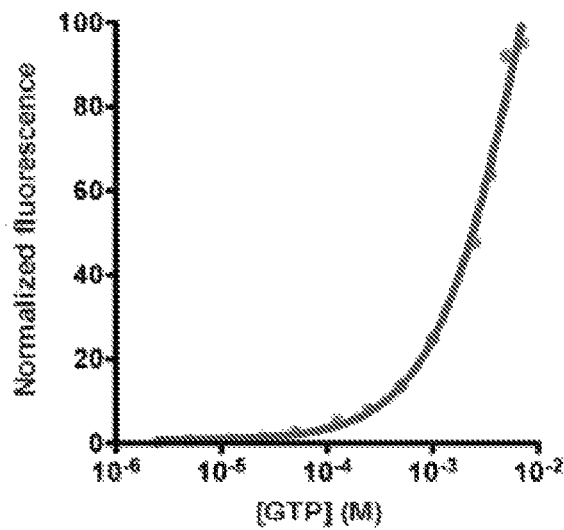
Figure 13C:
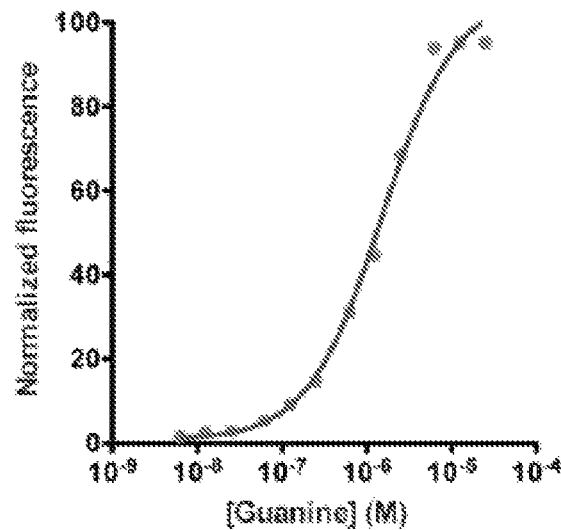

The adenosine, ADP, SAM and GTP sensors all gave linear increases in fluorescence within a range consistent with the endogenous cellular concentrations of each metabolite (FIGS. 8F-G, 13A-B) (Bennett et al., "Absolute Metabolite Concentrations and Implied Enzyme Active Site Occupancy in *Escherichia coli*," *Nat. Chem. Biol.* 5:593 (2009), which is hereby incorporated by reference in its entirety). The guanine sensor was highly sensitive and displayed an $EC_{50}$ lower than the concentration of guanine in cells (FIG. 13C) (Bennett et al., "Absolute Metabolite Concentrations and Implied Enzyme Active Site Occupancy in *Escherichia coli*," *Nat. Chem. Biol.* 5:593 (2009), which is hereby incorporated by reference in its entirety). These data indicate that the majority of these RNA-based sensors could be used to detect metabolites at concentrations consistent with their levels within cells.

Figure 13D:
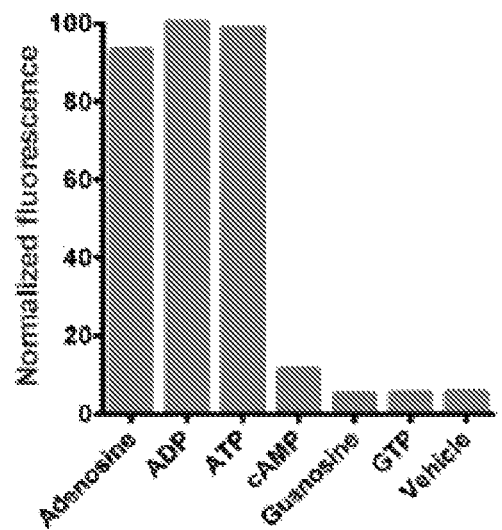
Figure 13E:
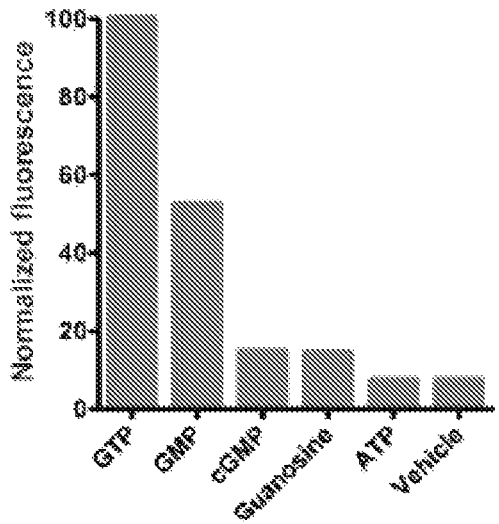
Figure 13F:
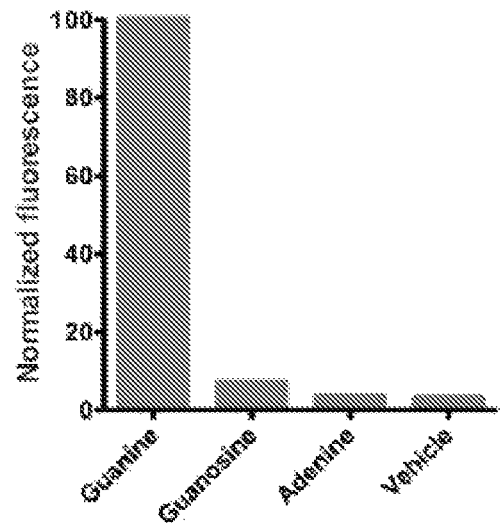

To determine the specificity of the RNA-based sensors, each sensor was tested against a panel of related metabolites. The adenosine sensor proved highly specific for adenosine over other nucleosides and adenosine 3'-phosphorylated nucleotides, but also fluoresces in the presence of adenosine 5'-phosphorylated-nucleotides (FIG. 13D), which is consistent with the known binding specificity of the parent aptamer (Sassanfar and Szostak, "An RNA Motif that Binds ATP," *Nature* 364:550 (1993), which is hereby incorporated by reference in its entirety). The GTP sensor showed minimal fluorescence in the presence of guanosine or cyclic guanosine 3',5'-monophophate (cGMP), but exhibits fluorescence, although to a lesser extent, in the presence of guanosine 5'-monophosphate (GMP) (FIG. 13E). The guanine sensor is optimally fluorescent at 10 µM guanine, but shows no fluorescence in the presence of equal concentrations of adenine or guanosine (FIG. 13F). Together, these results indicate that the RNA sensors can be selectively activated by specific target metabolites.

Figure 8H:
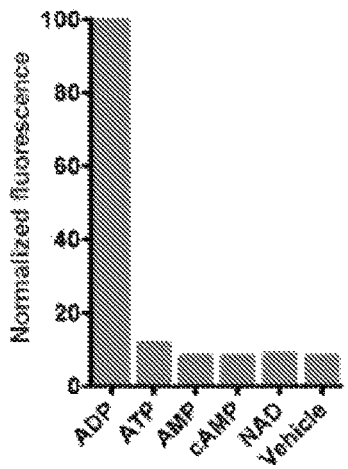
Figure 8I:
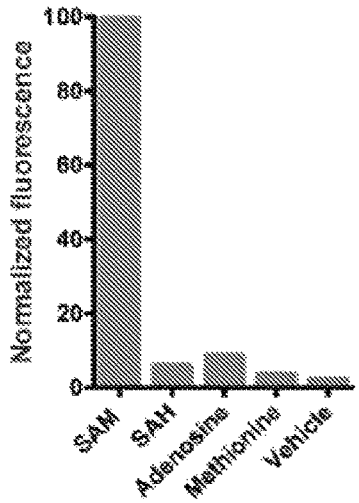
Figure 13G:
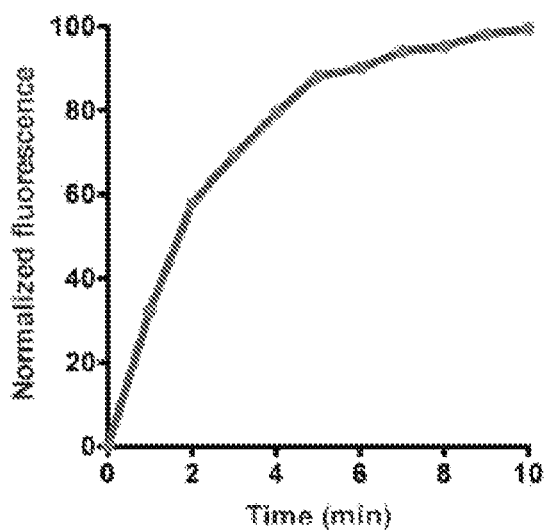
Figure 13H:
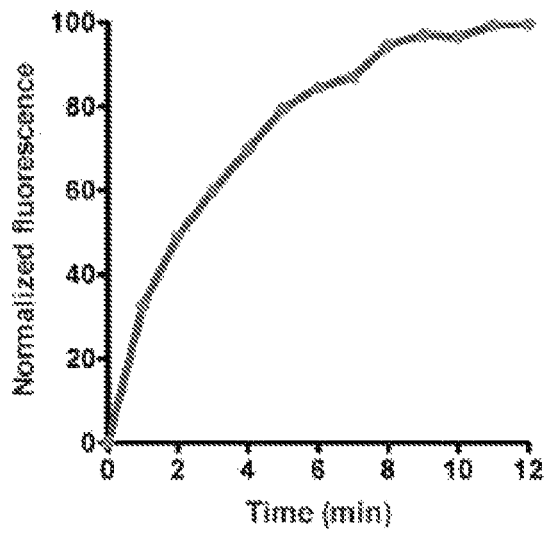

Next the sensors that bind ADP and SAM were more extensively characterized. Both ADP and SAM have important signaling roles in bacterial cells (Buckstein et al., "Characterization of Nucleotide Pools as a Function of Physiological State in *Escherichia coli*," *J. Bacteriol.* 190: 718 (2008); Lu, "5-Adenosylmethionine," *Inter. J. Bioch. & Cell Biol.* 32:391 (2000), each of which is hereby incorporated by reference in its entirety). Both the ADP and SAM sensors were found to be highly specific for their target metabolite. The ADP sensor is negligibly activated by other adenosine-containing nucleotides, such as adenosine 5'-triphosphate (ATP), adenosine 5'-monophosphate (AMP), adenosine 3',5'-monophophate (cAMP), or nicotinamide adenine dinucleotide ($NAD^+$), even at 1 mM concentrations of these compounds (FIG. 8H). The SAM sensor shows only minimal fluorescence with 1 mM S-adenosylhomocysteine (SAH), the byproduct of SAM-dependent methyltransferases, which differs from SAM by only a single methyl group (FIG. 8I). The intracellular concentration of SAH is several orders of magnitude below this level (Bennett et al., "Absolute Metabolite Concentrations and Implied Enzyme Active Site Occupancy in *Escherichia coli*," *Nat. Chem. Biol.* 5:593 (2009), which is hereby incorporated by reference in its entirety). Additionally, the SAM sensor is negligibly fluorescent in the presence of 1 mM adenosine or methionine, the two subunits from which SAM is derived. The rate of fluorescence activation following metabolite addition was also measured. Addition of either SAM or ADP resulted in increases in fluorescence in less than 10 s, with maximal levels of fluorescence within ~10 min (FIG. 13G-H).

Together, these data indicate that RNA-based sensors to ADP and SAM should be useful for measuring endogenous metabolite levels in living cells.

Example 7

Figure 9A:
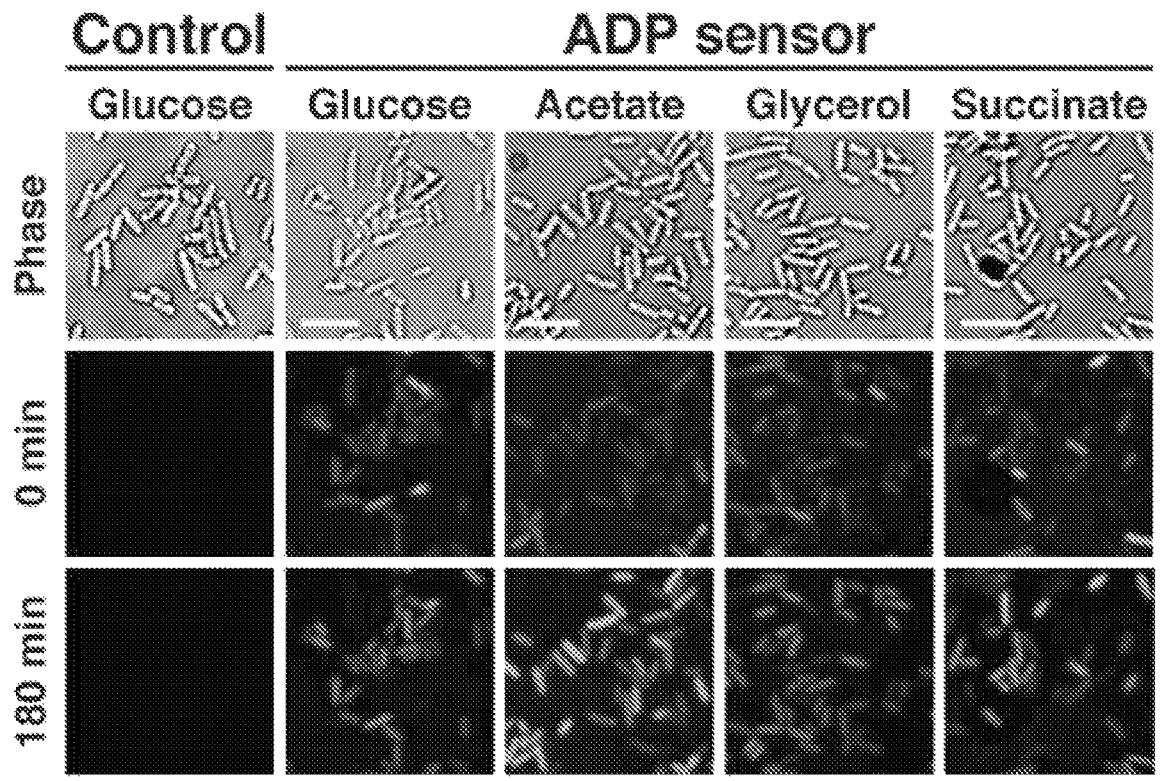
FIGS. 9A-E illustrate the live cell imaging of endogenous ADP and SAM levels.
Figure 9B:
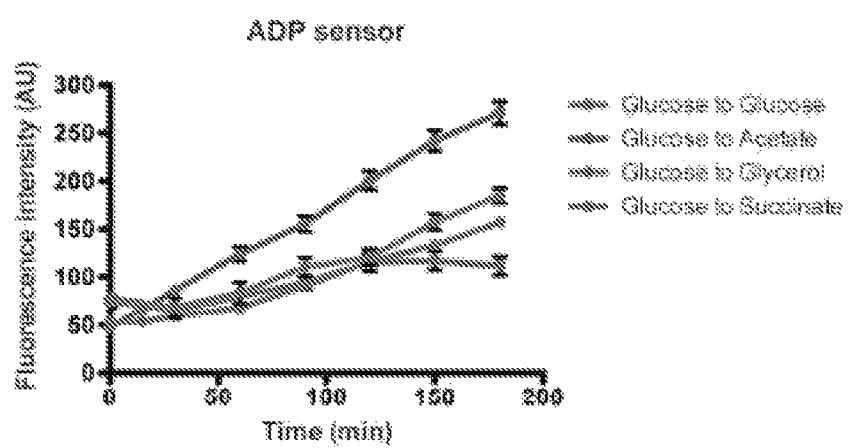
Figure 14A:
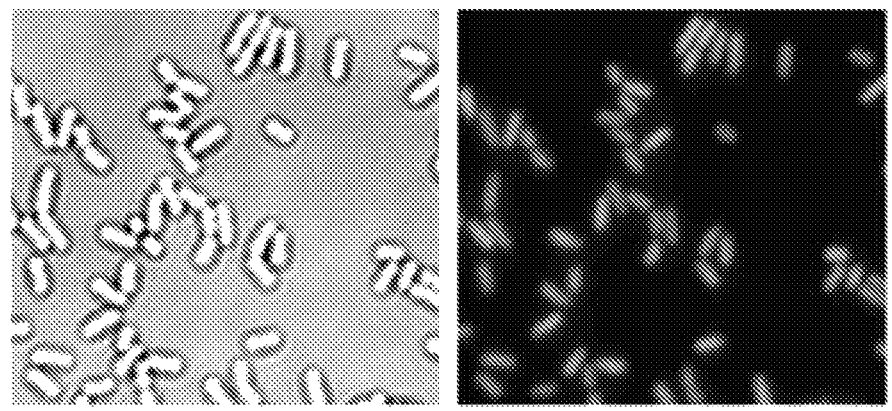
FIGS. 14A-B illustrate the uniformity in RNA expression level among Spinach-expressing *E. coli*.
Figure 14B:
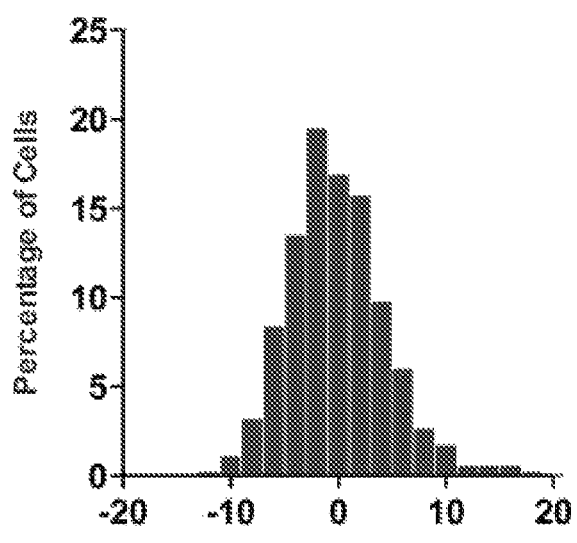

Fluorescence Imaging Reveals Intracellular ADP Dynamics Induced by Different Carbon Sources Given the positive in vitro results using the sensors, monitoring changes in intracellular metabolites in living cells was explored. ADP was examined first because of its importance as an early indicator of nutrient stress, which occurs when bacteria are unable to efficiently generate ATP from ADP (Buckstein et al., "Characterization of Nucleotide Pools as a Function of Physiological State in *Escherichia coli*," J. Bacteriol. 190:718 (2008); Lowry et al., "The Effect of Carbon and Nitrogen Sources on the Level of Metabolic Intermediates in *Escherichia coli*," J. Biol. Chem. 246:6511 (1971), each of which is hereby incorporated by reference in its entirety). Environmental conditions that lead to nutrient stress can protect *E. coli* from several antibiotics (Huisman and Kolter, "Sensing Starvation: A Homoserine Lactone-dependent Signaling Pathway in *Escherichia coli*," Science 265:537 (1994), which is hereby incorporated by reference in its entirety). To determine the dynamics of the induction of nutrient stress, *E. coli* were incubated in minimal media containing 200 μM DFHBI and 2 mg/ml glucose. Under these conditions, *E. coli* transformed with a plasmid expressing a control RNA exhibited negligible fluorescence, while *E. coli* expressing the ADP sensor exhibited moderate fluorescence (FIG. 9A), confirming that fluorescence in these cells derives from the sensor. When the media was switched to media containing acetate, a carbon source that induces nutrient stress because it requires activation of the glyoxylate bypass pathway (Cozzone, "Regulation of Acetate Metabolism by Protein Phosphorylation in Enteric Bacteria," Annu. Rev. Microbiol. 52:127 (1998), which is hereby incorporated by reference in its entirety), fluorescence levels rapidly rose, reaching a 1.8-fold increase over baseline levels within 30 min (FIG. 9B). Fluorescence levels continued to increase to nearly 6-fold over baseline levels by 3 hr (FIGS. 9A-B). The fluorescence increases in *E. coli* expressing the ADP sensor correlate with increases in endogenous ADP levels as measured using a standard biochemical assay, indicating that fluorescence levels reflect the intracellular ADP concentration. Other carbon sources, such as succinate or glycerol, did not substantially increase fluorescence in the ADP sensor-expressing cells, indicating that they are more readily metabolized than acetate (FIG. 9A-B). As a control, the effects of experimental treatments on *E. coli* transformed with a Spinach-expressing plasmid were also examined. *E. coli* exhibited uniform levels of Spinach fluorescence (FIGS. 14A-B), indicating that this expression system produces equivalent levels of RNA aptamer expression in each cell. There were no changes in fluorescence during any of the experimental treatments. These data confirm that the treatments did not nonspecifically affect Spinach fluorescence.

Figure 9C:
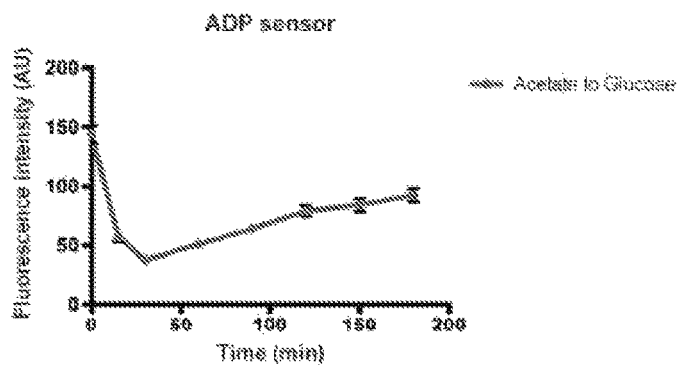

Finally, it was determined whether nutrient-starved *E. coli* rapidly readjust their metabolic state when switched to glucose-containing media. To test this, *E. coli* were cultured in 6.6 mg/ml potassium acetate for 2 hr, resulting in nutrient stress, as seen by the high baseline levels of ADP (FIG. 9C). The media was then exchanged with media containing 2 mg/ml glucose as the sole carbon source. After treating *E. coli* with glucose, ADP levels dropped 74% within 30 min, indicating that nutrient-limited *E. coli* rapidly readjust their metabolism to utilize glucose (FIG. 9C). Interestingly, after the drop in ADP levels, the levels began to slowly rise after 30 min, and gradually level out after 2.5 hr, indicating a readjustment to a new metabolic state after the initial introduction of glucose. Importantly, the observed trends were consistent with previous biochemical measurement of changes in ADP levels in *E. coli* following similar experimental treatments (Lowry et al., "The Effect of Carbon and Nitrogen Sources on the Level of Metabolic Intermediates in *Escherichia coli*," J. Biol. Chem. 246:6511 (1971), which is hereby incorporated by reference in its entirety). Together, these data demonstrate that dynamic changes in intracellular ADP levels can be monitored using an RNA-based sensor.

Example 8

Figure 9D:
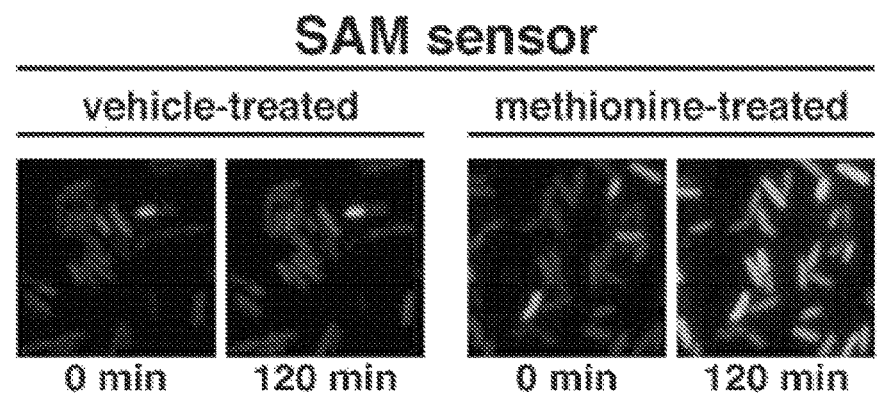
Figure 9E:
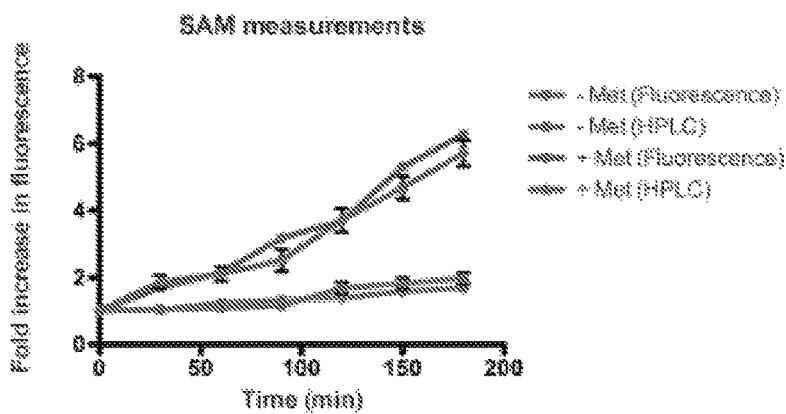

Monitoring Population Dynamics of SAM Synthesis Reveals Novel Roles for SAM Recycling Pathways in SAM Accumulation Using the SAM sensor, biosynthetic pathways that control intracellular levels of SAM were examined. SAM is a substrate for methyltransferase enzymes and potential antibacterial target, and it is synthesized in cells from methionine and ATP by SAM synthase (Lu, "S-Adenosylmethionine," Inter. J. Bioch. & Cell Biol. 32:391 (2000); Taylor et al., "Discovery of Novel Types of Inhibitors of S-adenosylmethionine Synthesis by Virtual Screening," J. Med. Chem. 52:5967 (2009), each of which is hereby incorporated by reference in its entirety). *E. coli* that are briefly cultured in methionine-free media exhibit low levels of SAM, which return to baseline levels upon addition of methionine (Winkler et al., "An mRNA Structure that Controls Gene Expression by Binding S-adenosylmethionine," Nat. Struc. & Mol. Biol. 10:701 (2003), which is hereby incorporated by reference in its entirety). *E. coli* transformed with a plasmid expressing the SAM sensor exhibited low levels of fluorescence when cultured in methionine-free media (FIG. 9D). To monitor changes in SAM levels, cells were treated with 50 μg/ml methionine and continuously imaged cellular fluorescence over 3 hr. During the time course of the experiment, the average fluorescence in SAM sensor-expressing *E. coli* increased over 6-fold on average in methionine-treated cells, whereas cells treated with vehicle showed only minimal changes in fluorescence (FIGS. 9D-E). Under the same conditions, the increases in SAM levels measured by an HPLC assay (Merali et al., "S-adenosylmethionine and *Pneumocystis carinii*," J. Biol. Chem. 275:14958 (2000), which is hereby incorporated by reference in its entirety) matched the increases in fluorescence, indicating that fluorescence levels linearly correlate with intracellular SAM concentrations (FIG. 9E). Control cells expressing Spinach showed no change in fluorescence under the same experimental conditions.

Figure 10A:
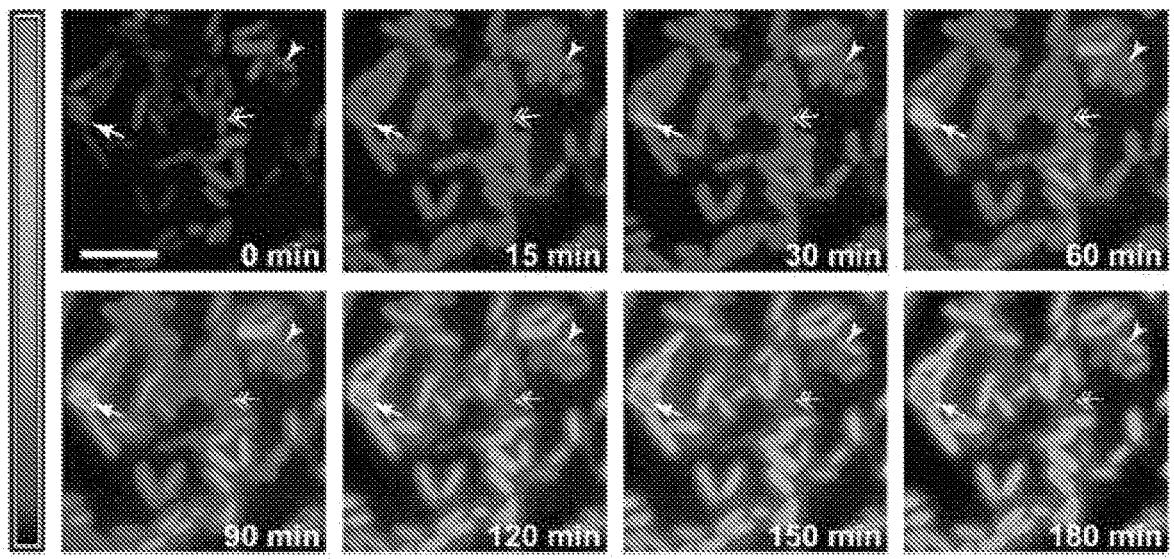
FIGS. 10A-F illustrate the population dynamics of SAM accumulation and recycling pathways in living cells.

Considerable cell-to-cell variability was observed in the manner in which intracellular SAM levels changed following methionine treatment (FIG. 10A). This inter-cell variability in SAM biosynthetic rates was different than the variability in ADP biosynthetic rates observed in the experiments using the ADP sensor, which appeared relatively uniform across all cells measured (see FIG. 9A). Although the majority of cells exhibited a continuous increase in SAM levels over the 3 hr time course of methionine treatment, a small percentage (~5%) of cells briefly increased and then rapidly decreased their intracellular SAM levels to baseline levels (FIG. 10A). Other cells exhibited a rapid and sustained increase in SAM levels up to 4-fold higher than the average cellular SAM level (FIGS. 10A-B).

Figure 10B:
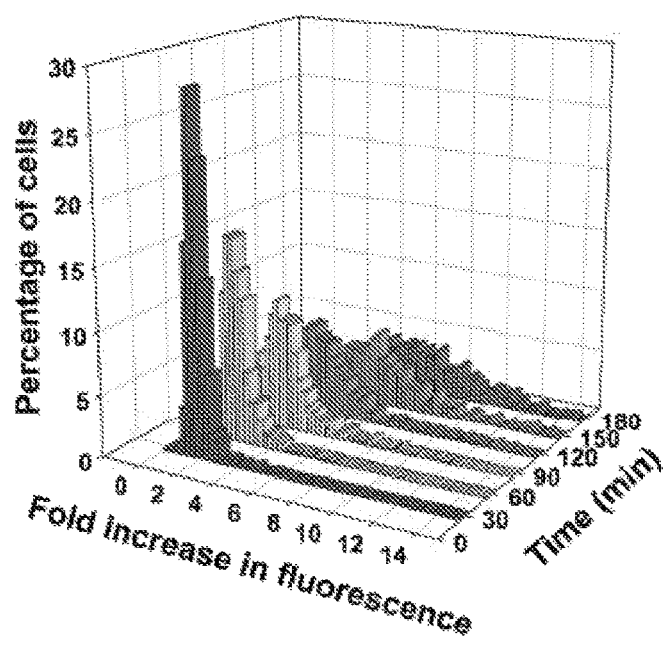
Figure 10C:
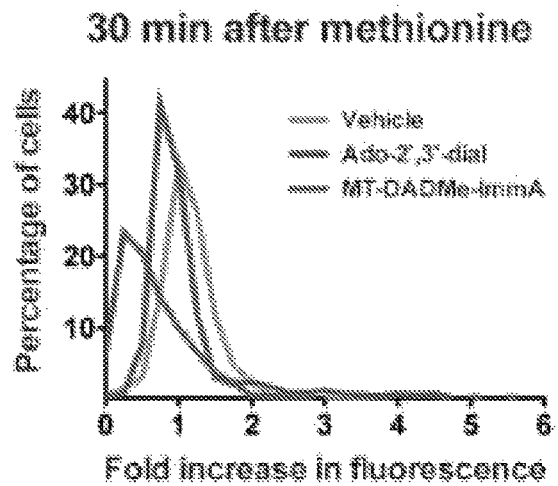

Over the time course of the experiment, the variation in rates of SAM accumulation led to a broad range of SAM levels in different cells within the population (FIGS. 10A-B). To measure the variability in SAM metabolism, SAM fluorescence was measured in individual cells every 15 min following methionine treatment. The variability in intracellular SAM levels was determined by measuring the fold change in SAM fluorescence relative to initial time point. As shown in FIG. 10B, the inter-cell variability in intracellular SAM levels following methionine treatment increased at each time point throughout the 3 hr time course. This distribution was non-Gaussian, and the variance between SAM levels in the population increased over 20-fold from 30 min to 3 hr after methionine treatment (FIG. 10B).

Figure 10D:
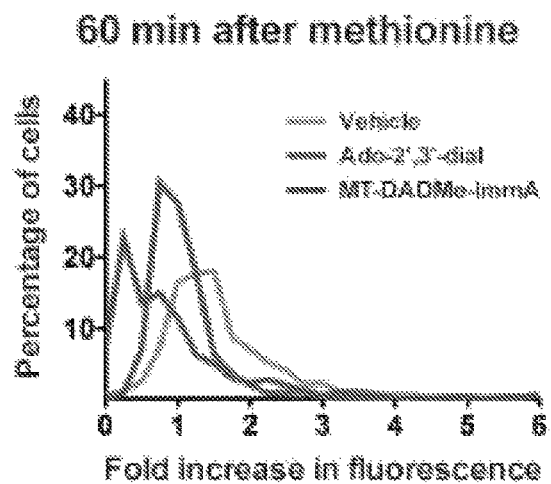
Figure 10E:
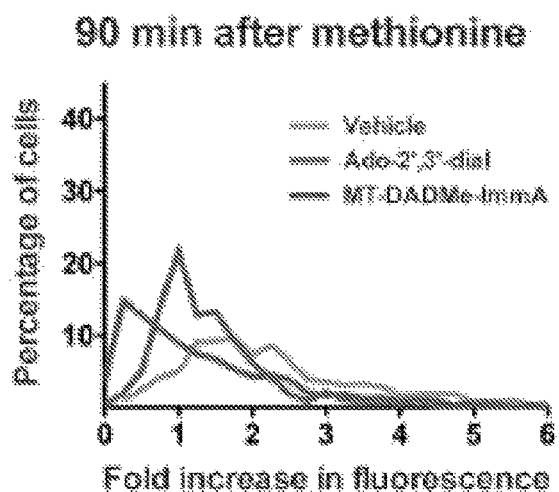
Figure 10F:
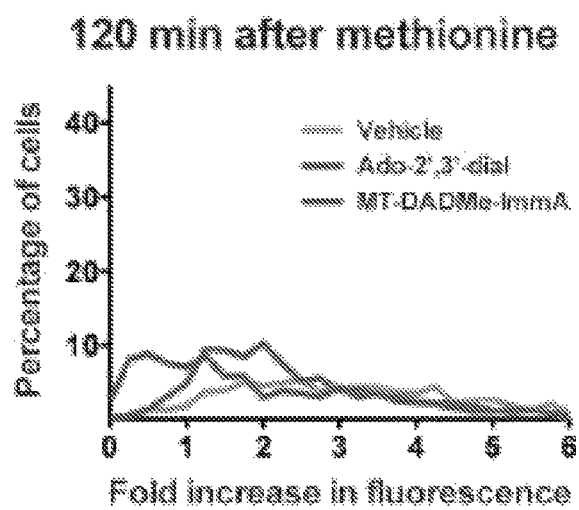
Figure 15:
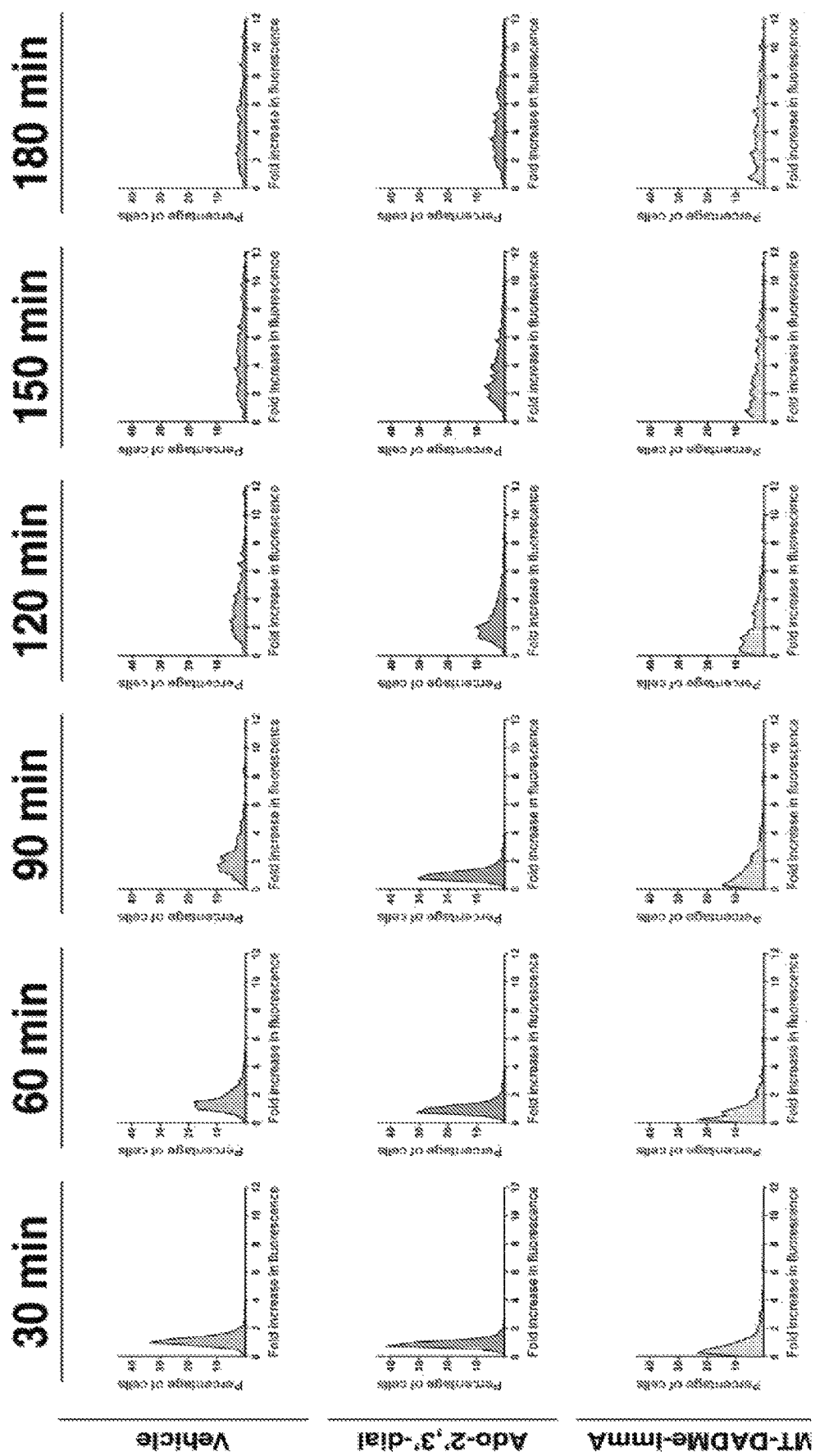
FIG. 15 is a panel of graphs showing a population analysis of SAM accumulation under different treatments Inhibition of different SAM recycling pathways causes distinct changes in SAM levels and population variance. Cells transformed with plasmids expressing the SAM sensor RNA were briefly methionine starved and then incubated with methionine (50 µg/ml) alone or with an SAH hydrolase inhibitor (Ado-2',3'-dial) or an SAH nucleosidase inhibitor (MT-DADMe-ImmA). Treatment with Ado-2',3'-dial resulted in very little change in the average SAM accumulation per cell over time, but did result in a significant reduction in the variability in SAM levels seen across the entire population. Treatment with Mt-DADMe-ImmA, on the other hand, resulted in a much greater reduction in average SAM accumulation levels, but actually increased the variability in SAM levels seen across the population.

The pathways that contribute to the variability in SAM metabolism in cells were also examined. Intracellular SAM levels are influenced by pathways that recycle SAH, the major byproduct of SAM-dependent enzymes (Lu, "S-Adenosylmethionine," *Inter. J. Bioch. & Cell Biol.* 32:391 (2000), which is hereby incorporated by reference in its entirety). Two pathways that convert SAH to methionine, the precursor used in SAM biosynthesis, include SAH hydrolase and SAH nucleosidase, which are also considered potential antimicrobial targets (Gutierrez et al., "Transition State Analogs of 5'-Methylthioadenosine Nucleosidase Disrupt Quorum Sensing," *Nat. Chem. Biol.* 5:251 (2009), which is hereby incorporated by reference in its entirety). To determine if either of these major SAH recycling pathways contribute to the variability in SAM levels in cells after methionine treatment, the effects of SAH hydrolase and SAH nucleosidase inhibitors were examined on the inter-cell variability in SAM levels in *E. coli*. *E. coli* treated with methionine in combination with the SAH hydrolase inhibitor adenosine-2',3'-dialdehyde (Ade-2',3'-dial) (Wang et al., "Riboswitches that Sense S-adenosylhomocysteine and Activate Genes Involved in Coenzyme Recycling," *Mol. Cell* 29:691 (2008); Hermes et al., "Influence of an Altered Methylation Potential on mRNA Methylation and Gene Expression in HepG2 cells," *Exp. Cell Res.* 294:325 (2004), each of which is hereby incorporated by reference in its entirety), showed only a slight decrease in the average SAM levels at each time point compared to populations treated with methionine in combination with vehicle (FIGS. 10C-F; FIG. 15). However, Ade-2',3'-dial-treated cells exhibited markedly reduced inter-cell variability in SAM levels compared to vehicle-treated cells at each time point (FIGS. 10C-F; FIG. 15). This difference was most noticeable 1 hr after methionine treatment and then began to lessen by 2 hr after treatment (FIGS. 10D-F; FIG. 15). In contrast, populations treated with the SAH nucleosidase inhibitor, MT-DADMe-Immucillin-A (MT-DADMe-ImmA) (Gutierrez et al., "Transition State Analogs of 5'-Methylthioadenosine Nucleosidase Disrupt Quorum Sensing," *Nat. Chem. Biol.* 5:251 (2009), which is hereby incorporated by reference in its entirety), showed a large decrease in the average accumulation of SAM in cells compared to vehicle-treated populations, but retained considerable variability in total SAM levels at all time points (FIGS. 10D-F; FIG. 15). However, the overall distribution of SAM levels was significantly altered compared to vehicle treatment, confirming that the SAM nucleosidase-dependent recycling pathway has a substantial role in SAM metabolism in *E. coli*. These data show that a different RNA-based sensor can be used to show the dynamic changes in an intracellular metabolite in real time. Together, these experiments indicate that single cell imaging of SAM levels can reveal sources of cell-to-cell variation in SAM metabolism.

Example 8

Design and Use of Spinach-Based Protein Sensor

Figure 16B:
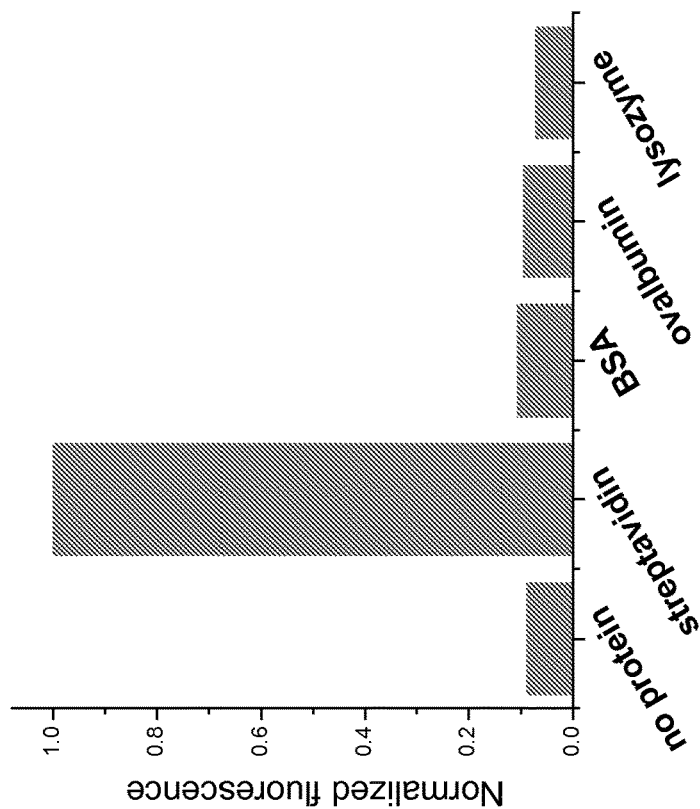
FIG. 16B is a graph illustrating the responsiveness of the Spinach-streptavidin sensor to micromolar concentrations of solutions of either streptavidin, BSA, ovalbumin, or lysozyme. These results show that specific fluorescence activation occurs only in solutions that contained streptavidin. All other proteins fail to increase fluorescence above background levels. In all samples shown, DFHBI, the Spinach-binding fluorophore was included.
Figure 16A:
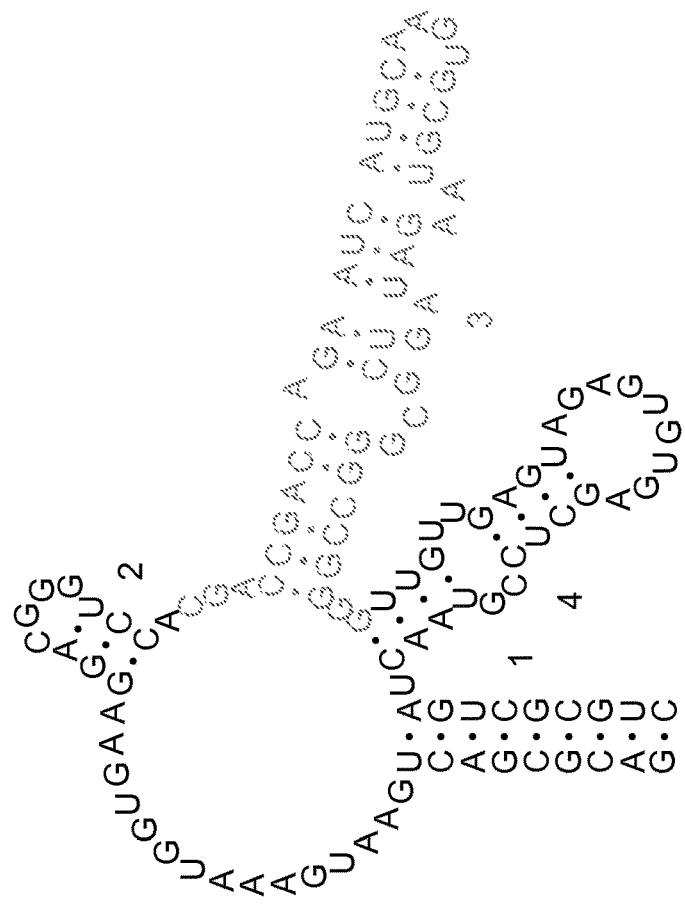
FIG. 16A illustrates the RNA sequence (SEQ ID NO: 44) and secondary structure of Spinach-based streptavidin sensor molecule. In this sensor, a portion of Spinach was replaced with an aptamer sequence that binds streptavidin (Srisawat and Engelke, "Streptavidin Aptamers: Affinity Tags for the Study of RNAs and Ribonucleoproteins, RNA 7:632-41 (2001), which is hereby incorporated by reference in its entirety). RNA structure is shown as predicted by Mfold web-based software (Zuker, "Mfold Web Server for Nucleic Acid Folding and Hybridization Prediction," *Nucl. Acids Res.* 31(13): 3406-3415 (2003), which is hereby incorporated by reference in its entirety).

It was next examined whether Spinach can similarly be modified to exhibit fluorescence in the presence of a specific protein. Using the same strategy from Example 5-7, a streptavidin aptamer (Srisawat and Engelke, "Streptavidin Aptamers: Affinity Tags for the Study of RNAs and Ribonucleoproteins, RNA 7:632-41 (2001), which is hereby incorporated by reference in its entirety) was fused to Spinach, and the transducer domain was optimized. The resulting RNA molecule is illustrated in FIG. 16A. The sensor was separately exposed to solutions containing micromolar concentrations of streptavidin, ovalalbumin, BSA, and lysozyme. It was found that the fluorescence of this RNA was selectively activated by streptavidin, but not by ovalbumin, BSA, or lysozyme (FIG. 16B). Thus, the approach is generalizable not just to small molecules, but also proteins.

Discussion of Examples 5-8

Examples 5-8 demonstrate a general platform for the generation of genetically encoded sensors that detect small molecules in living cells. Unlike the protein-based genetically encoded sensors that have been utilized until now, these sensors are composed of RNA and function by allosteric regulation of Spinach fluorescence. Because RNA aptamers that bind to a wide range of biomolecules can be readily and quickly generated (Cho et al., "Applications of Aptamers as Sensors," *Annu. Rev. Anal. Chem.* 2:241 (2009); Stoltenburg et al., "SELEX—A (R)evolutionary Method to Generate High-affinity Nucleic Acid Ligands," *Biomol. Eng.* 24:381 (2007), each of which is hereby incorporated by reference in its entirety), the strategies described in the preceding Examples enable the design of sensors that exhibit fluorescence in response to an exceptionally diverse variety of molecules. Expression of these sensors in living cells was shown to allow changes in metabolite levels in individual cells to be monitored in response to perturbations.

The major limitation that has prevented intracellular imaging of most metabolites is the absence of metabolite-binding proteins that undergo conformational changes sufficient to affect FRET. In most cases proteins that bind target molecules of interest either have not been identified, or bind to target molecules but do not exhibit sufficiently large conformational changes. The sensors described here take advantage of two features of RNA aptamers to overcome these problems. First, RNA aptamers can be generated against virtually any target molecule (Cho et al., "Applications of Aptamers as Sensors," *Annu. Rev. Anal. Chem.* 2:241 (2009); Stoltenburg et al., "SELEX—A (R)evolutionary Method to Generate High-affinity Nucleic Acid Ligands," *Biomol. Eng.* 24:381 (2007), each of which is hereby incorporated by reference in its entirety). Additionally, RNA aptamers can routinely be selected such that they exhibit high selectivity towards target molecules versus molecules that differ by as little as a methyl or phosphate group (Sazani et al., "A Small Aptamer with Strong and Specific Recognition of the Triphosphate of ATP," *J. Am. Chem. Soc.* 126: 8370 (2004); Jenison et al., "High-resolution Molecular Discrimination by RNA," *Science* 263:1425 (1994), each of which is hereby incorporated by reference in its entirety). Selection techniques have been described so that the affinity of aptamers can be tuned to yield aptamers that bind target molecules with desired affinities, typically in the nanomolar or micromolar range (Stoltenburg et al., "SELEX—A (R)evolutionary Method to Generate High-affinity Nucleic Acid Ligands," *Biomol. Eng.* 24:381 (2007), which is hereby incorporated by reference in its entirety). Second, RNA aptamers commonly transition from an unfolded to a folded state upon binding small molecule targets (Hermann and Patel, "Adaptive Recognition by Nucleic Acid Aptamers," *Science* 287:820 (2000), which is hereby incorporated by reference in its entirety). The sensors described here take advantage of this mode of ligand binding to allosterically regulate Spinach.

The RNA-based sensors described here produce over 20-fold increases in fluorescence upon metabolite binding, which directly correlate with increases in the intracellular concentrations measured using biochemical assays. This is considerably larger than genetically encoded sensors which rely on FRET, and typically result in only 30-100% increases in FRET levels upon target binding (Lemke and Schultz, "Principles for Designing Fluorescent Sensors and Reporters," *Nat. Chem. Biol.* 7:480 (2011), which is hereby incorporated by reference in its entirety). In cases where the cell has uneven morphology, normalizing sensor fluorescence to another plasmid-encoded fluorophore, such as red fluorescent protein, would ensure that changes in fluorescence signals are not due to local volume differences or cell-to-cell variation in sensor expression. An additional consideration in the design of the sensors is that the $EC_{50}$ should be larger than the endogenous concentration of the metabolite in the cell. If the sensor is too sensitive, the sensor may be fully saturated at physiologic levels of the metabolite, and therefore unable to detect changes in metabolite levels. Tuning of the metabolite-binding aptamer using mutagenesis or selection techniques (Soukup et al., "Generating New Ligand-binding RNAs by Affinity Maturation and Disintegration of Allosteric Ribozymes," *RNA* 7:524 (2001); Huang and Szostak, "Evolution of Aptamers with a New Specificity and New Secondary Structures from an ATP Aptamer," *RNA* 9:1456 (2003), each of which is hereby incorporated by reference in its entirety), will be important to match the sensitivity of the sensor with the endogenous metabolite concentration.

A major aspect of these sensors is that they use DFHBI, which does not exhibit nonspecific fluorescence activation upon incubation with cells, making background fluorescence from the unbound fluorophore minimal. This is in contrast to other fluorophores that can be activated by aptamers, or fluorophores which bind metabolite-regulated aptamers, such as malachite green, Hoechst 65442, and cyanine dyes (Furutani et al., "Modular Blue Fluorescent RNA Sensors for Label-free Detection of Target Molecules," *Molecular Biosystems* 6:1569 (2010); Stojanovic and Kolpashchikov, "Modular Aptameric Sensors," *J. Am. Chem. Soc.* 126:9266 (2004); Sando et al., "Transcription Monitoring Using Fused RNA with a Dye-binding Light-up Aptamer as a Tag: A Blue Fluorescent RNA," *Chem. Commun.* 33:3858 (2008); Babendure et al., "Aptamers Switch on Fluorescence of Triphenylmethane Dyes," *J. Am. Chem. Soc.* 125:14716 (2003); Constantin et al., "Synthesis of New Fluorogenic Cyanine Dyes and Incorporation into RNA Fluoromodules," *Org. Lett.* 10:1561 (2008), each of which is hereby incorporated by reference in its entirety), which are more susceptible to nonspecific fluorescence upon incubation with cells or biological materials (Constantin et al., "Synthesis of New Fluorogenic Cyanine Dyes and Incorporation into RNA Fluoromodules," *Org. Lett.* 10:1561 (2008); Ippen et al., "Picosecond Recovery Dynamics of Malachite Green," *Chem. Phys. Lett.* 38:611 (1976); Kim and Fleming, "Reorientation and Isomerization of Trans-stilbene in Alkane Solutions," *J. Phys. Chem.* 92:2168 (1988); Nagele et al., "Femtosecond Photoisomerization of Cis-azobenzene," *Chem. Phys. Lett.* 272:489 (1997); Sension et al., "Femtosecond Laser Studies of the Cis-stilbene Photoisomerization Reactions," *J. Chem. Phys.* 98:6291 (1993); Sundstrom and Gillbro, "Viscosity-dependent Isomerization Yields of Some Cyanine Dyes—A Picosecond Laser Spectroscopy Study," *J. Phys. Chem.* 86:1788 (1982); Dugave and Demange, "Cis-trans Isomerization of Organic Molecules and Biomolecules: Implications and Applications," *Chem. Rev.* 103: 2475 (2003); Meech, "Excited State Reactions in Fluorescent Proteins," *Chem. Soc. Rev.* 38:2922 (2009), each of which is hereby incorporated by reference in its entirety). DFHBI also has negligible phototoxicity (see Examples 1-4), which along with its brightness and low background make Spinach-based sensors particularly useful for the design of genetically encoded sensors for imaging metabolites in living cells. Similar approaches can be used for the other RNA-fluorophore complexes that were described in PCT Application Publ. No. WO/2010/096584 to Jaffrey and Paige, which is hereby incorporated by reference in its entirety. or other RNA-fluorophore complexes that would be generated using similar approaches and suitable fluorophores.

Example 9

Derivation of Spinach Sequence to Enhance Fluorescence

Further modifications to Spinach were made in the same manner as described in Example 3, supra. These included modifications to the central loop, the stem formed between 5' and 3' ends, as well as stem-loops 1, 2, and 3. FIG. 17 illustrates the RNA sequences and secondary structures of Spinach (SEQ ID NO: 10), and five derivatives thereof, which are designated Spinach-2 (SEQ ID NO: 12), Spinach-4 (SEQ ID NO: 13), Spinach-6 (SEQ ID NO: 14), Spinach-7 (SEQ ID NO: 15), and Spinach-13 (SEQ ID NO: 11). RNA structure is shown as predicted by Mfold web-based software (Zuker, "Mfold Web Server for Nucleic Acid Folding and Hybridization Prediction," *Nucl. Acids Res.* 31(13): 3406-3415 (2003), which is hereby incorporated by reference in its entirety). Substitutions present in the derivatives, relative to Spinach, are shown with a box formed around the base.

Figure 18:
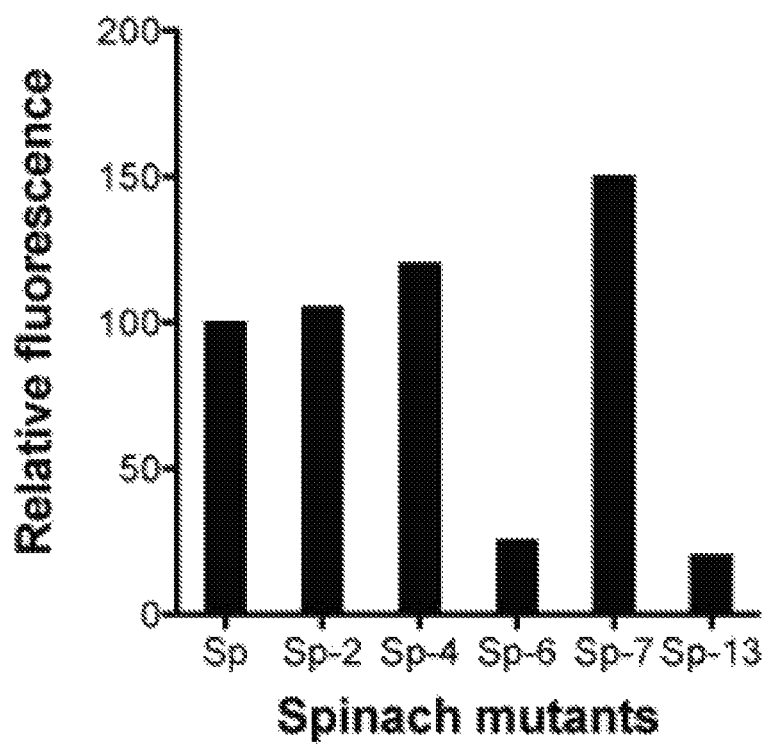
FIG. 18 is a graph illustrating the relative fluorescence of the Spinach derivatives compared to Spinach. In all samples shown, the same concentration of DFHBI, the Spinach-binding fluorophore, was included. While Spinach-2 produced comparable fluorescence, Spinach-4 and Spinach-7 exhibited enhanced fluorescence and Spinach-6 and Spinach-13 exhibited greatly reduced fluorescence.

FIG. 18 is a graph illustrating the relative fluorescence of the Spinach derivatives compared to Spinach. In all samples shown, the same concentration of DFHBI, the Spinach-binding fluorophore, was included. As demonstrated by Spinach-6 and Spinach-13, which exhibited greatly reduced fluorescence, modifications to stem-loops 1 and 3 were not tolerated. In contrast, modifications to the 5' and 3' stem formation, the central loop, and stem-loop 2 were either tolerated or led to much improved fluorescence. Spinach-4 and Spinach-7, both of which exhibited enhanced fluorescence, were the only derivatives that lacked modifications of stem-loops 1 and 3 but possessed modification to stem-loop 2.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed is:

1. A nucleic acid molecule that binds to a compound according to formula I below:

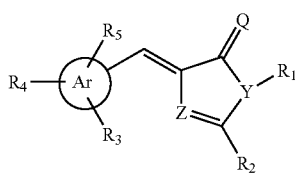

(I)

wherein,
Q is S or O;
Y is N;
Z is N or C($R_{10}$);
Ar is phenyl;
$R_1$ is —$(CH_2)_n$—$R_6$ where n is an integer greater than or equal to 1;
$R_2$ is methyl, mono-halo methyl, di-halo methyl, tri-halo methyl, aldoxime, O-methyl-aldoxime, iminomethyl, carboxylic acid, thioic acid, (thio)amido, alkyl(thio)amido, unsubstituted or substituted phenyl with up to three substituents ($R_7$-$R_9$), (meth)acrylate, or $C_{2-8}$ unsaturated hydrocarbon optionally terminated with amine, amide, carboxylic acid, ester, enone, oxime, O-methyl-oxime, imine, nitromethane, nitrile, ketone, mono-halo, di-halo, tri-halo, nitro, cyano, acrylonitrile, acrylonitrile-enoate, acrylonitrile-carboxylate, acrylonitrile-amide, alkylester, or a second aromatic or hetero-aromatic ring;
$R_3$-$R_5$ are independently selected from H, hydroxy, alkyl, alkoxy, fluoro, chloro, bromo, mono-halo alkoxy, di-halo alkoxy, tri-halo alkoxy, amino, alkylamino, dialkylamino, (thio)amido, alkyl(thio)amido, alkylthio, cyano, mercapto, nitro, mono-halo methyl, di-halo methyl, tri-halo methyl, ketone, carboxylic acid, thioc acid, alkylester, a surface-reactive group, a solid surface, and a functional group that can be linked to a reactive group on the solid surface;
$R_6$ is hydroxy, alkoxy, fluoro, chloro, bromo, mono-halo methyl, di-halo methyl, tri-halo alkoxy, amino, alkylamino, dialkylamino, (thio)amido, alkyl(thio)amido, alkylthio, cyano, mercapto, nitro, mono-halo methyl, di-halo methyl, tri-halo methyl, ketone, carboxylic acid, or alkylester; and
$R_7$-$R_{10}$ are independently selected from H, hydroxy, alkyl, alkoxy, fluoro, chloro, bromo, amino, alkylamino, dialkylamino, (thio)amido, alkyl(thio)amido, alkylthio, cyano, mercapto, nitro, mono-halo methyl, di-halo methyl, tri-halo methyl, ketone, carboxylic acid, thioic acid, and alkylester, wherein binding of the nucleic acid molecule to the compound of formula (I) induces fluorescence of said compound.

2. The compound according to claim 1, wherein $R_6$, is mono-halo methyl, di-halo methyl, or tri-halo methyl.

3. The compound according to claim 1, wherein Ar is phenyl substituted with $R_3$, $R_4$, and $R_5$.

4. The compound according to claim 1, wherein $R_3$-$R_5$ are independently selected from hydroxy, alkoxy, fluoro, chloro, bromo, mono-halo alkoxy, di-halo alkoxy, tri-halo alkoxy, mono-halo methyl, di-halo methyl, and tri-halo methyl.

5. A molecular complex comprising:
a compound according to formula I below:

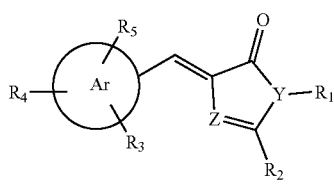

(I)

wherein,
Q is S or O;
Y is N;
Z is N or $C(R_{10})$;
Ar is phenyl;
$R_1$ is —$(CH_2)_n$—$R_6$ where n is an integer greater than or equal to 1;
$R_2$ is methyl, mono-halo methyl, di-halo methyl, tri-halo methyl, aldoxime, O-methyl-aldoxime, iminomethyl, carboxylic acid, thioic acid, (thio)amido, alkyl(thio)amido, unsubstituted or substituted phenyl with up to three substituents ($R_7$-$R_9$), (meth)acrylate, or $C_{2-8}$ unsaturated hydrocarbon, wherein said $C_{2-8}$ unsaturated hydrocarbon is optionally terminated with amine, amide, carboxylic acid, ester, enone, oxime, O-methyl-oxime, imine, nitromethane, nitrile, ketone, mono-halo, di-halo, tri-halo, nitro, cyano, acrylonitrile, acrylonitrile-enoate, acrylonitrile-carboxylate, acrylonitrile-amide, alkylester, or a second aromatic or hetero-aromatic ring;
$R_3$-$R_5$ are independently selected from H, hydroxy, alkyl, alkoxy, fluoro, chloro, bromo, mono-halo alkoxy, di-halo alkoxy, tri-halo alkoxy, amino, alkylamino, dialkylamino, (thio)amido, alkyl(thio)amido, alkylthio, cyano, mercapto, nitro, mono-halo methyl, di-halo methyl, tri-halo methyl, ketone, carboxylic acid, thioc acid, alkylester, a surface-reactive group, a solid surface, and a functional group that can be linked to a reactive group on the solid surface;
$R_6$ is hydroxyl, alkoxy, fluoro, chloro, bromo, mono-halo alkoxy, di-halo alkoxy, tri-halo alkoxy, amino, alkylamino, dialkylamino, (thio)amido, alkyl(thio)amido, alkylthio, cyano, mercapto, nitro, mono-halo methyl, di-halo methyl, tri-halo methyl, ketone, carboxylic acid, alkylester; and
$R_7$-$R_{10}$ are independently selected from H, hydroxy, alkyl, alkoxy, fluoro, chloro, bromo, amino, alkylamino, dialkylamino, (thio)amido, alkyl(thio)amido, alkylthio, cyano, mercapto, nitro, and mono-, di-, or tri-halo methyl, ketone, carboxylic acid, thioic acid, and alkylester; and a nucleic acid molecule bound specifically to the compound,
wherein, upon specific binding of the nucleic acid molecule to the compound of formula (I) and upon exposure to radiation of suitable wavelength, the compound exhibits an increase in quantum yield in comparison to the quantum yield of the compound prior to specific binding.

6. A host cell containing the molecular complex according to claim 5.

7. A kit comprising:
a compound according to formula I below:

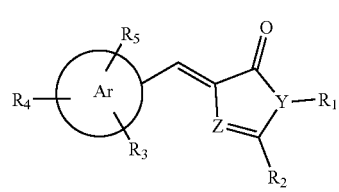

(I)

wherein,
O is S or O;
Y is N;
Z is N or $C(R_{10})$;
Ar is phenyl;
$R_1$ is —$(CH_2)_n$—$R_6$ where n is an integer greater than or equal to 1;
$R_2$ is methyl, mono-halo methyl, di-halo methyl, tri-halo methyl, aldoxime, an O-methyl-aldoxime, iminomethyl, carboxylic acid, thioic acid, (thio)amido, alkyl (thio)amido, unsubstituted or substituted phenyl with up to three substituents ($R_7$-$R_9$), (meth)acrylate, or $C_{2-8}$ unsaturated hydrocarbon, wherein said $C_{2-8}$ unsaturated hydrocarbon is optionally terminated with amine, amide, carboxylic acid, ester, enone, oxime, O-methyl-oxime, imine, nitromethane, nitrile, ketone, mono-halo, di-halo, tri-halo, nitro, cyano, acrylonitrile, acrylonitrile-enoate, acrylonitrile-carboxylate, acrylonitrile-amide, alkylester, or a second aromatic or hetero-aromatic ring;
$R_3$-$R_5$ are independently selected from H, hydroxy, alkyl, alkoxy, fluoro, chloro, bromo, mono-halo alkoxy, di-halo alkoxy, tri-halo alkoxy, amino, alkylamino, dialkylamino, (thio)amido, alkyl(thio)amido, alkylthio, cyano, mercapto, nitro, mono-halo methyl, di-halo methyl, tri-halo methyl, ketone, carboxylic acid, thioc acid, alkylester, a surface-reactive group, a solid surface, and a functional group that can be linked to a reactive group on the solid surface;
$R_6$ is hydroxy, alkoxy, fluoro, chloro, bromo, mono-halo alkoxy, di-halo alkoxy, tri-halo alkoxy, amino, alkylamino, dialkylamino, (thio)amido, alkyl(thio)amido, alkylthio, cyano, mercapto, nitro, mono-halo methyl, di-halo methyl, tri-halo methyl, ketone, carboxylic acid, or alkylester; and
$R_7$-$R_{10}$ are independently selected from H, hydroxy, alkyl, alkoxy, fluoro, chloro, bromo, amino, alkylamino, dialkylamino, (thio)amido, alkyl(thio)amido, alkylthio, cyano, mercapto, nitro, mono-halo methyl, di-halo methyl, tri-halo methyl, ketone, carboxylic acid, thioic acid, and alkylester; and
a nucleic acid molecule that binds to the compound of formula (I) to induce fluorescence thereof, wherein, upon specific binding of the nucleic acid molecule to the compound of formula (I) and upon exposure to radiation of suitable wavelength, the compound exhibits an increase in quantum yield in comparison to the quantum yield of the compound prior to specific binding.

8. A constructed DNA molecule comprising a first region encoding the nucleic acid molecule according to claim 1, wherein the nucleic acid molecule is an RNA molecule.

9. A method of detecting a target molecule comprising:
forming a molecular complex according to claim 5;
exciting the fluorophore with radiation of appropriate wavelength; and detecting fluorescence by the fluorophore, whereby fluorescence by the fluorophore identifies presence of the target molecule.

10. The method according to claim 9, wherein said forming is carried out in a cell.

11. The method according to claim 9, wherein the cell is ex vivo.

12. The method according to claim 9, wherein the cell is in vivo.

13. The molecular complex according to claim 5, wherein the nucleic acid molecule is selected from the group consisting of SEQ ID NOs: 5-10, 12, 13, 15, 17, 18, 20, 22, 23, 25, 26, 32-34, 55, and 56.

14. The kit according to claim 7, wherein the nucleic acid molecule is selected from the group consisting of SEQ ID NOs: 5-10, 12, 13, 15, 17, 18, 20, 22, 23, 25, 26, 32-34, 55, and 56.

* * * * *